(12) United States Patent
Zhou et al.

(10) Patent No.: US 11,685,731 B2
(45) Date of Patent: Jun. 27, 2023

(54) PROCESSES OF PREPARING A JAK1 INHIBITOR

(71) Applicant: Incyte Corporation, Wilmington, DE (US)

(72) Inventors: Jiacheng Zhou, Newark, DE (US); Yingrui Dai, Wilmington, DE (US); Zhongjiang Jia, Kennett Square, PA (US); Yongchun Pan, Wilmington, DE (US); James M. Parks, Newark, DE (US); Anthony J. Tomaine, Wilmington, DE (US); Jianji Wang, New Castle, DE (US); Aibin Zhang, Chester Springs, PA (US)

(73) Assignee: Incyte Corporation, Wilmington, DE (US)

(*) Notice: Subject to any disclaimer, the term of this patent is extended or adjusted under 35 U.S.C. 154(b) by 197 days.

(21) Appl. No.: 17/337,065

(22) Filed: Jun. 2, 2021

(65) Prior Publication Data
US 2021/0380563 A1    Dec. 9, 2021

Related U.S. Application Data

(60) Provisional application No. 63/033,618, filed on Jun. 2, 2020.

(51) Int. Cl.
    *C07D 403/14*      (2006.01)
    *B01J 31/28*      (2006.01)

(52) U.S. Cl.
    CPC ............ *C07D 403/14* (2013.01); *B01J 31/28* (2013.01)

(58) Field of Classification Search
None
See application file for complete search history.

(56) References Cited

U.S. PATENT DOCUMENTS

| | | |
|---|---|---|
| 5,521,184 A | 5/1996 | Zimmerman |
| 7,598,257 B2 | 10/2009 | Rodgers et al. |
| 7,834,022 B2 | 11/2010 | Rodgers et al. |
| 8,158,616 B2 | 4/2012 | Rodgers et al. |
| 8,410,265 B2 | 4/2013 | Zhou et al. |
| 8,415,362 B2 | 4/2013 | Rodgers et al. |
| 8,486,902 B2 | 7/2013 | Rodgers et al. |
| 8,604,043 B2 | 12/2013 | Li et al. |
| 8,691,807 B2 | 4/2014 | Yao et al. |
| 8,716,303 B2 | 5/2014 | Rodgers et al. |
| 8,765,734 B2 | 7/2014 | Huang et al. |
| 8,933,085 B2 | 1/2015 | Rodgers et al. |
| 8,987,443 B2 | 3/2015 | Liu et al. |
| 9,034,884 B2 | 5/2015 | Rodgers et al. |
| 9,181,271 B2 | 11/2015 | Li et al. |
| 9,193,733 B2 | 11/2015 | Rodgers et al. |
| 9,249,145 B2 | 2/2016 | Rodgers et al. |
| 9,359,358 B2 | 6/2016 | Rodgers et al. |
| 9,382,231 B2 | 7/2016 | Li et al. |
| 9,487,521 B2 | 11/2016 | Zhou et al. |
| 9,498,467 B2 | 11/2016 | Leopold et al. |
| 9,549,916 B2 | 1/2017 | Fu et al. |
| 9,926,301 B2 | 3/2018 | Li et al. |
| 9,926,601 B2 | 3/2018 | Gertler et al. |
| 10,435,392 B2 | 10/2019 | Li et al. |
| 11,001,571 B2 | 5/2021 | Li et al. |
| 2007/0135461 A1 | 6/2007 | Rodgers et al. |
| 2008/0312259 A1 | 12/2008 | Rodgers et al. |
| 2009/0233903 A1 | 9/2009 | Rodgers et al. |
| 2010/0113416 A1 | 5/2010 | Friedman et al. |
| 2011/0059951 A1 | 3/2011 | Rodgers et al. |
| 2011/0288107 A1 | 11/2011 | Parikh et al. |
| 2013/0045963 A1 | 2/2013 | Rodgers et al. |
| 2013/0060026 A1 | 3/2013 | Zhou et al. |
| 2014/0005166 A1 | 1/2014 | Rodgers |
| 2014/0135350 A1 | 5/2014 | Ni et al. |
| 2014/0343030 A1 | 11/2014 | Li et al. |
| 2015/0065484 A1 | 3/2015 | Yeleswara et al. |
| 2015/0087662 A1 | 3/2015 | Li et al. |
| 2015/0246046 A1 | 9/2015 | Vaddi |
| 2015/0342952 A1 | 12/2015 | Leopold et al. |
| 2015/0344497 A1 | 12/2015 | Zhou et al. |
| 2016/0289215 A1 | 10/2016 | Li et al. |
| 2018/0312492 A1 | 11/2018 | Li et al. |
| 2020/0010456 A1 | 1/2020 | Li et al. |
| 2021/0238168 A1 | 8/2021 | Li et al. |

FOREIGN PATENT DOCUMENTS

| | | |
|---|---|---|
| CN | 101910152 | 12/2010 |
| CN | 102026999 | 4/2011 |
| JP | 6415543 | 10/2018 |
| WO | WO 00/09495 | 2/2000 |
| WO | WO 00/053595 | 9/2000 |
| WO | WO 01/014402 | 3/2001 |

(Continued)

OTHER PUBLICATIONS

Burdeinick-Kerr et al., "Noncytolytic Clearance of Sindbis Virus Infection from Neurons by Gamma Interferon Is Dependent on Jak/Stat Signaling," Journal of Virology, Apr. 2009, 83(8):3429-3435.
Chen et al., "Rhinovirus Induces Airway Epithelial Gene Expression through Double-Stranded RNA and IFN-Dependent Pathways," Am J of Respir Cell and Mol Bio., Feb. 2006, 34(2): 192-203.
Kato et al., "Airway Epithelial Cells Produce B Cell-Activating Factor of TNF Family by an IFN--Dependent Mechanism1," J of Immunol., Nov. 15, 2006, 177(10):7164-7172.
Barabino et al., "Tear film and ocular surface tests in animal models of dry eye: uses and limitations," Experimental Eye Research, 2004, 79: 613-621.
Beck et al., "Brief Report: Alleviation of Systemic Manifestations of Castleman's Disease by Monoclonal Anti-Interleukin-6 Antibody," N. Engl. J. Med., 1994, 330(9): 602-605.

(Continued)

*Primary Examiner* — Joseph R Kosack
(74) *Attorney, Agent, or Firm* — Fish & Richardson P.C.

(57) ABSTRACT

The present application provides processes for preparing 4-[3-(cyanomethyl)-3-(3',5'-dimethyl-1H, 1'H-4,4'-bipyrazol-1-yl)azetidin-1-yl]-2,5-difluoro-N-[(1S)-2,2,2-trifluoro-1-methylethyl]benzamide, and phosphoric acid salt thereof, which is useful as a selective (Janus kinase 1) JAK1 inhibitor, as well as salt forms and intermediates related thereto.

80 Claims, 3 Drawing Sheets

(56) References Cited

FOREIGN PATENT DOCUMENTS

| | | |
|---|---|---|
| WO | WO 01/064655 | 9/2001 |
| WO | WO 03/024967 | 3/2003 |
| WO | WO 03/037347 | 5/2003 |
| WO | WO 03/099771 | 12/2003 |
| WO | WO 04/005281 | 1/2004 |
| WO | WO 04/046120 | 6/2004 |
| WO | WO 04/056786 | 7/2004 |
| WO | WO 04/080980 | 9/2004 |
| WO | WO 05/028444 | 3/2005 |
| WO | WO 2006/056399 | 6/2006 |
| WO | WO 2009/114512 | 9/2009 |
| WO | WO 2011/130146 | 10/2011 |
| WO | WO 2002/000196 | 1/2012 |
| WO | WO 2012/068450 | 5/2012 |
| WO | WO 2012/076063 | 6/2012 |
| WO | WO 2012/177606 | 12/2012 |
| WO | WO 2013/036611 | 3/2013 |
| WO | WO 2013/040863 | 3/2013 |
| WO | WO 2014/184275 | 11/2014 |
| WO | WO 2014/184327 | 11/2014 |
| WO | WO 2014/184328 | 11/2014 |
| WO | WO 2014/184350 | 11/2014 |

OTHER PUBLICATIONS

Bennett et al., "Proposals for the classification of the myelodysplastic syndromes," British Journal of Haematology, 1982, 51: 189-199.
Berge et al., "Pharmaceutical Salts," J. Pharma. Science, 1977, 66(1): 1-19.
Bhattacharya et al., "Brittain, ed. Polymorphism in Pharmaceutical Solids," 2009, p. 327-345.
Roche, "Bioreversible Carriers in Drug Design," American Pharmaceutical Association and Pergamon Press, 1987, Front Matter Only, 4 pages.
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chormatography—Mass Spectrometiy," J. Comb. Chem., 2002, 4: 295-301.
Bock et al. "Managing drug resistance in cancer: lessons from HIV therapy." Nature, Jul. 2012, vol. 12, pp. 494-501.
Bolen, "Nonreceptor tyrosine protein kinases", Oncogene, 1993, 8(8):2025-31.
Bollrath et al., "gp130-Meidated Stat3 Activation in Enterocytes Regulates Cell Survival and Cell-Cycle Progression during Colitis-Associated Tumorigenesis," Cancer Cell, 15: 91-102 (2009).
Borie et al., "Combined Use of the Jak3 Inhibitor CP-690, 550 with Mycophenolate Mofetil to Prevent Kidney Allograft Rejection in Nonhuman Primates," Transplantation, Dec. 2005, 80(12): 1756-64.
Bosworth, "JAK1/JAK2 Inhibitor Ruxolitinib Is a Rising Start," Clinical Oncology, Apr. 2011, 06:04, 3 pages.
Boudny, et al., "JAK/STAT signaling pathways and cancer", Neoplasm, 49:349-355, 2002.
Bowman, et al. "STATs in oncogenesis", Oncogene, 19:2474-2488, 2000.
Bromberg et al., "Inflammation and Cancer: IL-6 and STA T3 Complete the Link," Cancer Cell, 15:79-80 (2009).
Brunning and Germing, "Myelodysplastic syndromes/neoplasms" in Chapter 5, Swerdlow, et al., eds. WHO Classification of Tumours of Haematopoietic and Lymphoid Tissues, (ed. 4th edition): Lyon, France: IARC Press, 2008, 4$^{th}$ edition, pp. 88-103.
Burger et al., "Janus kinase inhibitor INCB20 has antiproliferative and apoptotic effects on human myeloma cells in vitro and in vivo", Mol. Cancer Ther. 2009:8(1), Jan. 2009 pp. 26-35.
Burger, et al., "Gp130 and ras mediated signaling in human plasma cell line IN/a-6: a cytokine-regulated tumor model for plasmacytoma", Hematol J., 2:42-53, 2001.

Campas-Moya, C., "Ruxolitinib. Tyrosine-protein kinase JAK1/2 inhibitor, treatment of myelofibrosis, treatment of myeloproliferative neoplasms, treatment of psoriasis", Drugs of the Future, (Jun. 2010) vol. 35, No. 6, pp. 457-465.
Candotti, et al. (2002). "Molecular aspects of primary immunodeficiencies: lessons from cytokine and other signaling pathways.", J Clin Invest, 109(10): 1261-9.
Candotti, F., et al. (1997). "Structural and functional basis for JAK3-deficient severe combined immunodeficiency.", Blood, 90(10): 3996-4003.
Cetkovic-Cvrlje, et al. (2003). "Targeting JAK3 with JANEX-1 for prevention of autoimmune type 1 diabetes in NOD mice.", Clin Immunol, 106(3): 213-25.
Chalandon, "Targeting mutated protein tyrosine kinases and their signaling pathways in hematologic malignancies", Haematologica, 90 (7):949-68 (2005).
Changelian, et al., "Prevention of Organ Allograft Rejection by a Specific Janus Kinase 3 Inhibitor", Science, 2003, 302, 875-878.
Chari et al., "Complete Remission Achieved with Single Agent CNTO 328, an Anti-IL-6 Monoclonal Antibody, in Relapsed and Refractory Myeloma," *Clinical Lymphoma, Myeloma & Leukemia*, 2013, 13(3):333-337.
Chen et al., "Blockade of interleukin-6 signaling augments regulatory T-cell reconstitution and attenuates the severity of graft-versusl-host disease," Blood, Jul. 2009, 114(4): 891-900.
Chen et al., "Induction of myelodysplasia by myeloid-derived suppressor cells," J Clin Invest, Nov. 2013, 123(11): 4595-611.
Chen, et al., "Stat3 Activation in Human Endometrial and Cervical Cancer", British Journal of Cancer, 96, 591-599, 2007.
Cheson et al., "Report of an international working group to standardize response criteria for myelodysplastic syndromes," Blood, Dec. 2000, 96(12): 3671-4.
Choy et al., "Therapeutic Benefit of Blocking Interleukin-6 Activity With an Anti-Interleukin-6 Receptor Monoclonal Antibody in Rheumatoid Arthritis," Arthritis & Rheumatism, 2002, 46(12) 3143-3150.
Cilloni et al., "Emerging drugs for chronic myeloid leukemia", Expert Opinion on Emerging Drugs, (Jun. 2010) vol. 15, No. 2, pp. 175-184.
Claessens et al., "In vitro proliferation and differentitation of erythyroid progenitors from patients with myelodysplastic syndromes: evidence for Fas-dependent apoptosis," Blood, Mar. 2012, 1594-1601.
Clark et al., "Discovery and Development of Janus Kinase (JAK) inhibitors for Inflammatory Diseases," J Med Chem., 2014, pp. A-P.
Conklyn, M. et al., "The JAK3 inhibitor CP0690550 selectively reduces NK and CD8+ cell numbers in cynomolgus monkey blood following chronic oral dosing", Journal of Leukocyte Biology, 2004, 76, 1248-1255.
De Vos, J., et al. (2000). "JAK2 tyrosine kinase inhibitor tyrphostin AG490 downregulates the mitogen-activated protein kinase (MAPK) and signal transducer and activator of transcription (STAT) pathways and induces apoptosis in myeloma cells.", Br J Haematol, 109(4): 823-8.
Deuse, T. et al., "Novel Immunosuppression: R348, a JAK3- and Syk-Inhibitor Attenuates Acute Cardiac Allograft Rejection", Transplantation, 2008, 85(6) 885-892.
Dudley et al., "A VEGF/JAK2/STAT5 axis may partially mediate endothelial cell tolerance to hypoxia," Biochem J, Sep. 2005, 390(Pt 2): 427-36.
Eghtedar, "Phase II Study of the JAK2 Inhibitor, INCB018424, in Patients with Refractory Leukemias Including Post-Myeloproliferative Disorder Acute Myeloid Leukemia", American Society of Hematology (ASH) annual meeting in Orlando, FL (Dec. 6, 2010), Abstract/poster 509.
Fayad et al., "Interleukin-6 and interleukin-10 levels in chronic lymphocytic leukemia: correlation with phenotypic characteristics and outcome," Blood, Jan. 2001, 97(1): 256-263.
Fenaux et al., "A randomized phase 3 study of lenalidomide versus placebo in RBC transfusion-dependent patients with Low-/Intermediate-1-risk myelodysplastic syndromes with del5q," Blood, Oct. 2011, 118(14): 3765-76.

(56) References Cited

OTHER PUBLICATIONS

Fenaux, et al., "Efficacy of azacitidine compared with that of conventional care regimens in the treatment of higher-risk myelodysplastic syndromes: a randomised, open-label, phase III study," Lancet Oncol, Mar. 2009, 10: 223-32.
Fiskus, W. et al., "Synergistic Activity of Combinations of JAK2 Kinase Inhibitor with PI3K/mTOR, MEK or PIM Kinase Inhibitor Against Human Myeloproliferative Neoplasm Cells Expressing JAK2V617F" J. American Chem. Soc., 52nd Annual Meeting of the American-Society-of-Hematology (ASH); Orlando, FL, USA; Dec. 4-7, 2010, ACS Publications; vol. 116, No. 21 Nov, 1, 2010 p. 349, XP002667216, ISSN: 0002-7863 (1 page).
Flex E., et al., "Somatically acquired JAK1 mutations in adult acute lymphoblastic leukemia", J. Exp Med. 205:751-8, (2008).
Fonseca et al., "Interleukin-6 as a key player in systemic inflammation and joint destruction," Autoimmun Rev, Jun. 2009, 8(7): 538-42.
Fridman, et al., "Preclinical evaluation of local JAK1 and JAK2 inhibition in cutaneous inflammation", Journal of Investigative Dermatology, (Sep. 2011) vol. 131, No. 9, pp. 1838-1844.
Fridman, J. et al. "Selective JAK Inhibition is Efficacious against Multiple Myeloma Cells and Reverses the Protective Effects of Cytokine and Stromal Cell Support" Abstract #0956, presented Sunday, Jun. 15, 2008 at the European Hematology Association, 13th Congress, Jun. 12-15, Copenhagen, Denmark (1 page).
Fridman, Jordan et al. "Discovery and Preclinical Characterization of INCB018424, a Selective JAK2 Inhibitor for the Treatment of Myeloproliferative Disorders" poster presented at the American Society of Hematology, 49th Annual Meeting and Exposition, GA. Abstract #3538, poster #757, Dec. 10, 2007 (1 page).
Fridman, Jordan et al. "Efficacy and Tolerability of Novel JAK Inhibitors in Animal Models of Rheumatoid Arthritis" poster presented at the ACR/ARHP (American College of Rheumatology/Association of Rheumatology Health Professionals) Scientific Meeting 2007, Boston, MA. Nov. 10, 2007. Abstract 1771, poster 285 (1 page).
Fridman, Jordan, et al. "Discovery and Preclinical Development of Selective JAK Inhibitors for the Treatment of Hematological Malignancies" poster presented at European Hematology Association, 12th Congress, Vienna, Austria. Abstract 0324, Jun. 8, 2007 (1 page).
Fridman, Jordan, et al. "Discovery and Preclinical Development of Selective JAK Inhibitors for the Treatment of Myeloproliferative Disorders" poster presented at the 4th International Congress on Myeloproliferative Diseases and Myelodysplastic Syndromes, New York, NY. Nov. 8-10, 2007. Poster 0009 (1 page).
Fujii, C. et al., "Aberrant expression of serine.thereonine kinase Pim-3 in hepatocellular carcinoma development and its role in the proliferation of human hepatoma cell lines" International Journal of Cancer 114: 209-218, (2005).
Gaestel et al., "Targeting innate immunity protein kinase signalling in inflammation," Nat Rev Drug Discov., Jun. 2009, 8(6):480-99.
Goodman, et al., "IL-6 Signaling in Psoriasis Prevents Immune Suppression by Regulatory T Cells," J. Immunol., Sep. 2009, 183: 3170-3176.
Gorre, M.E. et al., "Clinical Resistance to STI-571 Cancer Therapy Caused by BCR-ABL Gene Mutation or Amplification," Science, 293:876, 2001.
Gottlieb, A.B., et al, "Psoriasis: Emerging Therapeutic Strategies", Nat Rev Drug Disc., 4:19-34 (2005).
Grabbe, et al., "Immunoregulatory mechanisms involved in elicitation of allergic—contact hypersensitivity", Immunol Today, Jan. 19(1):37-44 (1998) (only 1 page provide and marked "best available").
Greenberg, "The myelodysplastic syndromes" in Hoffman, et al, eds. Hematology: Basic Principles and Practice (3rd ed.), Churchill Livingston; 2000:1106-1129.
Greene, Protective Groups in Organic Synthesis, 4th ed., John Wiley & Sons: New Jersey, (2007), 1111 pages.

Gregory, et al., "Clinical and laboratory features of myelofibrosis and limitations of current therapies", Clinical Advances in Hematology and Oncology, (Sep. 2011) vol. 9, No. 9, pp. 1-3.
Grivennikov, et al., "IL-6 and STAT3 are required for survival of intestinal epithelial cells and the development of colitis-associated cancer", Cancer Cell, 15:103-111 (2009).
Groneberg et al., "Animal models of allergic and inflammatory conjunctivitis," Allergy, Nov. 2003, 58(11): 1101-13.
Grossman, et al., "Interleukin 6 is expressed in high levels in psoriatic skin and stimulates proliferation of cultured human keratinocytes," Proc. Natl. Acad., Sci. USA, Aug. 1989, 86: 6367-6371.
Guschin, et al., "A major role for the protein tyrosine kinase JAK1 in the JAKISTAT signal transduction pathway in response to interleukin-6", Embo J 14:1421-1429 (1995).
Hardwicke, et al., "GSK1070916, a potent Aurora B/C kinase inhibitor with broad antitumor activity in tissue culture cells and human tumor xenograft models", Molecular Cancer Therapeutics 8(7), 1808-1817 (2009).
Harris et al., "World Health Organization classification of neoplastic diseases of the hematopoietic and lymphoid tissues: report of the Clinical Advisory Committee meeting-Airlie House, Virginia, Nov. 1997," J Clin Oncol, Dec. 1999, 17(12): 3835-49.
Huang, "Inhibition of STAT3 activity with AG490 decreases the invasion of human pancreatic cancer cells in vitro", Cancer Sci. 97(12):1417-23 (2006).
Hyung-Bae et al., Transplantation, 2010, 90(8):825-835.
International Search Report and Written Opinion in International Application No. PCT/US2014/038388, dated Sep. 1, 2014, 9 pages.
International Preliminary Report on Patentability in International Application No. PCT/US2014/038388, dated Nov. 17, 2015, 7 pages.
International Search Report and Written Opinion in International Application No. PCT/US2021/035400, dated Aug. 12, 2021, 14 pages.
Ishizaki, et al., "Pharmacological Properties of Y-27632, a Specific Inhibitor of Rho-Associated Kinases", Molecular Pharmacology, 2000, 57, 976-983.
Itagaki, et al., "Expedient Synthesis of Potent Cannabinoid Receptor Agonist (−)-CP55,940", Organic Letters, 2005; 7(19); 4181-4183.
Jädersten et al., "Long-term outcome of treatment of anemia in MDS with erythropoietin and G-CSF," Blood, Aug. 2005, 106(3): 803-11.
James, et al., "A unique clonal JAK2 mutation leading to constitutive signalling causes polycythaemia vera", Nature, 434 (7037):1144-8 (2005).
Janes, M. et al., "Effective and selective targeting of leukemia cells using a TORC1/2 kinase inhibitor.", Nature Medicine (2010) LNKD-PUBMED:20072130, vol. 16, No. 2, pp. 205-213 XP002673719.
Jee, et al., "Overview: animal models of osteopenia and osteoporosis", J Musculoskel. Neuron, Interact, 1(3):193-207 (2001).
Kaercher, T., "Ocular symptoms and signs in patients with ectodermal dysplasia symdromes", Grafes Arch Clin Exp Ophthalmol, 2004;495-500.
Kamb, Nature Reviews Drug Discovery 4, pp. 161-165 (2005).
Kantarjian et al., "Decitabine improves patient outcomes in myelodysplastic syndromes: results of phase III randomized study," Cancer, Apr. 2006, 106(8): 1794-803.
Kaushansky, K., "Lineage-Specific Hematopoietic Growth Factors", NEJM 354:2034-45 (2006).
Kawamura, et al. (1994). "Molecular cloning of L-JAK, a Janus family protein-tyrosine kinase expressed in natural killer cells and activated leukocytes.", Proc Natl Acad Sci U S A, 91(14): 6374-8).
Kharas, et al., "ABL Oncogenes and Phosphoinositide 3-Kinase: Mechanism of Activation and Downstream Effectors.", Cancer Res., 65(6):2047-2053, Mar. 15, 2005.
Killedar et al., "Early pathogenic events associated with Sjogren's syndrome (SjS)-like disease of the NOD mouse using microarray analysis," Lab Invest, Deember 2006, 86(12): 1243-1260.
Kiss, Robert, "Recent developments on JAK2 inhibitors: A patent review", Expert Opinion on Therapeutic Patents, (Apr. 2010) vol. 20, No. 4, pp. 471-495.

(56) References Cited

OTHER PUBLICATIONS

Kola, Nature Reviews Drug Discovery 3, pp. 711-715 (2004).
Kortylewski, et al., "Regulation of the IL-23 and IL-12 balance by Stat3 signaling in the tumor microenvironment", Cancer Cell, 15:114-123 (2009).
Kruh et al., "The complete coding sequence of arg defines the Abelson subfamily of cytoplasmic tyrosine kinases.", Proc. Natl. Acad. Sci., 87:5802-5806, Aug. 1990.
Kudlacz, et al. "The JAK-3 inhibitor CP-690550 is a potent anti-inflammatory agent in a murine model of pulmonaiy eosinophilia", European Journal of Pharmacology 582 (2008) 154-161.
Kumar, C., "Kinase drug discovery approaches in chronic myeloproliferative disorders", Oncogene, (Jun. 18, 2009) vol. 28, No. 24, pp. 2305-2323.
Kurzrock et al., "Serum Interleukin 6 Levels Are Elevated in Lymphoma Patients and Correlate with Survival in Advanced Hodgkin's Disease and with B Symptoms," Cancer Res., May 1993, 52:2118-2122.
Kurzrock et al., "A Phase I, Open-Label Study of Siltuximab, an Anti-IL-6 Monoclonal Antibody, in Patients with B-cell Non-Hodgkin Lymphoma, Multiple Myeloma, or Castleman Disease," Clin. Cancer Res., published online May 9, 2013, 39 pages.
Lai, et al., "Mechanistic Study on the Inactivation of General Acyl-CoA Dehydrogenase by a Metabolite of Hypoglycin A", J. Am. Chem. Soc. 113: 7388-7397 (1991).
Larson, "Myelodysplasia: when to treat and how," Best Pract Res Clin Haematol, 2006, 19(2): 293-300.
Lemp, "The Definition and Classification of Dry Eye Disease: Report of the Definition and Classification Subcommittee of the International Eye Workshop," The Ocular Surface, 5(2): 75-92.
Levine, et al., "Activating mutation in the tyrosine kinase JAK2 in polycythemia vera, essential thrombocythemia, and myeloid metaplasia with myelofibrosis", Cancer Cell, vol. 7, 2005: 387-397.
Levitzki, "Tyrosine kinases as targets for cancer therapy", Eur. J. Cancer 38(suppl. 5):S11-S18 (2002).
Levy, et al. "INCB018424 A Selective Janus Kinase 1/2 Inhibitor" Presentation at the 50th American Society of Hematology Annual Meeting (ASH), Dec. 8, 2008.
Levy, et al., INCB18424 Discussion presentation at the American Society of Hematology, 49th Annual Meeting and Exposition, Atlanta, GA. Abstract #558, Dec. 10, 2007 (25 pages).
Li, et al., "Pim-3, a proto-oncogene with serine/threonine kinase activity, is aberrantly expressed in human pancreatic cancer and phosphorylates Bad-mediated apoptosis in human pancreatic cell lines" Cancer Research 66(13): 6741-7 (2006).
Liesveld and Lichtman, Chapter 88. "Myelodysplastic Syndromes (Clonal Cytopenias and Oligoblastic Myelogenous Leukemia)", in Prchal et al, eds. Williams Hematology. 8th ed., New York: McGraw-Hill; 2010.
Lin, "Constitutive Activation of JAK3/STAT3 in Colon Carcinoma Tumors and Cell Lines", Am J Pathol. 167(4):969-80 (2005).
Lin, et al., "Enantioselective synthesis of Janus kinase inhibitor INCB018424 via an organocatalytic aza-Michael reaction," Organic Letters, (2009), 11(9), 1999-2002.
List et al., "Efficacy of lenalidomide in myelodysplastic syndromes," N Engl J Med, Feb. 2005, 352(6): 549-57.
Liu, et al., "Combined Inhibition of Janus Kinase 1/2 for the Treatment of JAK2V617F-Driven Neoplasms: Selective Effects on Mutant Cells and Improvements in Measures of Disease Severity", Clin Cancer Res 2009;15(22) pp. 6891-6900; Nov. 15, 2009; Published Online First on Nov. 3, 2009 as 10.1158/1078-0432.CCR-09-1298.
Lübbert, et al., "Cytogenic responses in high-risk myelodysplastic syndrome following low-dose treatment with the DNA methylation inhibitor 5-aza-2'-deoxycytidine," Br J Haematol, Aug. 2001, 114(2): 349-57.
Lübbert, et al., "Low-dose decitabine versus best supportive care in elderly patients with intermediate- or high-risk myelodysplastic syndrome (MDS) ineligible for intensive chemotherapy: final results of the randomized phase III study of the European Organisation for Research and Treatment of Cancer Leukemia Group and the German MDS Study Group," J Clin Oncol, May 2011, 29(15): 1987-96.
Lucet et al., "The structural basis of Janus kinas 2 inhibition by a potent and specific pan-Janus kinase inhibitor," Blood, 2006, 107(1):176-183.
Macchi, et al., "Mutations of Jak-3 gene in patients with autosomal severe combined immune deficiency (SCID)", Nature 377:65-8 (1995).
Madden et al. Comparative study of two non-invasive tear film stability techniques. Curr Eye Res, 1994; 13(4):263-9.
Madhusudan et al., "Tyrosine kinase inhibitors in cancer therapy", Clin Biochem., 2004, 37(7):618-35.
Mainstone et al., "Tear meniscus measurement in the diagnosis of dry eye", Curr Eye Res, 1996; 15:653-661.
Mancini, M. et al., "RAD 001 (everolimus) prevents mTOR and Akt late re-activation in response to imatinib in chronic myeloid leukemia.", J. Cellular Biochemistry (2010) LNKD-PUBMED:20014066, XP-002673720 vol. 109, No. 2 (2010) pp. 320-328.
Maxson et al., "Oncogenic CSF3R Mutations in Chronic Neutrophilic Leukemia and Atypical CML," N. Engl. J. Med., 2013, 368(19): 1781-1790.
McMillan, "The systemic inflammation-based Glasgow Prognostic Score: a decade of experience in patients with cancer," Cancer Treat Rev, Aug. 2013, 39(5): 534-40.
Mesa, et al. "INCB018424, A Selective JAK 1/2 Inhibitor, Significantly Improves the Compromised Nutritional Status and Frank Cachexia in Patients with Myelofibrosis (MF)" Poster #1760 at the American Society of Hematology Annual Meeting (ASH), Dec. 6, 2008 (19 pages).
Mesa, et al., "Evaluating the serial use of the myelofibrosis symptom assessment form for measuring symptomatic improvement: Performance in 87 myelofibrosis patients on a JAK1 and JAK2 inhibitor (INCB018424) clinical trial", Cancer, (Nov. 1, 2011) vol. 117, No. 21, pp. 4869-4877.
Mesa, R. et al., "Emerging drugs for the therapy of primary and post essential thrombocythemia, post polycythemia vera myelofibrosis", Expert Opinion on Emerging Drugs England, vol. 14, No. 3 (2009) pp. 471-479.
Meydan et al., "Inhibition of acute lymphoblastic leukaemia by a Jak-2 inhibitor", Nature. Feb. 15, 1996;379(6566):645-8.
Milici, A. J., et al., "Cartilage preservation by inhibition of Janus kinase 3 in two rodent models of rheumatoid arthritis", Arthritis Research & Therapy, 2008, 10:R14 (http://arthritis-research.com/content/10/1/R14) (9 pages).
Minegishi, et al., "Human Tyrosine Kinase 2 Deficiency Reveals Its Requisite Roles in Multiple Cytokine Signals Involved in Innate and Acquired Immunity", Immunity 25:745-55 (2006).
Mishchenko et al., "Treatment options for hydroxyurea-refractory disease complications in myeloproliferative neoplasms: JAK2 inhibitors, radiotherapy, splenectomy and transjugular intrahepatic portosystemic shunt", Eur J Haematol. Sep. 2010;85(3):192-9, Epub Jun. 2, 2010.
Miyoshi et al., "Interleukin-8 concentrations in conjunctival epithelium brush cytology samples correlate with neutrophil, eosinophil infiltration, and corneal damage", Cornea, 2001;20:743-7.
Molldrem, et al., "Antithymocyte globulin for patients with myelodysplastic syndrome," Br J Haematol, Dec. 1997, 99(3): 699-705.
Moreland, et al. "A Randomized Placebo-Controlled Study of INCBO 18424, a Selective Janus Kinase 1&2 (JAK 1&2) Inhibitor in Rheumatoid Arthritis (RA)" Presentation at the American College of Rheumatology meeting, Oct. 26, 2008. (20 pages).
Mullighan, et al., "JAK mutations in high-risk childhood acute lymphoblastic leukemia", Proc Natl Acad Sci USA. 106:9414-8 (2009).
Mundle, et al. Am J Hematol 1999;60:36-47.
Naka T., "The paradigm of IL-6: from basic science to medicine", Arthritis Res., 2002;4 Suppl 3:S233-42.
Nakagawara, Akira, "Trk receptor tyrosine kinases: A bridge between cancer and neural development." Cancer Letters, 169:107-114, 2001.

(56) References Cited

OTHER PUBLICATIONS

Naqvi, et al., "A potential role of ruxolitinib in leukemia", Expert Opinion on Investigational Drugs, (Aug. 2011) vol. 20, No. 8, pp. 1159-1166.
National Cancer Institute, "FDA Approval for Ruxolitinib Phosphate", http://www.cancer.gov/cancertopics/dmginfo/fda-ruxolitinibphosphate posted Nov. 18, 2011 (3 pages).
Neidle, Stephen, Cancer Drug Design and Discovery, (Elsevier/Academic Press, 2008) pp. 427-431.
Neubauer, H., et al., "Jak2 Deficiency Defines an Essential Developmental Checkpoint in Definitive Hematopoiesis", Cell, 93(3): 397-409 (1998).
Neuner, et al., J. Invest. Dermatol. 1991, 97, 27-33.
Nicholoff et al., "Recent Insights into the immunopathogenesis of psoriasis provide new therapeutic opportunities", J. Clin. Invest., 113; 1664-1675 (2004).
Nishimoto et. al., "Improvement in Castleman's disease by humanized anti-interleukin-6 receptor antibody theraphy," Blood, 2000, 95(1):56-61.
Norman, "Selective JAKI inhibitor and selective Tyk2 inhibitor patents," Expert Opinion, Informa Healthcare. 2012, available at: <http://informahealthcare.com/dol/pdfplus/10.1517/13543776.2012. 723693>.
Ortmann, et al., "Janus kinases and signal transducers and activators of transcription: their roles in cytokine signaling, development and immunoregulation." Arthritis Res, 2(1): 16-32 (2000).
Ostojic et al., "Ruxolitinib for the treatment of myelofibrosis", Drugs of Today, (Nov. 2011) vol. 47, No. 11, pp. 817-827.
Panteli et al., "Serum interleukin (IL)-1, IL-2, sIL-2Ra, IL-6 and thrombopoietin levels in patients with chronic myeloproliferative diseases," British Journal of Haematology, 2005, 130, 709-715.
Pardanani A., "JAK2 inhibitor therapy in myeloproliferative disorders: rationale, preclinical studies and ongoing clinical trialsJAK2 inhibitor therapy in MPD", Leukemia 22, Jan. 23-30, 2008.
Parganas, E., D. Wang, et al., "Jak2 is Essential for Signaling through a Variety of Cytokine Receptors", (1998). Cell, 93(3): 385-95.
Park et al., "Homogeneous Proximity Tyrosine Kinase Assays: Scintillation Proximity Assay versus Homogeneous Time-Resolved Fluorescense", Analytical Biochemistry, 1999, 269, 94-104.
Parks, "Tofacitinib and Other Kinase Inhibitors Offer New Approach to Treating Rheumatoid Arthritis," Rheumatologist, Jun. 2013, pp. 1-12 Available from: <http://www.the-rheumatologist.org/details/article/4871781/Tofacitinib_and_Other_Kinase_Inhibitors_Offer_New_Approach_to_Treating_Rheumatoi.html>, 12 pages.
Pedranzini, et al., Cancer Res., 66(19):9714-9721 (2006).
Pernis, et al., "JAK-STAT signaling in asthma." J Clin Invest, 109(10): 1279-83 (2002).
Punwani et al., Poster/presentation, "Initial Efficacy and Safety of Topical INCYB018424 Cream, a Selective Janus Kinase 1&2 (JAK 1&2) Inhibitor in Psoriasis" 17th Congress of the European Academy of Dermatology and Venereology, Paris, France, Sep. 17, 2008 (15 pages).
Punwani, Naresh, et al. "Efficacy and safety of topical INCB018424, a selective Janus kinase 1 & 2 (JAK1&2) inhibitor in psoriasis." Journal of the American Academy of Dermatology. vol. 60. No. 3. 360 Park Avenue South, New York, NY 10010-1710 USA: Mosby-Elsevier, 2009.
Quintas-Cardama et al., "Preclinical characterization of the selective JAK1/2 inhibitor INCB018424: therapeutic implications for the treatment of myeloproliferative neoplasms", Blood First Edition Paper, prepublished online Feb. 3, 2010, American Society of Hematology; DOI 10.1182/blood-2009-04-214957, 115(15):3109-3117.
Raza et al., "Novel insights into the biology of myelodysplastic syndromes: excessive apoptosis and the role of cytokines," Int J Hematol, Jun. 1996, 63(4): 265-78.
Raza et al., "The myelodysplastic syndromes in 1996: complex stem cell disorders confounded by dual actions of cytokines," Leuk Res, Nov.-Dec. 1996, 20(11-12): 881-90.
Raza et al., "Apoptosis in bone marrow biopsy samples involving stromal and hematopoietic cells in 50 patients with myelodysplastic syndromes," Blood, Jul. 1995, 86(1): 268-76.
Raza et al., "Phase 2 Study of lenalidomide in transfusion-dependent, low-risk, and intermediate-1 risk myelodysplastic syndromes with karyotypes other than deletion 5q," Blood, Jan. 2008, 111(1): 86-93.
Remington's Pharmaceutical Sciences, 17th ed., Mack Publishing Company, Easton, Pa., 1985, p. 1418.
Roberts et al., "Trends in the risks and benefits to patients with cancer participating in phase 1 clinical trials," JAMA, Nov. 2004, 292(17): 2130-40.
Rodig, et al., "Disruption of the Jak1 gene demonstrates obligatory and nomedundant roles of the Jaks in cytokine-induced biologic responses." Cell, 93(3): 373-83 (1998).
Roudebush et al., "Pharmacologic manipulation of a four day murine delayed type hypersensitivity model," Agents Actions, Jan. 1993, 38(1-2): 116-21.
Rousvoal, G. et al. "Janus kinase 3 inhibition with CP-690,550 prevents allograft vasculopathy", Transpl Int., 2006 19(12):1014-21.
Samanta et al., "Janus kinase 2: a critical target in chronic myelogenous leukemia", Cancer Res. Jul. 1, 2006;66(13):6468-72.
Schiffer, "Clinical issues in the management of patients with myelodysplasia," Hematology Am Soc Hematol Educ Program, 2006: 205-10.
Schiffer, "Myelodysplasia: the good, the fair and the ugly," Best Pract Res Clin Haematol, Mar. 2007, 20(1): 49-55.
Schindler et al., "Hormones and Signaling: Cytokines and STAT Signaling", Adv Pharmacol. 2000; 47:113-74.
Schrader et al., "Animal models of dry eye," Dev Opthalmol, 2008, 41:298-312.
Scott, et al., "Jaks, STATs, Cytokines, and Sepsis." Clin Diagn Lab Immunol, 9(6): 1153-9 (2002).
Seki, "STAT3 and MAPK in human lung cancer tissues and suppression of oncogenic growth by JAB and dominant negative STAT3", Int J Oncol. 24(4):931-4 (2004).
Seto, et al. (2003). "Enhanced Th2 cell-mediated allergic inflammation in Tyk2-deficient mice." J Immunol, 170(2): 1077-83.
Shah et al., "Multiple BCR-ABL kinase domain mutations confer polyclonal resistance to the tyrosine kinase inhibitor imatinib (STI571) in chronic phase and blast crisis chronic myeloid leukemia." Cancer Cell, 2:117-125, Aug. 2002.
Shi, et al., "The pharmacokinetics, pharmacodynamics, and safety of orally dosed INCB018424 phosphate in healthy volunteers", Journal of Clinical Pharmacology, (Dec. 2011) vol. 51, No. 12, pp. 1644-1654.
Silverman et al., "Further analysis of trials with azacitidine in patients with myelodysplastic syndrome: studies 8421, 8921, and 9221 by the Cancer and Leukemia Group B," J Clin Oncol, Aug. 2006, 24(24): 3895-903.
Silverman et al., "Randomized controlled trial of azacitidine in patients with the myelodysplastic syndrome: a study of the cancer and leukemia group B," J Clin Oncol, May 2002, 20(10): 2429-40.
Sloand et al., "Factors affecting response and survival in patients with myelodysplasia treated with immunosuppressive therapy," J Clin Oncol, May 2008, 26(15): 2505-11.
Smith et al., "Basic pathogenic mechanisms operating in experimental models of acute anteriior uveitis," Immunol Cell Biol, Dec. 1998, 76(6): 497-512.
Smolen, et al., "Effect of interleukin-6 receptor inhibition with tocilizumab in patients with rheumatoid arthritis (OPTION study): a double-blind, placebo-controlled, randomized trial", Lancet 371:987, 2008 (2008).
Sonbol et al., "Comprehensive review of JAK inhibitors in myeloproliferative neoplasms," Therapeutic Advances in Hematology, 2013, 4(1): 15-35.
Song et al. "JAK1 Activates STAT3 Activity in Non-Small-Cell Lung Cancer cells and IL-6 Neutralizing Antibodies can Suppress JAK1-STAT3 Signaling," Mol Cancer Ther., Mar. 2011, 10(3): 481-94.
Spoerl et al., "Activity of therapeutic JAK 1/2 blockade in graft-versus-host disease," Blood, Jun. 2014, 123(24): 3832-42.

(56) References Cited

OTHER PUBLICATIONS

Sriram, K. et al., "Induction of gp130-related Cytokines and Activation of JAK2/STAT3 Pathway in Astrocytes Precedes Upregulation of Glial Fibrillary Acidic Protein in the 1-Methyl-4-phenyl-1,2,3,6-tetrahydropyridine Model of Neurodengeneration", J. Biol. Chem., 2004, 279(19): 19936-47. Epub Mar. 2, 2004.
Staerk, J., et al., "JAK1 and Tyk2 activation by the homologous polycythemia vera JAK2 V617F mutation: cross-talk with IGF1 receptor", J Biol Chem., 280:41893-41899 (2005).
Stirewalt et al., "Predictors of relapse and overall survival in Philadelphia chromosome-positive acute lymphoblastic leukemia after transplantation", Biol Blood Marrow Transplant. Mar. 2003;9(3):206-12.
Strassmann et al., "Suramin Interferes with Interleukin-6 Receptor Binding in Vitro and Inhibits Colon-26-mediated Experimental Cancer Cachexia in Vivo," J. Clin. Invest., Nov. 1993, 92: 2152-2159.
Symington et al., "The relationship of serum IL-6 levels to acute graft-versus-host disease and hepatorenal disease after human bone marrow transplantation," Transplantation, Sep. 1992, 54(3): 457-62.
Takemoto, et al. (1997). "Proliferation of adult T cell leukemia/lymphoma cells is associated with the constitutive activation of JAK/STAT proteins." Proc Natl Acad Sci U S A, 94(25): 13897-902.
Tamura et al., "Involvement of Human Interleukin 6 in Experimental Cachexia Induced by a Human Uterine Cervical Carcinoma Xenograft," Clin. Cancer Res., Nov. 1995, 1: 1353-1358.
Tefferi, A. et al. "The Clinical Phenotype of Myelofibrosis Encompasses a Chronic Inflammatory State that is Favorably Altered by INCB018424, A Selective Inhibitor of JAK1/2" Poster #2804 at the American Society of Hematology Annual Meeting (ASH), Dec. 7, 2008, (18 pages).
Tefferi, Ayalew, "Primary myelofibrosis: 2012 update on diagnosis, risk stratification, and management", American Journal of Hematology, (Dec. 2011) vol. 86, No. 12, pp. 1017-1026.
Tefferi, et al., "Serious adverse events during ruxolitinib treatment discontinuation in patients with myelofibrosis", Mayo Clinic Proceedings, (Dec. 2011) vol. 86, No. 12, pp. 1188-1191.
Toyonaga, "Blockade of constitutively activated Janus kinase/signal transducer and activator of transcription-3 pathway inhibits growth of human pancreatic cancer", Cancer Lett. 201(1):107-16 (2003).
Trikha et al., "Targeted anti-interleukin-6 monoclonal antibody therapy for cancer: a review of the rationale and clinical evidence," Clinical Cancer Research, 2003, 9: 4653-4665.
Vanhoutte, Arthritis Rheum 64.10 (2012): S1051-1.
Vannucchi A. et al., "The mTOR Inhibitor, RAD001, Inhibits the Growth of Cells From Patients with Myeloproliferative Neoplasms", Blood: ASH Annual Meeting Absracts, $51^{st}$ Annual Meeting of the American Society of Hematology, vol. 114, No. 22 (2009) 2 pages.
Vannucchi, A. et al., "Inhibitorsof PI3K/Akt and/or mTOR Inhibit the Growth of Cells of Myeloproliferative Neoplasms and Synergize with JAK2 Inhibitor and Interferon", Blood, vol. 118, No. 21, pp. 1638-1639, XP008150742ASH Annual Meeting Abstract 3835 American Society of Hematology (2011).
Vannucchi, A. et al., "RAD001, An Inhibitor of mTOR, Shows Clinical Activity in a Phase I/II Study in Patients with Primary Myelofibrosis (PMF) and Post Polycythemia Vera/Essential Thrombocythemia Myelofibrosis (PPV/PET MF)", Blood, ASH Annual Meeting Abstracts 307, vol. 114, No. 22 (2009) 2 pages.
Vardiman et al., "The 2008 revision of the World Health Organization (WHO) classification of myeloid neoplasms and acute leukemia: rationale and important changes," Blood, Jul. 2009, 114(5): 937-51.
Vardiman et al., "The World Health Organization (WHO) classification of the myeloid neoplasms," Blood, Oct. 2002, 100(7): 2292-302.
Verma, et al., "Jak family of kinases in cancer", Cancer and Metastasis Reviews, vol. 22, No. 4, 423-434, DOI: 10.1023/A:1023805715476 (2003).

Verstovsek, "Therapeutic Potential of JAK2 Inhibitors", Hematology Am Soc Hematol Educ Program, 2009:636-42.
Verstovsek, et al., Blood (ASH Annual Meeting Abstracts) 2007 110: Abstract 558.
Verstovsek, et al., Blood (ASH Annual Meeting Abstracts) 2009 114: Abstract 311.
Verstovsek, et al., Blood (ASH Annual Meeting Abstracts) 2010 116: Abstract 313.
Verstovsek, S. et al. "The JAK Inhibitor INCB018424 Demonstrates Durable and Marked Clinical Responses in Primary Myelofibrosis (PMF) and Post-Polycythemia/Essential Thrombocythemia Myelofibrosis (Post-PV/ET-MF)" Poster #1762 at the American Society of Hematology Annual Meeting (ASH), Dec. 6, 2008 (19 pages).
Verstovsek, S. et al. "The selective Janus kinase (JAK) inhibitor, INCB018424, shows efficacy in phase I/II trial in patients with primary myelofibrosis (PMF) and post polycythemia vera/essential thrombocythemia myelofibrosis (Post-PV/ET MF)" Abstract #0444, presented Saturday, Jun. 14, 2008 at the European Hematology Association, 13th Congress, Jun. 12-15, Copenhagen, Denmark (2 pages).
Verstovsek, S. et al. INCB18424, an Oral, Selective JAK2 Inhibitor, Shows Significant Clinical Activity in a Phase I/II Study in Patient with Primary Myelofibrosis (PMF) and Post Polycythemia Vera/Essential Thrombocythemia Myelofibrosis (Post-PV/ET MF), presentation at the American Society of Hematology 49th Annual Meeting and Exposition, Dec. 10, 2007 (16 pages).
Verstovsek, Srdan et al., "Characterization of JAKS V617F Allele Burden in Advanced Myelofibrosis (MF) Patients: No Change in V617F:WT JAK2 Ratio in Patients with High Allele Burdens despite Profound Clinical Improvement Following Treatment with the JAKL Inhibitor, INCB018424," 50th ASH Annual Meeting and Exposition, Abstract No. 2802 (2008).
Wagh et al., "Polymers used in ocular dosage form and drug delivery systems," Asian J. Pharma, 12-17.
Williams, et al. "Initial Efficacy of INCB018424, a selective Janus Kinase1& 2 (JAK1&2) Inhibitor in Rheumatoid Arthritis (RA)," European League Against Rheumatism (EULAR) meeting presentation and abstract (Jun. 11-14, 2008, Paris, France). Annals Rheum Dis 67SII:62, 2008.
Xiaoyang et al., "Knockdown of STAT3 Expression by RNA Interference Inhibits the Induction of Breast Tumors in Immunocompetent Mice", Cancer Res Apr. 1, 2005 65; 2532.
Xiong, "Inhibition of JAK1, 2/STAT3 Signaling Induces Apoptosis, Cell Cycle Arrest, and Reduces Tumor Cell Invasion in Colorectal Cancer Cells," Neoplasia, Mar. 2008, 10(3): 287-297.
Yamamura et al., "Circulating interleukin-6 levels are elevated in adult T-cell leukaemia/lymphoma patients and correlate with adverse clinical features and survival," Br. J. Haematol., 1998, 100: 129-134.
Yamaoka et al., "Janus kinase (JAK) inhibitors in rheumatoid arthritis", Current Rheumatology Reviews, (Nov. 2011) vol. 7, No. 4, pp. 306-312.
Yang et al., "Constitutive NF-kB activation confers interleukin 6 (IL6) independence and resistance to dexamethasone and Janus kinase inhibitor INCB018424 in murine plasmacytoma cells", Journal of Biological Chemistiy, (Aug. 12, 2011) vol. 286, No. 32, pp. 27988-27997.
Yao, et al. "Glucocorticoid-Induced Bone Loss in Mice Can Be Reversed by the Actions of Parathyroid Hormone and Risedronate on Different Pathways for Bone Formation and Mineralization", Arthritis and Rheumatism, 58(11):3485-3497 (2008).
Yao, et al., "Glucocorticoid Excess in Mice Results in Early Activation of Osteoclastogenesis and Adipogenesis and Prolonged Suppression of Osteogenesis", Arthritis and Rheumatism, 58(6), 1674-1686 (2008).
Yongjun et al., "Advances in research of tyrosine kinases inhibitor of vascular endothelial growth factor receptor," Chinese J New Drugs, Dec. 31, 2008, 17(7):544-550.
Younes et al., "Phase I Study of a Novel Oral Janus Kinase 2 Inhibitor, SB1518, in Patients With Relapsed Lymphoma: Evidence of Clinical and Biologic Activity in Multiple Lymphoma Subtypes," Journal of Clinical Oncology, Nov. 2012, 30(33): 4161-4167.

(56) References Cited

OTHER PUBLICATIONS

Yu, et al., "Constitutive activation of the Janus kinase-STAT pathway in T lymphoma overexpressing the Lck protein tyrosine kinase", J Immunol, 159(11):5206-10 (1997).
Zheng, et al., "Discovery of INCB108201PF-4178903, a potent, selective, and orally bioavailable dual CCR2 and CCR5 antagonist", Bioorganic & Medicinal Chemistry Letters 21 (2011) 1442-45.
Zou, et al., "Signaling Pathways Activated by Oncogenic Forms of Abl Tyrosine Kinase." Journal of Biological Chemistiy, 274(26):18141-18144, 1999.
Argentina Office Action in Argentina Application No. 20140101971, dated Nov. 22, 2019, 6 pages.
Australian Office Action in Australian Application No. 2018223058, dated Dec. 17, 2019, 4 pages.
Australian Office Action in Australian Application No. 2018223058, dated Apr. 8, 2019, 4 pages.
Costa Rican Office Action in Costa Rican Application No. 2015-0633, dated Sep. 20, 2019, 14 pages.
Costa Rican Office Action in Costa Rican Application No. 2015-0633, dated Feb. 25, 2020, 13 pages.
Eurasian Office Action in Eurasian Application No. 201592199, dated Feb. 4, 2019, 7 pages.
European Search Report in European Application No. 18215671.1, dated May 14, 2019, 5 pages.
Indian Office Action in Indian Application No. 11174/DELNP/2015, dated Nov. 19, 2019, 8 pages.
Japanese Office Action in Japanese Application No. 2016-514126, dated Feb. 27, 2018, 5 pages (English Translation).
Japanese Office Action in Japanese Application No. 2018-187613, dated Jan. 7, 2020, 4 pages.
Peruvian Office Action in Peruvian Application No. 2406-2015, dated Sep. 26, 2019, 17 pages.
Mexican Office Action in Mexican Application No. MX/a/2015/015738, dated Aug. 6, 2019, 5 pages.
Vietnamese Office Action in Vietnamese Application No. 11-2019-01578, dated Apr. 26, 2019, 2 pages.
Search Report ID SR-20210895.01, "Single Crystal Structure Determination of INCB054707 Phosphate," dated May 20, 2021, 42 pages.
Coligan et al., "Current Protocols in Immunology," Wiley Press, vol. 3, 21 pages (Chapter Abstracts Only).
Winyard and Willoughby, "Methods in Molecular Biology Inflammation Protocols," Humana Press, 2003, vol. 225, 359 pages.

PROCESSES OF PREPARING A JAK1 INHIBITOR

PRIORITY CLAIM

This application claims priority to U.S. Provisional Patent Application No. 63/033,618, filed on Jun. 2, 2020, the entirety of which is incorporated by reference herein.

TECHNICAL FIELD

The present application provides processes for preparing 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, and phosphoric acid salt thereof, which is useful as a selective (Janus kinase 1) JAK1 inhibitor, as well as salt forms and intermediates related thereto.

BACKGROUND

Protein kinases (PKs) regulate diverse biological processes including cell growth, survival, differentiation, organ formation, morphogenesis, neovascularization, tissue repair, and regeneration, among others. Protein kinases also play specialized roles in a host of human diseases including cancer. Cytokines, low-molecular weight polypeptides or glycoproteins, regulate many pathways involved in the host inflammatory response to sepsis. Cytokines influence cell differentiation, proliferation and activation, and can modulate both pro-inflammatory and anti-inflammatory responses to allow the host to react appropriately to pathogens. Signaling of a wide range of cytokines involves the Janus kinase family (JAKs) of protein tyrosine kinases and Signal Transducers and Activators of Transcription (STATs). There are four known mammalian JAKs: JAK1 (Janus kinase-1), JAK2, JAK3 (also known as Janus kinase, leukocyte; JAKL; and L-JAK), and TYK2 (protein-tyrosine kinase 2).

Cytokine-stimulated immune and inflammatory responses contribute to pathogenesis of diseases: pathologies such as severe combined immunodeficiency (SCID) arise from suppression of the immune system, while a hyperactive or inappropriate immune/inflammatory response contributes to the pathology of autoimmune diseases (e.g., asthma, systemic lupus erythematosus, thyroiditis, myocarditis), and illnesses such as scleroderma and osteoarthritis (Ortmann, R. A., T. Cheng, et al. (2000) *Arthritis Res* 2(1): 16-32).

Deficiencies in expression of JAKs are associated with many disease states. For example, Jak1–/– mice are runted at birth, fail to nurse, and die perinatally (Rodig, S. J., M. A. Meraz, et al. (1998) *Cell* 93(3): 373-83). Jak2–/– mouse embryos are anemic and die around day 12.5 postcoitum due to the absence of definitive erythropoiesis.

The JAK/STAT pathway, and in particular all four JAKs, are believed to play a role in the pathogenesis of asthmatic response, chronic obstructive pulmonary disease, bronchitis, and other related inflammatory diseases of the lower respiratory tract. Multiple cytokines that signal through JAKs have been linked to inflammatory diseases/conditions of the upper respiratory tract, such as those affecting the nose and sinuses (e.g., rhinitis and sinusitis) whether classically allergic reactions or not. The JAK/STAT pathway has also been implicated in inflammatory diseases/conditions of the eye and chronic allergic responses.

Activation of JAK/STAT in cancers may occur by cytokine stimulation (e.g. IL-6 or GM-CSF) or by a reduction in the endogenous suppressors of JAK signaling such as SOCS (suppressor or cytokine signaling) or PIAS (protein inhibitor of activated STAT) (Boudny, V., and Kovarik, J., *Neoplasm.* 49:349-355, 2002). Activation of STAT signaling, as well as other pathways downstream of JAKs (e.g., Akt), has been correlated with poor prognosis in many cancer types (Bowman, T., et al. *Oncogene* 19:2474-2488, 2000). Elevated levels of circulating cytokines that signal through JAK/STAT play a causal role in cachexia and/or chronic fatigue. As such, JAK inhibition may be beneficial to cancer patients for reasons that extend beyond potential anti-tumor activity.

JAK2 tyrosine kinase can be beneficial for patients with myeloproliferative disorders, e.g., polycythemia vera (PV), essential thrombocythemia (ET), myeloid metaplasia with myelofibrosis (MMM) (Levin, et al., *Cancer Cell*, vol. 7, 2005: 387-397). Inhibition of the JAK2V617F kinase decreases proliferation of hematopoietic cells, suggesting JAK2 as a potential target for pharmacologic inhibition in patients with PV, ET, and MMM.

Inhibition of the JAKs may benefit patients suffering from skin immune disorders such as psoriasis, and skin sensitization. The maintenance of psoriasis is believed to depend on a number of inflammatory cytokines in addition to various chemokines and growth factors (JCI, 113:1664-1675), many of which signal through JAKs (*Adv Pharmacol.* 2000;47:113-74).

Thus, new or improved agents which inhibit kinases such as JAKs are continually needed for developing new and more effective pharmaceuticals that are aimed at augmentation or suppression of the immune and inflammatory pathways (such as immunosuppressive agents for organ transplants), as well as agents for the prevention and treatment of autoimmune diseases, diseases involving a hyperactive inflammatory response (e.g., eczema), allergies, cancer (e.g., prostate, leukemia, multiple myeloma), and some immune reactions (e.g., skin rash or contact dermatitis or diarrhea) caused by other therapeutics. Inhibitors of JAKs are in current development. While there are JAK inhibitors and processes of preparing them in the literature, there remains a need for new processes of preparing these inhibitors having suitable properties useful in the manufacture of sale, effective, high quality drug product. The present disclosure described herein is directed toward this end.

SUMMARY

The present disclosure provides processes of preparing a selective JAK1 inhibitor, 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide, or salt forms thereof, including 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt, and intermediate compounds related thereto.

DETAILED DESCRIPTION

Figure 1:
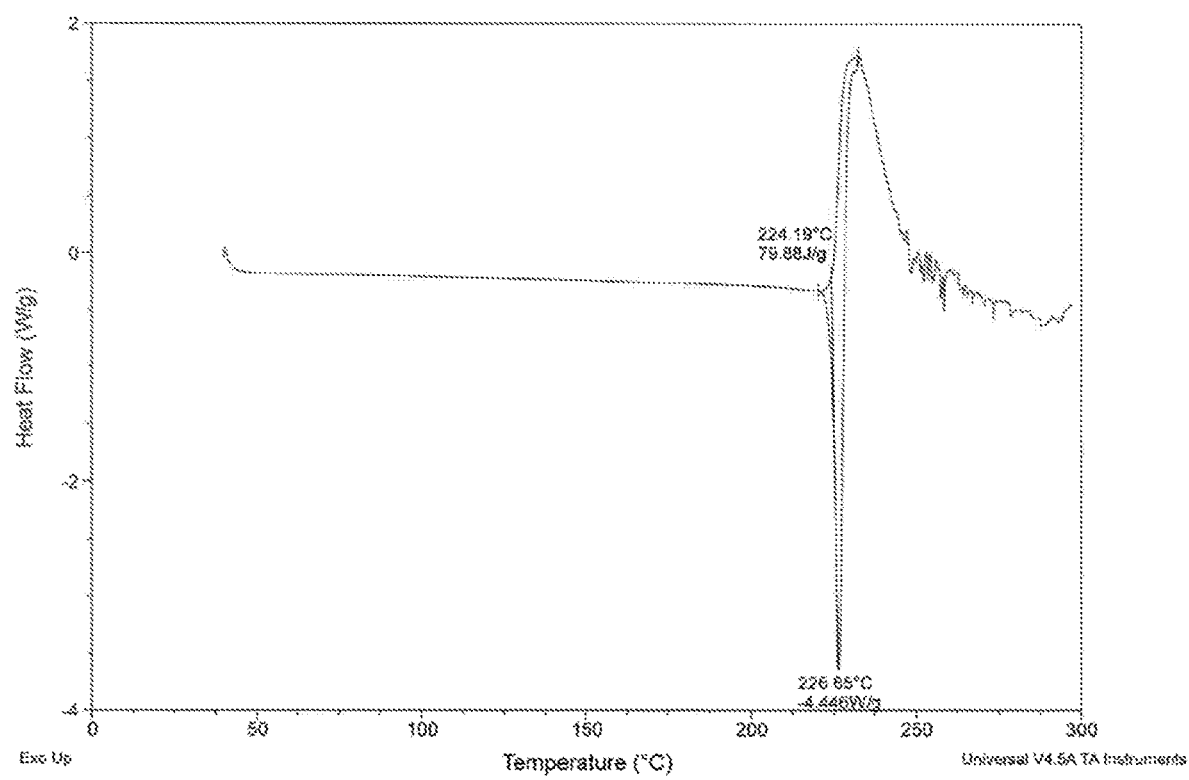
FIG. 1. shows a representative differential scanning calorimetry (DSC) trace for Compound 1 phosphoric acid, prepared according to the process described in Example 1.

The present disclosure provides processes of preparing a selective JAK1 inhibitor, 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (see below), referred to herein as "Compound 1". The free base of the compound is shown below.

Compound 1

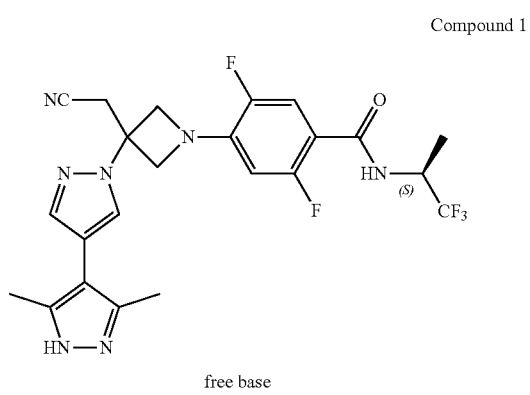

free base

The present disclosure also provides a process of preparing the phosphoric acid salt of Compound 1 free base (see below), 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt, referred to herein as "Compound 1 phosphoric acid salt", "Compound 1 phosphate", or "Compound 1 phosphate salt".

Compound 1

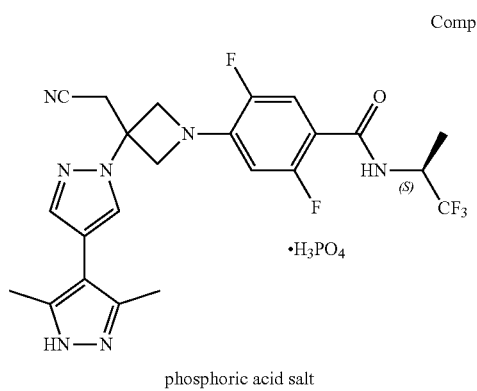

phosphoric acid salt

An exemplary process of preparing Compound 1 and its phosphoric acid salt is disclosed in US2014/0343030, which is incorporated herein by reference in its entirety. The processes of preparing Compound 1 free base and its phosphoric acid salt provided herein have several advantages over the process disclosed in US2014/0343030, making the processes provided herein more suitable for scale up manufacturing processes. For example, an exemplary process described herein is a convergent synthesis that provides high yields, increasing the efficacy of a multi-step synthesis as compared to the linear synthesis in US2014/0343030. The yields of the intermediate products such as those shown in Scheme 2 (vide infra) range from about 93% to about 94% on a scale ranging from about 670 gram to about 2000 gram. In addition, the yields of Compound 1 free base and its phosphoric acid salt as shown in Scheme 5 (vide infra) range from about 90% to about 97% on a scale ranging from 430 gram to about 5800 gram. The overall yield of the process provided herein starting from the preparation of (S)-2,4,5-trifluoro-N-[1,1,1-trifluoropropan-2-yl]benzamide (Compound 1a, Scheme 2, vide infra) to Compound 1 free base is about 68% to about 70% in a five-step synthesis, while the overall yield using the process in US2014/0343030 is less than 5%, requiring six steps starting from the preparation of (S)-2,4,5-trifluoro-N-[1,1,1-trifluoropropan-2-yl]benzamide to Compound 1 free base.

The processes disclosed herein afford good product purity and high yields on a large scale. For example, in US2014/0343030 the Suzuki coupling reaction of 4-{3-(cyanomethyl)-3-[4-(4,4,5,5-tetramethyl-1,3,2-dioxaborolan-2-yl)-1H-pyrazol-1-yl]azetidin-1-yl}-2,5-difluoro-N-[(1S)-2,2,2-trifluoro-1-methylethyl]benzamide with 4-bromo-3,5-dimethyl-1H-pyrazole in the presence of a palladium catalyst to generate Compound 1 free base results in low yield (less than about 10% yield, Example 7) and requires removal of the palladium contaminants from the product. In an exemplary process provided herein, the Suzuki coupling step involving a palladium catalyst is performed in a separate parallel synthesis to generate a bipyrazole compound (Compound 2x, Scheme 1, vide infra), which is then coupled with (S)-4-(3-(cyanomethylene)azetidin-1-yl)-2,5-difluoro-N-(1,1,1-trifluoropropan-2-yl)benzamide to generate Compound 1 free base (Scheme 5, vide infra). Compound 2x can be readily purified as the highly crystalline HCl salt. The crystallization process allows Compound 2x to be more easily purified to remove palladium impurities than the complex multi-nitrogen containing Compound 1 free base. This represents an advantage over the prior process which necessitated a low yield column chromatography separation. Further, the placement of the palladium coupling step earlier in the synthetic process improved the overall yield.

In addition, use of the bipyrazole compound (Compound 2x) in a Michael addition reaction with Compound 1x unexpectedly resulted in a high degree of regioselectivity. In some embodiments, the regioselectivity was about 20:1 or greater in favor of the desired regioisomer, Compound 1 free base, over the undesired regioisomer (Compound R show below). Based on electronic effects, the Compound R regioisomer was the expected product, because the two electron-donating methyl groups make the 1H-NH group of Compound 2x more nucleophilic than the 1'H-NH group. Without being limited to a particular theory, it is believed that the steric hindrance at the 1H-NH group results in the unexpectedly high degree of regioselectivity.

Compound 1

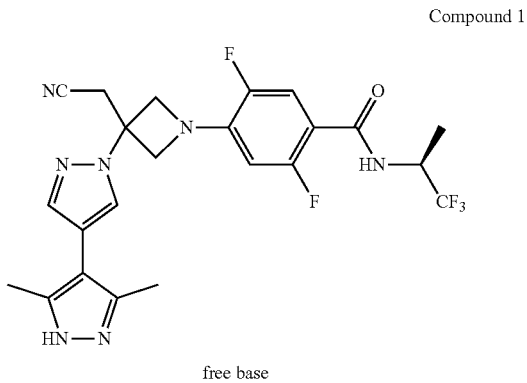

free base

-continued

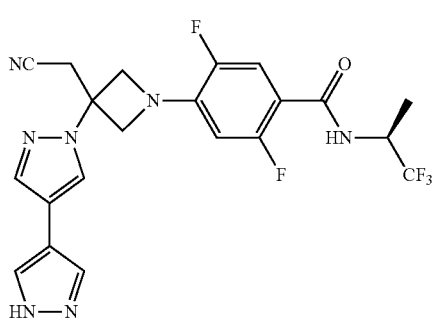
Compound R

In some embodiments, the present disclosure relates to a process of preparing

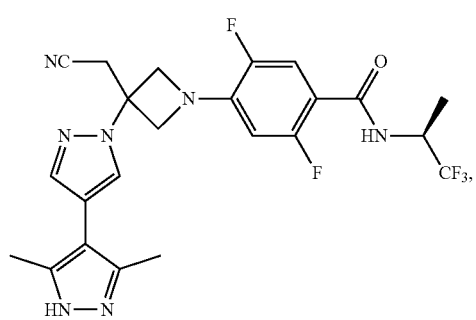
(Compound 1 free base)

or a salt thereof, comprising reacting

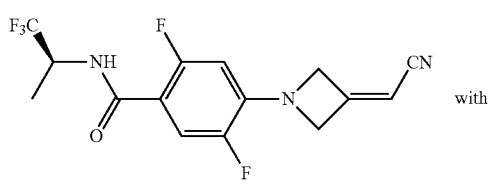
(Compound 1x)

with

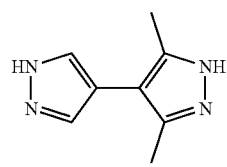
(Compound 2x)

to form Compound 1 free base, or a salt thereof.

In some embodiments, the reacting of Compound 1x with Compound 2x is carried out in the presence of 1,8-diazabicyclo[5.4.0]undec-7-ene (DBU) and an organic solvent component. In some embodiments, the organic solvent component comprises dimethylformamide (DMF).

In some embodiments, the reacting of Compound 1x with Compound 2x is carried out at a temperature from about 40° C. to about 70° C., about 45° C. to about 65° C., or about 50° C. to about 60° C. In some embodiments, the temperature is from about 50° C. to about 60° C. For example, the temperature is about 60° C.

In some embodiments, the process of preparing Compound 1 free base further comprises a work up after the reaction is completed. For example, the work up can comprise adding water to the reaction mixture and collecting the solid of Compound 1 free base by filtration, which can be washed with water.

In some embodiments, the present disclosure provides a process of preparing Compound 1 phosphoric acid salt comprising reacting Compound 1 free base prepared by a process described herein with phosphoric acid. In some embodiments, the salt of Compound 1 is a phosphoric acid salt of Compound 1 which is prepared by a process comprising reacting Compound 1 free base with phosphoric acid.

In some embodiments, the reacting of Compound 1 free base with phosphoric acid is carried out in the presence of solvent component. In some embodiments, the solvent component comprises methanol, isopropanol, or a mixture thereof.

In some embodiments, the reacting of Compound 1 free base with phosphoric acid is carried out at a temperature from about 40° C. to about 70° C. or from about 45° C. to about 55° C. For example, the temperature is about 50° C.

In some embodiments, the phosphoric acid is an aqueous solution of about 85 wt % phosphoric acid. In some embodiments, the reacting of Compound 1 free base with phosphoric acid further comprises adding a second solvent component to the reaction mixture. For example, the second solvent component comprises n-heptane.

The present disclosure also provides a process of preparing the intermediate compounds e.g.,

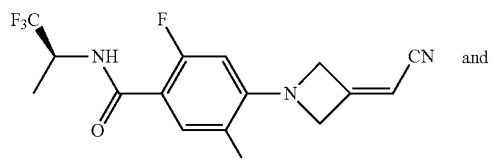
(Compound 1x) and

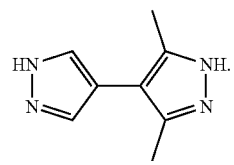
(Compound 2x)

In some embodiments, the present disclosure provides a process of preparing

Compound 1x comprising:

1a) reacting

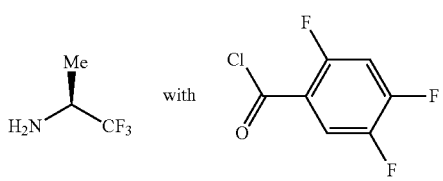 [SMILES: C[C@H](N)C(F)(F)F ; O=C(Cl)c1cc(F)c(F)cc1F] with 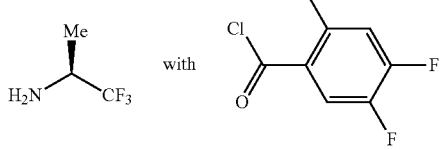

in the presence of a base to form

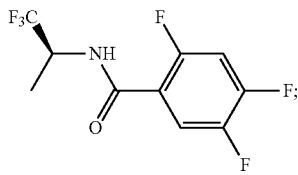
(Compound 1a)

2a) reacting Compound 1a with

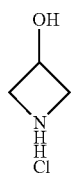

in the presence of DBU to form

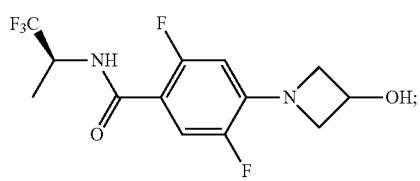
(Compound 1b)

3a) reacting Compound 1b with iodobenzene diacetate and TEMPO to form

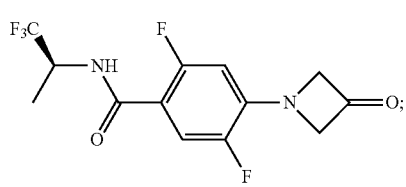
(Compound 1c)

and 4a) reacting Compound 1c with diethyl cyanomethylphosphonate in the presence of a base to form Compound 1x.

In operation 1a, (2S)-1,1,1-trifluoropropan-2-amine can be reacted with 2,4,5-trifluorobenzoyl chloride in the presence of a base to form Compound 1a. In some embodiments, the base is N,N-diisopropylethylamine or aqueous sodium hydroxide solution. In some embodiments, the base is aqueous sodium hydroxide. In some embodiments, the reacting is carried out in the presence of an organic solvent component (e.g., toluene). In some embodiments, the reacting is carried out at a temperature from about 0° C. to about 10° C. or about 0° C. to about 5° C. In some embodiments, a salt of (2S)-1,1,1-trifluoropropan-2-amine (e.g., an HCl salt) is converted to its free base before reaction with

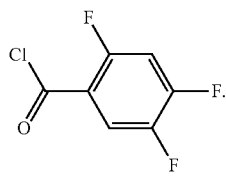 [SMILES: O=C(Cl)c1cc(F)c(F)cc1F]

For example, in some embodiments, the (2S)-1,1,1-trifluoropropan-2-amine salt (e.g., an HCl salt) is converted to its free base in-situ. In some embodiments, operation 1a further comprises a work up to obtain Compound 1a after the reaction is deemed complete, e.g., by HPLC. For example, the work up can comprise separating the phases of the reaction mixture and washing the organic phase with e.g., a 0.5 M aqueous sodium hydroxide solution. In some embodiments, the solid of Compound 1a can be slurred in n-heptane at about 50° C. for about 1 h. The solids can be collected by filtration and washed with n-heptane.

In operation 2a, Compound 1a can be reacted with azetidin-3-ol hydrochloride in the presence of 1,8-diazabicyclo[5.4.0]undec-7-ene (DBU) to form Compound 1b. In some embodiments, the reacting is carried out in an organic solvent component, which includes e.g., acetonitrile. In some embodiments, DBU can be added to the reaction mixture of Compound 1a and azetidin-3-ol hydrochloride in portions. In some embodiments, the reacting is carried out at a temperature from about 50° C. to about 75° C. or about 55° C. to about 70° C. For example, the temperature is about 58° C. to about 68° C. In some embodiment, operation 2a further comprises a work-up to obtain Compound 1b after the reaction is deemed complete, e.g., by HPLC. The work-up can comprise adding 1.0 M aqueous hydrochloric acid solution to the mixture of Compound 1a with azetidin-3-ol hydrochloride and DBU, stirring the mixture with the hydrochloric acid solution at ambient temperature, adding water to the stirred mixture, and stirring the mixture that has been added the water. The work-up can further comprise isolating the solid of Compound 1b and rinsing the solid with water.

In operation 3a, Compound 1b can be reacted with iodobenzene diacetate and 2,2,6,6-tetramethyl-1-piperidinyloxy free radical (TEMPO) to form Compound 1c. In some embodiments, the reacting is carried out in an organic solvent component, which includes e.g., methylene chloride. In some embodiments, the reacting is carried out at a temperature from about 0° C. to about 20° C. or about 5° C. to about 15° C. For example, the temperature is about 10° C. to about 12° C. In some embodiments, operation 3a further comprises a work up to obtain Compound 1c after the reaction is deemed complete, e.g., by HPLC. The work up can comprise quenching the reaction with an aqueous solution of sodium thiosulfate and potassium phosphate. Two phases can be separated and the organic phase can be washed with water. The organic solution can be concentrated under reduced pressure to afford Compound 1c as a solid. The solid of Compound 1c can be reslurried in n-heptane at room temperature for about 30 minutes and washed with n-heptane.

In operation 4a, Compound 1c can be reacted with diethyl cyanomethylphosphonate in the presence of a base to form Compound 1x. The base includes e.g., potassium tert-butoxide. In some embodiments, the reacting is carried out in the presence of an organic solvent component, which includes e.g., THF, ethanol, or mixture thereof. In some embodiments, diethyl cyanomethylphosphonate can be added to a solution of 1.0 M potassium tert-butoxide in THF at about 5° C. to about 25° C. In some embodiments, the molar equivalents of potassium tert-butoxide solution in THF to Compound 1c is about 0.95. In some embodiments, the molar equivalents of potassium tert-butoxide solution in THF to Compound 1c is less than about 0.95 (e.g., about 0.94, about 0.93, about 0.92, about 0.91, or about 0.90). In some embodiments, Compound 1c can be dissolved in a mixture of organic solvent components (e.g., ethanol and tetrahydrofuran). In some embodiments, the diethyl cyanomethylphosphonate and 1.0 M potassium tert-butoxide mixture can be added to the mixture containing Compound 1c. In some embodiments, operation 4a further comprises a work up to obtain Compound 1x after the reaction is deemed complete, e.g., by HPLC. The work up can comprise adding water to the reaction mixture. The solid can be collected by filtration and washed with water and n-heptane. In some embodiment, the solid can further be reslurried in methyl tent-butyl ether, collected by filtration, and washed with MTBE.

In some embodiments, the process of preparing Compound 1 free base, or a salt thereof, further comprises preparing Compound 1x wherein Compound 1x can be prepared by a process comprising reacting Compound 1c with diethyl cyanomethylphosphonate in the presence of a base. In some embodiments, the process further comprises preparing Compound 1c wherein Compound 1c can be prepared by a process comprising reacting Compound 1b with iodobenzene diacetate and TEMPO. In some embodiments, the process further comprises preparing Compound 1b wherein Compound 1b can be prepared by a process comprising reacting Compound 1a with azetidin-3-ol hydrochloride in the presence of DBU. In some embodiments, the process further comprises preparing Compound 1a wherein Compound 1a can be prepared by a process comprising reacting (2S)-1,1,1-trifluoropropan-2-amine with 2,4,5-trifluorobenzoyl chloride in the presence of a base.

In some embodiments, the present disclosure provides a process of preparing Compound 2x comprising:

1b) reacting

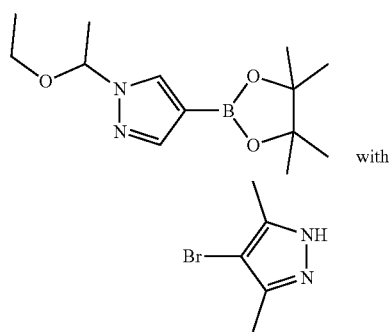
(Compound 2a)

with

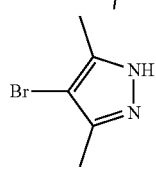

to form

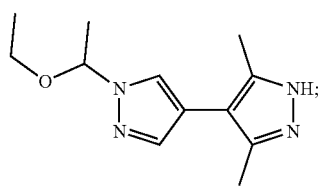
(Compound 2b)

2b) reacting Compound 2b with hydrochloric acid to form

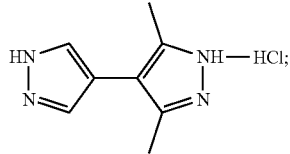
(Compound 2x HCl)

and 3b) reacting Compound 2x HCl with a base to form Compound 2x.

In operation 1b, Compound 2a can be reacted with 4-bromo-3,5-dimethylpyrazole to form Compound 2b. In some embodiments, the reacting is carried out in the presence of $K_2HPO_4$, a solvent component, and a palladium complex. For example, the solvent component comprises 1-propanol, water, or a mixture thereof. In some embodiments, the palladium complex is [1,1'-bis(di-tert-butylphosphino)ferrocene]dichloropalladium(II) (Pd-118). In some embodiments, the reacting is carried out at a temperature from about 80° C. to about 100° C. or about 90° C. to about 100° C. For example, the temperature is about 90° C. In some embodiments, operation 1b further comprises a work up to obtain Compound 2a. The work up can comprise cooling the reaction mixture to about 17° C. and separating the phases. The organic phase can be mixed with activated charcoal, heated to about 70° C., stirred for about 4 hours, and cooled to about 21° C. The mixture comprising Compound 2a can be filtered through Celite. In some embodiments, operation 1b further comprises mixing the crude Compound 2a with ethyl acetate and an aqueous $NaHSO_3$ solution, where the resulting mixture is heated to about 65° C. to about 70° C. for about 2.5 h. The phases can be separated and the organic phase can be mixed with an aqueous $NaHSO_3$ solution, where the resulting mixture is heated to about 65° C. to about 70° C. for about 3.5 h. The phases can be separated and the phase comprising Compound 2a can be purified by column chromatography using ethyl acetate as the eluent. In some embodiments, purified Compound 2a is further mixed with methylene chloride and Si-thiol, where the resulting mixture is filtered.

In operation 2b, Compound 2b can be reacted with hydrochloric acid to form Compound 2x HCl. In some embodiments, the reacting is carried out in the presence of organic solvent component. For example, the organic solvent component comprises 2-propanol. In some embodiments, the reacting of Compound 2b with hydrochloric acid is carried out at a temperature from about 50° C. to about 75° C. or about 55° C. to about 70° C. For example, the temperature is about 60° C. to about 65° C. In some embodiments, operation 2b further comprises a work up to obtain Compound 2b after the reaction is deemed complete, e.g., by HPLC. For example, the reaction mixture is cooled to room temperature and stirred for about 1 h. The solid of Compound 2b can be collected by filtration and washed with 2-propanol.

In operation 3b, Compound 2x HCl can be reacted with a base to form Compound 2x. The present disclosure also relates to a process of preparing Compound 2x comprising reacting Compound 2x HCl with a base. Exemplary bases include KOH, LiOH, $K_2CO_3$, $Na_2CO_3$, and other bases that can neutralize Compound 2x HCl to its free base. In some embodiments, the base is NaOH. In some embodiment, the reacting of Compound 2x HCl with a base is carried out at a temperature from about 10° C. to about 20° C. or about 15° C. to about 20° C. For example, the temperature is from about 15° C. to about 18° C. In some embodiments, operation 3b further comprises a work up to obtain Compound 2x after the reaction is complete. For example, the solid of Compound 2x can be collected by filtration and washed with water and n-heptane.

In some embodiments, the process of preparing Compound 1 free base, or a salt thereof, further comprises preparing Compound 2x wherein Compound 2x can be prepared by a process comprising reacting Compound 2x HCl with a base. In some embodiments, the process further comprises preparing Compound 2x HCl wherein Compound 2x HCl is prepared by a process comprising reacting Compound 2b with hydrochloric acid. In some embodiments, the process further comprises preparing Compound 2b wherein Compound 2b is prepared by a process comprising reacting Compound 2a with 4-bromo-3,5-dimethylpyrazole.

In some embodiments, the present application further provides a process of preparing a compound of Formula A:

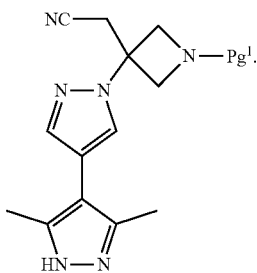

In some embodiments, the process of preparing the compound of Formula A comprises reacting 3,5-dimethyl-1H,1'H-4,4'-bipyrazole with a compound of Formula B:

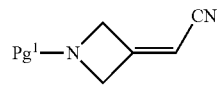

wherein Pg$^1$ is an amine protecting group. In some embodiments, Pg$^1$ is tert-butoxycarbonyl.

In some embodiments, the reacting of 3,5-dimethyl-1H, 1'H-4,4'-bipyrazole with a compound of Formula B is performed in the presence of 1,8-diazabicyclo[5.4.0]undec-7-ene.

In some embodiments, less than 1 equivalent of the 1,8-diazabicyclo[5.4.0]undec-7-ene is used based on 1 equivalent of the compound of Formula B.

In some embodiments, about 0.2 to about 0.3 equivalents of the 1,8-diazabicyclo[5.4.0]undec-7-ene is used based on 1 equivalent of the compound of Formula B.

In some embodiments, greater than about 1 equivalent of the 3,5-dimethyl-1H,1'H-4,4'-bipyrazole is used based on 1 equivalent of the compound of Formula B.

In some embodiments, about 1.0 to about 2.0 equivalents of the 3,5-dimethyl-1H,1'H-4,4'-bipyrazole is used based on 1 equivalent of the compound of Formula B.

In some embodiments, about 1.0 to about 1.1 equivalents of the 3,5-dimethyl-1H,1'H-4,4'-bipyrazole is used based on 1 equivalent of the compound of Formula B.

In some embodiments, about 1.0 to about 1.1 equivalents of the 3,5-dimethyl-1H,1'H-4,4'-bipyrazole is used based on 1 equivalent of the compound of Formula B.

In some embodiments, the reacting of 3,5-dimethyl-1H, 1'H-4,4'-bipyrazole with a compound of Formula B is performed at about room temperature.

In some embodiments, the reaction of 3,5-dimethyl-1H, 1'H-4,4'-bipyrazole with the compound of Formula B is performed in the presence of a solvent component. In some embodiments, the solvent component comprises dimethyl sulfoxide. In some embodiments, the solvent component comprises dimethyl sulfoxide and methylene chloride.

In some embodiments, the process provided herein further comprises deprotecting the compound of Formula A to form a compound of Formula C:

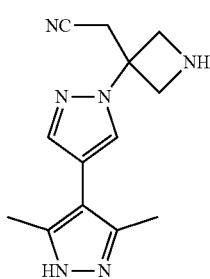

or a salt thereof.

In some embodiments, the deprotecting of the compound of Formula A comprises reacting the compound of Formula A in the presence of a strong acid (e.g., hydrochloric acid).

In some embodiments, the deprotecting of the compound of Formula A comprises reacting the compound of Formula A in the presence of a trialkylsilyl halide.

In some embodiments, the trialkyl silyl halide is trimethylsilyl iodide.

In some embodiments, the deprotecting of the compound of Formula A is performed in the presence of a solvent component. In some embodiments, the solvent component comprises methylene chloride. In some embodiments, the solvent component comprises methylene chloride and methanol.

In some embodiments, the deprotecting of the compound of Formula A is performed at about room temperature.

In some embodiments, the process provided herein further comprises reacting the compound of Formula C, or a salt thereof, with a base, to form the free base form of the compound of Formula C.

In some embodiments, the process provided herein further comprises reacting the compound of Formula C, or a salt thereof, with an amine base, to form the free base form of the compound of Formula C.

In some embodiments, the base is a tri(C$_{1-6}$ alkyl)amine.

In some embodiments, the base is triethylamine.

In some embodiments, the reaction of the compound of Formula C, or a salt thereof, with an amine base is performed in the presence of a solvent component. In some embodiments, the solvent component comprises methylene chloride.

In some embodiments, the process provided herein further comprises reacting the free base form of the compound of Formula C with Compound 1a:

to form Compound 1:

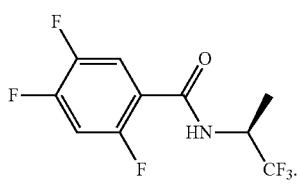

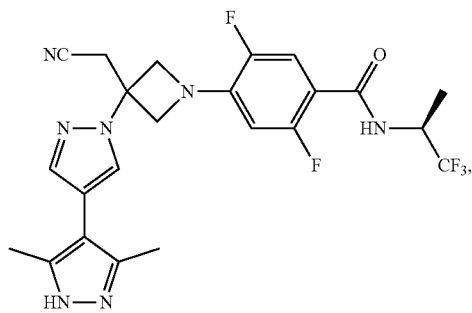 [SMILES: Cc1n[nH]c(C)c1-c1cnn(C2(CC#N)CN(c3cc(F)c(C(=O)N[C@@H](C)C(F)(F)F)cc3F)C2)c1]

or a salt thereof.

In some embodiments, the free base form of the compound of Formula C is reacted with Compound 1a in the presence of a base and an alkali metal halide to form Compound 1:

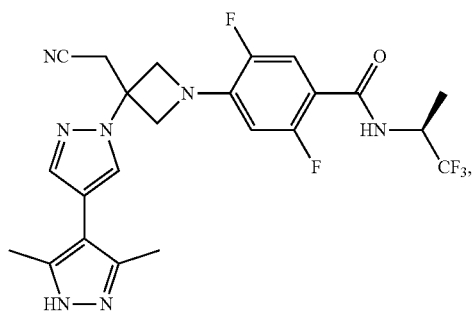 [SMILES: Cc1n[nH]c(C)c1-c1cnn(C2(CC#N)CN(c3cc(F)c(C(=O)N[C@@H](C)C(F)(F)F)cc3F)C2)c1]

or a salt thereof.

In some embodiments, the base is a bicarbonate base.

In some embodiments, the base is sodium bicarbonate.

In some embodiments, the alkali metal halide is lithium chloride.

In some embodiments, the reacting of the free base form of the compound of Formula C with Compound 1a is performed at a temperature of from about 80° C. to about 90° C.

In some embodiments, the reaction of the free base form of the compound of Formula C with Compound 1a is performed in the presence of a solvent component. In some embodiments, the solvent component comprises dimethyl sulfoxide. In some embodiments, the solvent component comprises dimethyl sulfoxide and isopropyl acetate.

In some embodiments, the process provided herein further comprises reacting Compound 1 with a strong acid to form a salt form of Compound 1.

In some embodiments, the process provided herein further comprises reacting Compound 1 with hydrochloric acid to form Compound 1 hydrochloric acid salt:

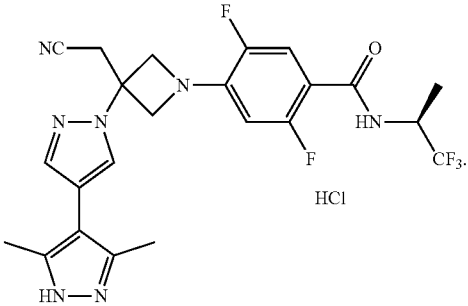 [SMILES: Cc1n[nH]c(C)c1-c1cnn(C2(CC#N)CN(c3cc(F)c(C(=O)N[C@@H](C)C(F)(F)F)cc3F)C2)c1 ; Cl]

In some embodiments, greater than 1 equivalent of hydrochloric acid is used based on 1 equivalent of Compound 1.

In some embodiments, the reaction of Compound 1 with hydrochloric acid is performed at about room temperature.

In some embodiments, the hydrochloric acid is an alcoholic hydrochloric acid solution.

In some embodiments, the hydrochloric acid is an isopropanol solution of hydrochloric acid.

In some embodiments, the process provided herein further comprises reacting the Compound 1 hydrochloric acid salt with a base to form the free base form of Compound 1:

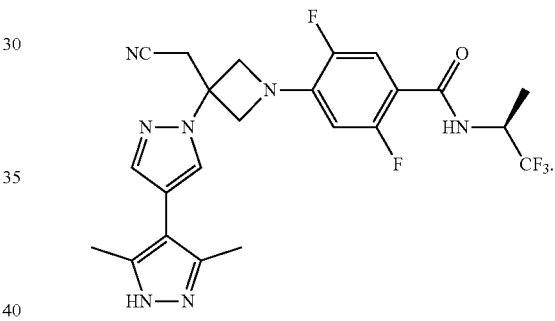

In some embodiments, the process provided herein further comprises reacting the Compound 1 hydrochloric acid salt with a bicarbonate base to form the free base form of Compound 1:

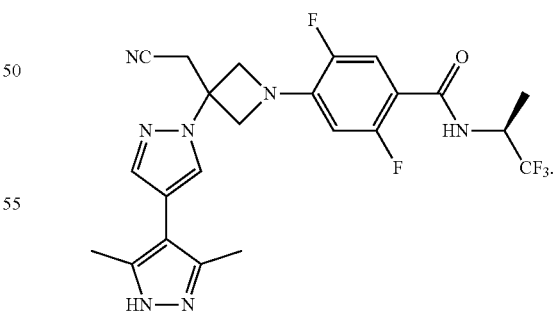

In some embodiments, the base is potassium bicarbonate.

In some embodiments, the potassium bicarbonate is an aqueous potassium bicarbonate solution.

In some embodiments, the process provided herein further comprising reacting the free base form of Compound 1 with phosphoric acid to form Compound 1 phosphoric acid salt:

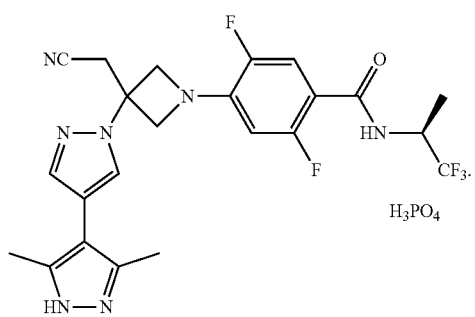

The process of claim 69, wherein the reaction of the free base form of Compound 1 with phosphoric acid is performed at about room temperature.

In some embodiments, the reaction of the free base form of Compound 1 with phosphoric acid is performed in the presence of a solvent component. In some embodiments, the solvent component comprises water. In some embodiments, the solvent component comprises water and isopropyl alcohol.

In some embodiments, the process provided herein further comprises isolating the Compound 1 phosphoric acid salt.

In some embodiments, the Compound 1 phosphoric acid salt is isolated by recrystallization.

In some embodiments, the Compound 1 phosphoric acid salt is isolated by recrystallization from a solvent component comprising methanol.

In some embodiments, the Compound 1 phosphoric acid salt is isolated by recrystallization from a solvent component comprising isopropanol.

In some embodiments, the Compound 1 phosphoric acid salt is isolated by recrystallization from a solvent component comprising methylcyclohexane.

In some embodiments, the Compound 1 phosphoric acid salt is isolated by recrystallization from a solvent component comprising one or more of methanol, isopropanol, and methylcyclohexane.

In some embodiments, the Compound 1 phosphoric acid salt is isolated by recrystallization from a solvent component comprising methanol, isopropanol, and methylcyclohexane.

In some embodiments, the Compound 1 phosphoric acid salt is isolated by recrystallization from a solvent component comprising methanol, isopropanol, and methylcyclohexane; and subsequently recrystallized from a solvent component comprising methanol and isopropanol.

In some embodiments, the present application further provides a process of preparing Compound 1 phosphoric acid salt:

Compound 1

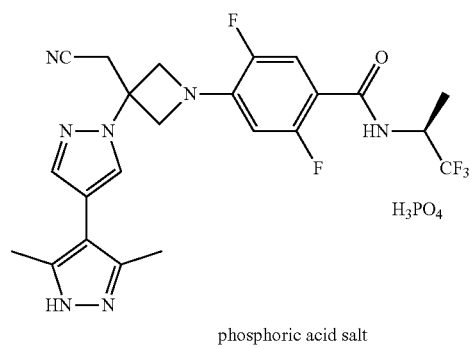

phosphoric acid salt comprising:

reacting 3,5-dimethyl-1H,1'H-4,4'-bipyrazole with tent-butyl 3-(cyanomethylene)azetidine-1-carboxylate in the presence of 1,8-diazabicyclo[5.4.0]undec-7-ene to form the compound of Formula A-1:

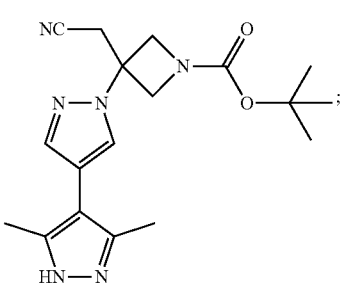

A-1 deprotecting the compound of Formula A-1 to form the compound of Formula C-1:

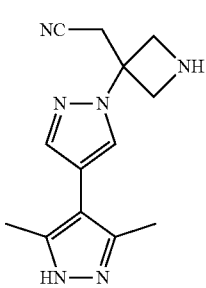

C-1 or a salt thereof;

reacting the compound of Formula C-1 with triethylamine to form the free base form of the compound of Formula C-1;

reacting the free base form of the compound of Formula C-1 with Compound 1a:

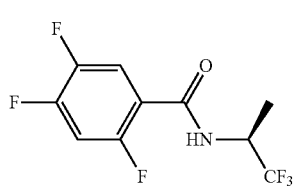

1a in the presence of sodium bicarbonate and lithium chloride to form Compound 1:

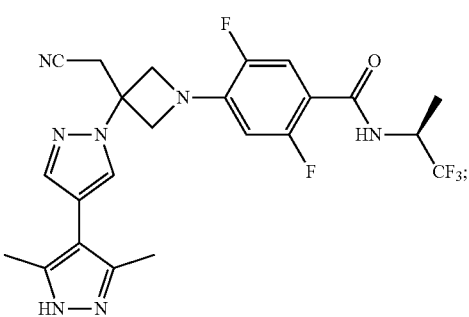 [SMILES: Cc1n[nH]c(C)c1-c1cnn(C2(CC#N)CN(c3cc(F)c(C(=O)N[C@@H](C)C(F)(F)F)cc3F)C2)c1]

reacting Compound 1 with hydrochloric acid to form Compound 1 hydrochloric acid salt:

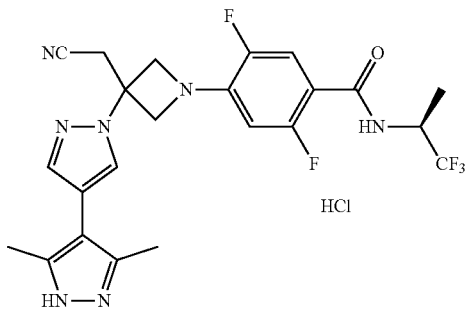 [SMILES: Cc1n[nH]c(C)c1-c1cnn(C2(CC#N)CN(c3cc(F)c(C(=O)N[C@@H](C)C(F)(F)F)cc3F)C2)c1 ; Cl]

reacting Compound 1 hydrochloric acid salt with potassium bicarbonate to form the free base form of Compound 1; and reacting the free base form of Compound 1 with phosphoric acid to form the Compound 1 phosphoric acid salt.

In some embodiments, the present disclosure provides a compound which is 3,5-dimethyl-1H,1'H-[4,4']bipyrazolyl (Compound 2x), 3,5-dimethyl-1H,1'H-4,4'-bipyrazole hydrochloride (Compound 2x HCl ), 1-(1-ethoxyethyl)-3', 5'-dimethyl-1H,1'H-4,4'-bipyrazole (Compound 2b), or 1-(1-ethoxyethyl)-4-(4,4,5,5-tetramethyl-1,3,2-dioxaborolan-2-yl)-1H-pyrazole (Compound 2a), or a salt of any of the aforementioned.

In some embodiments, the present disclosure provides a compound which is 3,5-dimethyl-1H,1'H-[4,4']bipyrazolyl (Compound 2x) or a salt thereof.

In some embodiments, the present disclosure provides a compound which is (S)-4-(3-(cyanomethylene)azetidin-1-yl)-2,5-difluoro-N-(1,1,1-trifluoropropan-2-yl)benzamide (Compound 1x), (S)-2,5-difluoro-4-(3-oxoazetidin-1-yl)-N-(1,1,1-trifluoropropan-2-yl)benzamide (Compound 1c), (S)-2,5-difluoro-4-(3-hydroxyazetidin-1-yl)-N-(1,1,1-trifluoropropan-2-yl)benzamide (Compound 1b), or (S)-2,4,5-trifluoro-N-(1,1,1-trifluoropropan-2-yl)benzamide (Compound 1a), or a salt of any of the aforementioned.

As used herein, the term "about" refers to plus or minus 10% of the value.

As used herein, the term "reacting" is used as known in the art and generally refers to the bringing together of chemical reagents in such a manner so as to allow their interaction at the molecular level to achieve a chemical or physical transformation. In some embodiments, the reacting involves at least two reagents. In some embodiments, the reacting step or operation of a synthetic process may involve one or more substances in addition to the reagents such as solvent and/or a catalyst. The reacting steps or operations of the processes described herein can be conducted for a time and under conditions suitable for preparing the identified product. The terms "combining" and "mixing" with respect to reagents of a chemical reaction are used interchangeably with the term "reacting" herein. The term "coupling" also can be considered interchangeable with "reacting" but may be used in conjunction with a reaction step or operation that involves the linking of two organic fragments.

The processes described herein can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry; or by chromatography such as high performance liquid chromatography (HPLC) or thin layer chromatography. The compounds obtained by the reactions can be purified by any suitable method known in the art. For example, chromatography (medium pressure) on a suitable adsorbent (e.g., silica gel, alumina and the like), HPLC, or preparative thin layer chromatography; distillation; sublimation, trituration, or recrystallization. The purity of the compounds, in general, are determined by physical methods such as measuring the melting point (in case of a solid), obtaining a NMR spectrum, or performing a HPLC separation. If the melting point decreases, if unwanted signals in the NMR spectrum are decreased, or if extraneous peaks in an HPLC trace are removed, the compound can be said to have been purified. In some embodiments, the compounds are substantially purified.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene's Protective Groups in Organic Synthesis*, 4$^{th}$ Ed., John Wiley & Sons: New York, 2006, which is incorporated herein by reference in its entirety.

The reactions of the processes described herein can be carried out at appropriate temperatures which can be readily determined by the skilled artisan. Reaction temperatures will depend on, for example, the melting and boiling points of the reagents and solvent, if present; the thermodynamics of the reaction (e.g., vigorously exothermic reactions may need to be carried out at reduced temperatures); and the kinetics of the reaction (e.g., a high activation energy barrier may need elevated temperatures). "Elevated temperature" refers to temperatures above room temperature (about 22° C.).

The reactions of the processes described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the reaction step or operation, suitable solvent(s) for that particular reaction step or operation can be selected. Appropriate solvents include water, alkanes (such as pentanes, hexanes, heptanes, cyclohexane, etc., or a mixture thereof), aromatic solvents (such as benzene, toluene, xylene, etc.), alcohols (such as methanol, ethanol, isopropanol, etc.), ethers (such as dialkylethers, methyl tert-butyl ether (MTBE), tetrahydrofuran (THF), dioxane, etc.), esters (such as ethyl acetate, butyl acetate, etc.), halogenated hydrocarbon solvents (such as dichloromethane (DCM), chloroform, dichloroethane, tetrachloroethane), dimethylformamide (DMF), dimethylsulfoxide (DMSO), acetone, acetonitrile (ACN), hexamethylphosphoramide (HMPA) and N-methyl pyrrolidone (NMP). Such solvents can be used in either their wet or anhydrous forms.

Resolution of racemic mixtures of compounds can be carried out by any of numerous methods known in the art. For example, resolution of racemic mixtures can be carried out by elution on a column packed with an optically active resolving agent (e.g., dinitrobenzoylphenylglycine). Suitable elution solvent composition can be determined by one skilled in the art.

Methods

Compounds provided herein (e.g., Compound 1 free base and Compound 1 phosphoric acid salt) are JAK inhibitors, more specifically selective JAK1 inhibitors. A JAK1 selective inhibitor is a compound that inhibits JAK1 activity preferentially over other Janus kinases. For example, the compounds provided herein preferentially inhibit JAK1 over one or more of JAK2, JAK3, and TYK2. In some embodiments, the compounds inhibit JAK1 preferentially over JAK2 (e.g., have a JAK2/JAK1 $IC_{50}$ ratio >1). In some embodiments, the compounds are about 10-fold more selective for JAK1 over JAK2. In some embodiments, the compounds are about 3-fold, about 5-fold, about 10-fold, about 15-fold, or about 20-fold more selective for JAK1 over JAK2 as calculated by measuring $IC_{50}$ at 1 mM ATP (e.g., see Example A).

JAK1 plays a central role in a number of cytokine and growth factor signaling pathways that, when dysregulated, can result in or contribute to disease states. For example, IL-6 levels are elevated in rheumatoid arthritis, a disease in which it has been suggested to have detrimental effects (Fonesca, J. E. et al., Autoimmunity Reviews, 8:538-42, 2009). Because IL-6 signals, at least in part, through JAK1, antagonizing IL-6 directly or indirectly through JAK1 inhibition is expected to provide clinical benefit (Guschin, D., N., et al Embo J 14:1421, 1995; Smolen, J. S., et al. Lancet 371:987, 2008). Moreover, in some cancers JAK1 is mutated resulting in constitutive undesirable tumor cell growth and survival (Mullighan C G, Proc Natl Acad Sci U S A.106: 9414-8, 2009; Flex E., et al. J Exp Med. 205:751-8, 2008). In other autoimmune diseases and cancers elevated systemic levels of inflammatory cytokines that activate JAK1 may also contribute to the disease and/or associated symptoms. Therefore, patients with such diseases may benefit from JAK1 inhibition. Selective inhibitors of JAK1 may be efficacious while avoiding unnecessary and potentially undesirable effects of inhibiting other JAK kinases.

Selective inhibitors of JAK1, relative to other JAK kinases, may have multiple therapeutic advantages over less selective inhibitors. With respect to selectivity against JAK2, a number of important cytokines and growth factors signal through JAK2 including, for example, erythropoietin (Epo) and thrombopoietin (Tpo) (Parganas E, et al. Cell. 93:385-95, 1998). Epo is a key growth factor for red blood cells production; hence a paucity of Epo-dependent signaling can result in reduced numbers of red blood cells and anemia (Kaushansky K, NEJM 354:2034-45, 2006). Tpo, another example of a JAK2-dependent growth factor, plays a central role in controlling the proliferation and maturation of megakaryocytes—the cells from which platelets are produced (Kaushansky K, NEJM 354:2034-45, 2006). As such, reduced Tpo signaling would decrease megakaryocyte numbers (megakaryocytopenia) and lower circulating platelet counts (thrombocytopenia). This can result in undesirable and/or uncontrollable bleeding. Reduced inhibition of other JAKs, such as JAK3 and Tyk2, may also be desirable as humans lacking functional version of these kinases have been shown to suffer from numerous maladies such as severe-combined immunodeficiency or hyperimmunoglobulin E syndrome (Minegishi, Y, et al. Immunity 25:745-55, 2006; Macchi P, et al. Nature. 377:65-8, 1995). Therefore a JAK1 inhibitor with reduced affinity for other JAKs would have significant advantages over a less-selective inhibitor with respect to reduced side effects involving immune suppression, anemia and thrombocytopenia.

Another aspect of the present disclosure pertains to methods of treating a JAK-associated disease or disorder in an individual (e.g., patient) by administering to the individual in need of such treatment a therapeutically effective amount or dose of a compound of the present disclosure or a pharmaceutical composition thereof. A JAK-associated disease can include any disease, disorder or condition that is directly or indirectly linked to expression or activity of the JAK, including overexpression and/or abnormal activity levels. A JAK-associated disease can also include any disease, disorder or condition that can be prevented, ameliorated, or cured by modulating JAK activity.

Examples of JAK-associated diseases include diseases involving the immune system including, for example, organ transplant rejection (e.g., allograft rejection and graft versus host disease).

Further examples of JAK-associated diseases include autoimmune diseases such as multiple sclerosis, rheumatoid arthritis, juvenile arthritis, psoriatic arthritis, type I diabetes, lupus, psoriasis, inflammatory bowel disease, ulcerative colitis, Crohn's disease, myasthenia gravis, immunoglobulin nephropathies, myocarditis, autoimmune thyroid disorders, chronic obstructive pulmonary disease (COPD), and the like. In some embodiments, the autoimmune disease is an autoimmune bullous skin disorder such as pemphigus vulgaris (PV) or bullous pemphigoid (BP).

Further examples of JAK-associated diseases include allergic conditions such as asthma, food allergies, eszematous dermatitis, contact dermatitis, atopic dermatitis (atropic eczema), and rhinitis. Further examples of JAK-associated diseases include viral diseases such as Epstein Barr Virus (EBV), Hepatitis B, Hepatitis C, HIV, HTLV 1, Varicella-Zoster Virus (VZV) and Human Papilloma Virus (HPV).

Further examples of JAK-associated disease include diseases associated with cartilage turnover, for example, gouty arthritis, septic or infectious arthritis, reactive arthritis, reflex sympathetic dystrophy, algodystrophy, Tietze syndrome, costal athropathy, osteoarthritis deformans endemica, Mseleni disease, Handigodu disease, degeneration resulting from fibromyalgia, systemic lupus erythematosus, scleroderma, or ankylosing spondylitis.

Further examples of JAK-associated disease include congenital cartilage malformations, including hereditary chrondrolysis, chrondrodysplasias, and pseudochrondrodysplasias (e.g., microtia, enotia, and metaphyseal chrondrodysplasia).

Further examples of JAK-associated diseases or conditions include skin disorders such as psoriasis (for example, psoriasis vulgaris), atopic dermatitis, skin rash, skin irritation, skin sensitization (e.g., contact dermatitis or allergic contact dermatitis). For example, certain substances including some pharmaceuticals when topically applied can cause skin sensitization. In some embodiments, co-administration or sequential administration of at least one JAK inhibitor of the disclosure together with the agent causing unwanted sensitization can be helpful in treating such unwanted sensitization or dermatitis. In some embodiments, the skin disorder is treated by topical administration of at least one JAK inhibitor of the disclosure.

In further embodiments, the JAK-associated disease is cancer including those characterized by solid tumors (e.g., prostate cancer, renal cancer, hepatic cancer, pancreatic cancer, gastric cancer, breast cancer, lung cancer, cancers of the head and neck, thyroid cancer, glioblastoma, Kaposi's sarcoma, Castleman's disease, uterine leiomyosarcoma, melanoma etc.), hematological cancers (e.g., lymphoma, leukemia such as acute lymphoblastic leukemia (ALL), acute myelogenous leukemia (AML) or multiple myeloma), and skin cancer such as cutaneous T-cell lymphoma (CTCL)

and cutaneous B-cell lymphoma. Example CTCLs include Sezary syndrome and mycosis fungoides.

In some embodiments, the JAK inhibitors described herein, or in combination with other JAK inhibitors, such as those reported in U.S. publication no. 20070135461, which is incorporated herein by reference in its entirety, can be used to treat inflammation-associated cancers. In some embodiments, the cancer is associated with inflammatory bowel disease. In some embodiments, the inflammatory bowel disease is ulcerative colitis. In some embodiments, the inflammatory bowel disease is Crohn's disease. In some embodiments, the inflammation-associated cancer is colitis-associated cancer. In some embodiments, the inflammation-associated cancer is colon cancer or colorectal cancer. In some embodiments, the cancer is gastric cancer, gastrointestinal carcinoid tumor, gastrointestinal stromal tumor (GIST), adenocarcinoma, small intestine cancer, or rectal cancer.

JAK-associated diseases can further include those characterized by expression of:

JAK2 mutants such as those having at least one mutation in the pseudo-kinase domain (e.g., JAK2V617F); JAK2 mutants having at least one mutation outside of the pseudo-kinase domain; JAK1 mutants; JAK3 mutants; erythropoietin receptor (EPOR) mutants; or deregulated expression of CRLF2.

JAK-associated diseases can further include myeloproliferative disorders (MPDs) such as polycythemia vera (PV), essential thrombocythemia (ET), myelofibrosis with myeloid metaplasia (MMM), primary myelofibrosis (PMF), chronic myelogenous leukemia (CML), chronic myelomonocytic leukemia (CMML), hypereosinophilic syndrome (HES), systemic mast cell disease (SMCD), and the like. In some embodiments, the myeloproliferative disorder is myelofibrosis (e.g., primary myelofibrosis (PMF) or post polycythemia vera/essential thrombocythemia myelofibrosis (Post-PV/ET MF)). In some embodiments, the myeloproliferative disorder is post-essential thrombocythemia myelofibrosis (Post-ET MF). In some embodiments, the myeloproliferative disorder is post polycythemia vera myelofibrosis (Post-PV MF).

In some embodiments, JAK inhibitors described herein can be further used to treat myelodysplastic syndrome (MDS) in a patient in need thereof. In some embodiments, said patient is red blood cell transfusion dependent.

As used herein, myelodysplastic syndromes are intended to encompass heterogeneous and clonal hematopoietic disorders that are characterized by ineffective hematopoiesis on one or more of the major myeloid cell lineages. Myelodysplastic syndromes are associated with bone marrow failure, peripheral blood cytopenias, and a propensity to progress to acute myeloid leukemia (AML). Moreover, clonal cytogenetic abnormalities can be detected in about 50% of cases with MDS. In 1997, The World Health Organization (WHO) in conjunction with the Society for Hematopathology (SH) and the European Association of Hematopathology (EAHP) proposed new classifications for hematopoietic neoplasms (Harris, et al., *J Clin Oncol* 1999; 17:3835-3849; Vardiman, et al., *Blood* 2002; 100:2292-2302). For MDS, the WHO utilized not only the morphologic criteria from the French-American-British (FAB) classification but also incorporated available genetic, biologic, and clinical characteristics to define subsets of MDS (Bennett, et al., *Br J Haematol* 1982; 51:189-199). In 2008, the WHO classification of MDS (Table 1) was further refined to allow precise and prognostically relevant subclassification of unilineage dysplasia by incorporating new clinical and scientific information (Vardiman, et al., *Blood* 2009; 114:937-951; Swerdlow, et al., *WHO Classification of Tumours of Haematopoietic and Lymphoid Tissues*. 4th Edition. Lyon France: IARC Press; 2008:88-103; Bunning and Germing, "Myelodysplastic syndromes/neoplasms" in Chapter 5, Swerdlow, et al, eds. *WHO Classification of Tumours of Haematopoietic and Lymphoid Tissues*. (ed. 4th edition): Lyon, France: IARC Press; 2008: 88-103).

TABLE 1

2008 WHO Classification for De Novo Myelodysplastic Syndrome

| Subtype | Blood | Bone Marrow |
|---|---|---|
| Refractory cytopenia with unilineage dysplasia (RCUD) | Single or Bicytopenia | Dysplasia in ≥10% of 1 cell line, <5% blasts |
| Refractory anemia with ring sideroblasts (RARS) | Anemia, no blasts | ≥15% of erythroid precursors w/ring sideroblasts, erythroid dysplasia only, <5% blasts |
| Refractory cytopenia with multilineage dysplasia | Cytopenia(s), <1 × $10^9$/L monocytes | Dysplasia in ≥10% of cells in ≥2 hematopoietic lineages, ±15% ring sideroblasts, <5% blasts |
| Refractory anemia with excess blasts-1 (RAEB-1) | Cytopenia(s), ≤2% to 4% blasts, <1 × $10^9$/L monocytes | Unilineage or multilineage dysplasia, No Auer rods, 5% to 9% blasts |
| Refractory anemia with excess blasts-2 (RAEB-2) | Cytopenia(s), ≤5% to 19% blasts, <1 × $10^9$/L monocytes | Unilineage or multilineage dysplasia, ±Auer rods, 10% to 19% blasts |
| Myelodysplastic syndrome, unclassified (MDS-U) | Cytopenias | Unilineage or no dysplasia but characteristic MDS cytogenetics, <5% blasts |
| MDS associated with isolated del (5q) | Anemia, platelets normal or increased | Unilineage erythroid. Isolated del(5q), <5% blasts |

In some embodiments, the myelodysplastic syndrome is refractory cytopenia with unilineage dysplasia (RCUD).

In some embodiments, the myelodysplastic syndrome is refractory anemia with ring sideroblasts (RARS).

In some embodiments, the myelodysplastic syndrome is refractory cytopenia with multilineage dysplasia.

In some embodiments, the myelodysplastic syndrome is refractory anemia with excess blasts-1 (RAEB-1).

In some embodiments, the myelodysplastic syndrome is refractory anemia with excess blasts-2 (RAEB-2).

In some embodiments, the myelodysplastic syndrome is myelodysplastic syndrome, unclassified (MDS-U).

In some embodiments, the myelodysplastic syndrome is myelodysplastic syndrome associated with isolated del(5q).

In some embodiments, the myelodysplastic syndrome is refractory to erythropoiesis-stimulating agents.

The present disclosure further provides methods of treating psoriasis or other skin disorders by administration of a topical formulation containing a compound provided herein.

In some embodiments, JAK inhibitors described herein can be used to treat pulmonary arterial hypertension.

The present disclosure further provides a method of treating dermatological side effects of other pharmaceuticals by administration of the compound provided herein. For example, numerous pharmaceutical agents result in unwanted allergic reactions which can manifest as acneiform rash or related dermatitis. Example pharmaceutical agents that have such undesirable side effects include anticancer drugs such as gefitinib, cetuximab, erlotinib, and the like. The compounds provided herein can be administered systemically or topically (e.g., localized to the vicinity of the dermatitis) in combination with (e.g., simultaneously or sequentially) the pharmaceutical agent having the undesirable dermatological side effect. In some embodiments, the compound provided herein can be administered topically together with one or more other pharmaceuticals, where the other pharmaceuticals when topically applied in the absence of a compound provided herein cause contact dermatitis, allergic contact sensitization, or similar skin disorder. Accordingly, compositions of the disclosure include topical formulations containing the compound provided herein and a further pharmaceutical agent which can cause dermatitis, skin disorders, or related side effects.

Further JAK-associated diseases include inflammation and inflammatory diseases. Example inflammatory diseases include sarcoidosis, inflammatory diseases of the eye (e.g., iritis, uveitis, scleritis, conjunctivitis, or related disease), inflammatory diseases of the respiratory tract (e.g., the upper respiratory tract including the nose and sinuses such as rhinitis or sinusitis or the lower respiratory tract including bronchitis, chronic obstructive pulmonary disease, and the like), inflammatory myopathy such as myocarditis, and other inflammatory diseases. In some embodiments, the inflammation disease of the eye is blepharitis.

The JAK inhibitors described herein can further be used to treat ischemia reperfusion injuries or a disease or condition related to an inflammatory ischemic event such as stroke or cardiac arrest. The JAK inhibitors described herein can further be used to treat endotoxin-driven disease state (e.g., complications after bypass surgery or chronic endotoxin states contributing to chronic cardiac failure). The JAK inhibitors described herein can further be used to treat anorexia, cachexia, or fatigue such as that resulting from or associated with cancer. The JAK inhibitors described herein can further be used to treat restenosis, sclerodermitis, or fibrosis. The JAK inhibitors described herein can further be used to treat conditions associated with hypoxia or astrogliosis such as, for example, diabetic retinopathy, cancer, or neurodegeneration. See, e.g., Dudley, A. C. et al. *Biochem. J*, 2005, 390(Pt 2):427-36 and Sriram, K. et al. *J. Biol. Chem.* 2004, 279(19):19936-47. Epub 2004 Mar. 2, both of which are incorporated herein by reference in their entirety. The JAK inhibitors described herein can be used to treat Alzheimer's disease.

The JAK inhibitors described herein can further be used to treat other inflammatory diseases such as systemic inflammatory response syndrome (SIRS) and septic shock.

The JAK inhibitors described herein can further be used to treat gout and increased prostate size due to, e.g., benign prostatic hypertrophy or benign prostatic hyperplasia.

Further JAK-associated diseases include bone resorption diseases such as osteoporosis, osteoarthritis. Bone resorption can also be associated with other conditions such as hormonal imbalance and/or hormonal therapy, autoimmune disease (e.g. osseous sarcoidosis), or cancer (e.g. myeloma). The reduction of the bone resorption due to the JAK inhibitors can be about 10%, about 20%, about 30%, about 40%, about 50%, about 60%, about 70%, about 80%, or about 90%.

In some embodiments, JAK inhibitors described herein can further be used to treat a dry eye disorder. As used herein, "dry eye disorder" is intended to encompass the disease states summarized in a recent official report of the Dry Eye Workshop (DEWS), which defined dry eye as "a multifactorial disease of the tears and ocular surface that results in symptoms of discomfort, visual disturbance, and tear film instability with potential damage to the ocular surface. It is accompanied by increased osmolarity of the tear film and inflammation of the ocular surface." Lemp, "The Definition and Classification of Dry Eye Disease: Report of the Definition and Classification Subcommittee of the International Dry Eye Workshop", *The Ocular Surface*, 5(2), 75-92 April 2007, which is incorporated herein by reference in its entirety. In some embodiments, the dry eye disorder is selected from aqueous tear-deficient dry eye (ADDE) or evaporative dry eye disorder, or appropriate combinations thereof. In some embodiments, the dry eye disorder is Sjogren syndrome dry eye (SSDE). In some embodiments, the dry eye disorder is non-Sjogren syndrome dry eye (NSSDE).

In a further aspect, the present disclosure provides a method of treating conjunctivitis, uveitis (including chronic uveitis), chorioditis, retinitis, cyclitis, sclieritis, episcleritis, or iritis; treating inflammation or pain related to corneal transplant, LASIK (laser assisted in situ keratomileusis), photorefractive keratectomy, or LASEK (laser assisted subepithelial keratomileusis); inhibiting loss of visual acuity related to corneal transplant, LASIK, photorefractive keratectomy, or LASEK; or inhibiting transplant rejection in a patient in need thereof, comprising administering to the patient a therapeutically effective amount of the compound provided herein, or a pharmaceutically acceptable salt thereof.

Additionally, the compounds provided herein, or in combination with other JAK inhibitors, such as those reported in U.S. Ser. No. 11/637,545, which is incorporated herein by reference in its entirety, can be used to treat respiratory dysfunction or failure associated with viral infection, such as influenza and SARS.

In some embodiments, the present disclosure provides Compound 1 free base and Compound 1 phosphoric acid salt, as described in any of the embodiments herein, for use in a method of treating any of the diseases or disorders described herein. In some embodiments, the present disclosure provides the use of Compound 1 free base and Compound 1 phosphoric acid salt as described in any of the embodiments herein, for the preparation of a medicament for use in a method of treating any of the diseases or disorders described herein.

In some embodiments, the present disclosure provides Compound 1 free base and Compound 1 phosphoric acid salt as described herein, or a pharmaceutically acceptable salt thereof, for use in a method of modulating JAK1. In some embodiments, the present disclosure also provides use of Compound 1 free base and Compound 1 phosphoric acid salt as described herein, or a pharmaceutically acceptable salt thereof, for the preparation of a medicament for use in a method of modulating JAK1.

As used herein, the term "contacting" refers to the bringing together of indicated moieties in an in vitro system or an in vivo system. For example, "contacting" a JAK with a compound provided herein includes the administration of a compound of the present disclosure to an individual or patient, such as a human, having a JAK, as well as, for example, introducing a compound provided herein into a sample containing a cellular or purified preparation containing the JAK.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician. In some embodiments, the therapeutically effective amount is about 5 mg to about 1000 mg, or about 10 mg to about 500 mg.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used herein, the term "preventing" or "prevention" refers to for example, preventing a disease, condition or disorder in an individual who may be predisposed to the disease, condition or disorder but does not yet experience or display the pathology or symptomatology of the disease.

Combination Therapies

The methods described herein can further comprise administering one or more additional therapeutic agents. The one or more additional therapeutic agents can be administered to a patient simultaneously or sequentially.

In some embodiments, the method further comprises administering an additional therapeutic agent selected from IMiDs, an anti-IL-6 agent, an anti-TNF-α agent, a hypomethylating agent, and a biologic response modifier (BRM).

Generally, a BRM is a substances made from living organisms to treat disease, which may occur naturally in the body or may be made in the laboratory. Examples of BRMs include IL-2, interferon, various types of colony-stimulating factors (CSF, GM-CSF, G-CSF), monoclonal antibodies such as abciximab, etanercept, infliximab, rituximab, trasturzumab, and high dose ascorbate.

In some embodiments, the anti-TNF-α agent is infliximab or etanercept.

In some embodiments, the hypomethylating agent is a DNA methyltransferase inhibitor. In some embodiments, the DNA methyltransferase inhibitor is selected from 5 azacytidine and decitabine.

Generally, IMiDs are as immunomodulatory agents. In some embodiments, the IMiD is selected from thalidomide, lenalidomide, pomalidomide, CC-11006, and CC-10015.

In some embodiments, the method further comprises administering an additional therapeutic agent selected from anti-thymocyte globulin, recombinant human granulocyte colony-stimulating factor (G CSF), granulocyte-monocyte CSF (GM-CSF), a erythropoiesis-stimulating agent (ESA), and cyclosporine.

In some embodiments, the method further comprises administering an additional
JAK inhibitor to the patient. In some embodiments, the additional JAK inhibitor is tofacitinib or ruxolitinib.

One or more additional pharmaceutical agents such as, for example, chemotherapeutics, anti-inflammatory agents, steroids, immunesuppressants, as well as PI3Kδ, mTor, Bcr-Abl, Flt-3, RAF and FAK kinase inhibitors such as, for example, those described in WO 2006/056399, which is incorporated herein by reference in its entirety, or other agents can be used in combination with the compounds described herein for treatment of JAK-associated diseases, disorders or conditions. The one or more additional pharmaceutical agents can be administered to a patient simultaneously or sequentially.

Example chemotherapeutics include proteosome inhibitors (e.g., bortezomib), thalidomide, revlimid, and DNA-damaging agents such as melphalan, doxorubicin, cyclophosphamide, vincristine, etoposide, carmustine, and the like.

Example steroids include coriticosteroids such as dexamethasone or prednisone.

Example Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491, all of which are incorporated herein by reference in their entirety.

Example suitable Flt-3 inhibitors include compounds, and their pharmaceutically acceptable salts, as disclosed in WO 03/037347, WO 03/099771, and WO 04/046120, all of which are incorporated herein by reference in their entirety.

Example suitable RAF inhibitors include compounds, and their pharmaceutically acceptable salts, as disclosed in WO 00/09495 and WO 05/028444, both of which are incorporated herein by reference in their entirety.

Example suitable FAK inhibitors include compounds, and their pharmaceutically acceptable salts, as disclosed in WO 04/080980, WO 04/056786, WO 03/024967, WO 01/064655, WO 00/053595, and WO 01/014402, all of which are incorporated herein by reference in their entirety.

In some embodiments, compounds provided herein (e.g., Compound 1 free base and Compound 1 phosphoric acid salt) can be used in combination with one or more other kinase inhibitors including imatinib, particularly for treating patients resistant to imatinib or other kinase inhibitors.

In some embodiments, a suitable chemotherapeutical agent can be selected from antimetabolite agents, topoisomerase 1 inhibitors, platinum analogs, taxanes, anthracyclines, and EGFR inhibitors, and combinations thereof In some embodiments, antimetabolite agents include capecitabine, gemcitabine, and fluorouracil (5-FU).

In some embodiments, taxanes include paclitaxel, Abraxane® (paclitaxel protein-bound particles for injectable suspension), and Taxotere® (docetaxel).

In some embodiments, platinum analogs include oxaliplatin, cisplatin, and carboplatin.

In some embodiments, topoisomerase 1 inhibitors include irinotecan and topotecan.

In some embodiment, anthracyclines include doxorubicin or liposomal formulations of doxorubicin.

In some embodiments, the chemotherapeutic is FOLFIRINOX (5-FU, lecovorin, irinotecan and oxaliplatin). In some embodiments, the chemotherapeutic agent is gemcitabine and Abraxane® (paclitaxel protein-bound particles for injectable suspension).

In some embodiments, compounds provided herein (e.g., Compound 1 free base and Compound 1 phosphoric acid salt) can be used in combination with a chemotherapeutic in the treatment of cancer, such as multiple myeloma, and may improve the treatment response as compared to the response to the chemotherapeutic agent alone, without exacerbation of its toxic effects. Examples of additional pharmaceutical agents used in the treatment of multiple myeloma, for example, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. Additive or synergistic effects are desirable outcomes of combining a JAK inhibitor of the present disclosure with an additional agent. Furthermore, resistance of multiple myeloma cells to agents such as dexamethasone may be reversible upon treatment with a JAK inhibitor of the present disclosure. The agents can be combined with compounds provided herein in a single or continuous dosage form, or the agents can be administered simultaneously or sequentially as separate dosage forms.

In some embodiments, a corticosteroid such as dexamethasone is administered to a patient in combination with at least one JAK inhibitor where the dexamethasone is administered intermittently as opposed to continuously.

In some further embodiments, combinations of compounds provided herein with other therapeutic agents can be administered to a patient prior to, during, and/or after a bone marrow transplant or stem cell transplant.

In some embodiments, the additional therapeutic agent is fluocinolone acetonide (Retisert®), or rimexolone (AL-2178, Vexol, Alcon).

In some embodiments, the additional therapeutic agent is cyclosporine (Restasis®).

In some embodiments, the additional therapeutic agent is a corticosteroid. In some embodiments, the corticosteroid is triamcinolone, dexamethasone, fluocinolone, cortisone, prednisolone, or flumetholone.

In some embodiments, the additional therapeutic agent is selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), actemra, gemcitabine, oxaliplatin, L-asparaginase, or thalidomide.

In some embodiments, the additional therapeutic agent is an anti-angiogenic agent, cholinergic agonist, TRP-1 receptor modulator, a calcium channel blocker, a mucin secretagogue, MUC1 stimulant, a calcineurin inhibitor, a corticosteroid, a P2Y2 receptor agonist, a muscarinic receptor agonist, an mTOR inhibitor, another JAK inhibitor, Bcr-Abl kinase inhibitor, Flt-3 kinase inhibitor, RAF kinase inhibitor, and FAK kinase inhibitor such as, for example, those described in WO 2006/056399, which is incorporated herein by reference in its entirety. In some embodiments, the additional therapeutic agent is a tetracycline derivative (e.g., minocycline or doxycline). In some embodiments, the additional therapeutic agent binds to FKBP12.

In some embodiments, the additional therapeutic agent is an alkylating agent or DNA cross-linking agent; an anti-metabolite/demethylating agent (e.g., 5-flurouracil, capecitabine or azacitidine); an anti-hormone therapy (e.g., hormone receptor antagonists, SERMs, or aromatase inhibitor); a mitotic inhibitor (e.g. vincristine or paclitaxel); an topoisomerase (I or II) inhibitor (e.g. mitoxantrone and irinotecan); an apoptotic inducers (e.g. ABT-737); a nucleic acid therapy (e.g. antisense or RNAi); nuclear receptor ligands (e.g., agonists and/or antagonists: all-trans retinoic acid or bexarotene); epigenetic targeting agents such as histone deacetylase inhibitors (e.g. vorinostat), hypomethylating agents (e.g. decitabine); regulators of protein stability such as Hsp90 inhibitors, ubiquitin and/or ubiquitin like conjugating or deconjugating molecules; or an EGFR inhibitor (erlotinib).

In some embodiments, the additional therapeutic agent(s) are demulcent eye drops (also known as "artificial tears"), which include, but are not limited to, compositions containing polyvinylalcohol, hydroxypropyl methylcellulose, glycerin, polyethylene glycol (e.g. PEG400), or carboxymethyl cellulose. Artificial tears can help in the treatment of dry eye by compensating for reduced moistening and lubricating capacity of the tear film. In some embodiments, the additional therapeutic agent is a mucolytic drug, such as N-acetyl-cysteine, which can interact with the mucoproteins and, therefore, to decrease the viscosity of the tear film.

In some embodiments, the additional therapeutic agent includes an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paramomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

In some embodiments, compounds provided herein can be used in combination with an immune check point inhibitors in the treatment of diseases such as cancer. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab or pembrolizumab. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A or MEDI4736.

In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518 or MK-4166.

In some embodiments, the inhibitor of an immune checkpoint molecule is an inhibitor of OX40, e.g., an anti-OX40 antibody or OX40 L fusion protein. In some embodiments, the anti-OX40 antibody is MEDI0562. In some embodiments, the OX40 L fusion protein is MEDI6383.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Pharmaceutical Formulations and Dosage Forms

When employed as pharmaceuticals, the compounds provided herein can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This disclosure also includes pharmaceutical compositions which contain, as the active ingredient, e.g., Compound 1 free base and/or Compound 1 phosphoric acid salt, in combination with one or more pharmaceutically acceptable carriers (excipients). In some embodiments, the composition is suitable for topical administration. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, a compound provided herein (e.g., Compound 1 free base and Compound 1 phosphoric acid salt) can be milled to provide the appropriate particle size prior to combining with the other ingredients. If Compound 1 free base or Compound 1 phosphoric acid salt is substantially insoluble, it can be milled to a particle size of less than 200 mesh. If Compound 1 free base and Compound 1 phosphoric acid salt is substantially water soluble, the particle size can be adjusted by milling to provide a substantially uniform distribution in the formulation, e.g. about 40 mesh.

The compounds provided herein may be milled using known milling procedures such as wet milling to obtain a particle size appropriate for tablet formation and for other formulation types. Finely divided (nanoparticulate) preparations of the compounds provided herein can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at Compound 1 free base and/or Compound 1 phosphoric acid salt, and at least one pharmaceutically acceptable carrier. In some embodiments, the composition comprises Compound 1 free base and/or Compound 1 phosphoric acid salt described herein, and at least one component selected from microcrystalline cellulose, lactose monohydrate, hydroxypropyl methylcellulose, and polyethylene oxide. In some embodiments, the composition comprises Compound 1 free base and/or Compound 1 phosphoric acid salt, and microcrystalline cellulose, lactose monohydrate, and hydroxypropyl methylcellulose. In some embodiments, the composition comprises Compound 1 free base and/or Compound 1 phosphoric acid salt, and microcrystalline cellulose, lactose monohydrate, and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 1 to about 1,000 mg, from about 1 mg to about 100 mg, from 1 mg to about 50 mg, and from about 1 mg to 10 mg of active ingredient (e.g., Compound 1 free base and Compound 1 phosphoric acid salt). Preferably, the dosage is from about 1 mg to about 50 mg or about 1 mg to about 10 mg of active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compositions comprise from about 1 to about 1,000 mg, from about 1 mg to about 100 mg, from 1 mg to about 50 mg, and from about 1 mg to 10 mg of active ingredient (e.g., Compound 1 free base and Compound 1 phosphoric acid salt). Preferably, the compositions comprise from about 1 mg to about 50 mg or about 1 mg to about 10 mg of active ingredient. One having ordinary skill in the art will appreciate that this embodies compounds or compositions containing about 1 mg to about 10 mg, about 1 mg to about 20 mg, about 1 mg to about 25 mg, about 1 mg to about 50 mg of the active ingredient.

The active compound (e.g., Compound 1 free base and Compound 1 phosphoric acid salt) may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present disclosure.

The tablets or pills of the present disclosure can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions provided herein can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white Vaseline, and the like. Carrier compositions of creams can be based on water in combination with glycerol and one or more other components, e.g. glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound provided herein. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present disclosure can vary according to, for example, the particular use for which the treatment is made, the manner of administration of the compound, the health and condition of the patient, and the judgment of the prescribing physician. The proportion or concentration of Compound 1 free base or Compound 1 phosphoric acid salt in a pharmaceutical composition can vary depending upon a number of factors including dosage, chemical characteristics (e.g., hydrophobicity), and the route of administration. For example, the compounds provided herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the disclosure can further include one or more additional pharmaceutical agents such as a chemotherapeutic, steroid, anti-inflammatory compound, or immunosuppressant, examples of which are listed hereinabove.

In some embodiments, Compound 1 free base or Compound 1 phosphoric acid salt is administered as an ophthalmic composition. Accordingly, in some embodiments, the methods comprise administration of the compound, or pharmaceutically acceptable salt thereof, and an ophthalmically acceptable carrier. In some embodiments, the ophthalmic composition is a liquid composition, semi-solid composition, insert, film, microparticles or nanoparticles.

In some embodiments, the ophthalmic composition is a liquid composition. In some embodiments, the ophthalmic composition is a semi-solid composition. In some embodiments, the ophthalmic composition is a topical composition. The topical compositions include, but are not limited to liquid and semi-solid compositions. In some embodiments, the ophthalmic composition is a topical composition. In some embodiments, the topical composition comprises aqueous solution, an aqueous suspension, an ointment or a gel. In some embodiments, the ophthalmic composition is topically applied to the front of the eye, under the upper eyelid, on the lower eyelid and in the cul-de-sac. In some embodiments, the ophthalmic composition is sterilized. The sterilization can be accomplished by known techniques like sterilizing filtration of the solution or by heating of the solution in the ampoule ready for use. The ophthalmic compositions of the disclosure can further contain pharmaceutical excipients suitable for the preparation of ophthalmic formulations. Examples of such excipients are preserving agents, buffering agents, chelating agents, antioxidant agents and salts for regulating the osmotic pressure.

As used herein, the term "ophthalmically acceptable carrier" refers to any material that can contain and release the compound, or pharmaceutically acceptable salt thereof, and that is compatible with the eye. In some embodiments, the ophthalmically acceptable carrier is water or an aqueous solution or suspension, but also includes oils such as those used to make ointments and polymer matrices such as used in ocular inserts. In some embodiments, the composition may be an aqueous suspension comprising the compound, or pharmaceutically acceptable salt thereof. Liquid ophthalmic compositions, including both ointments and suspensions, may have a viscosity that is suited for the selected route of administration. In some embodiments, the ophthalmic composition has a viscosity in the range of from about 1,000 to about 30,000 centipoise.

In some embodiments, the ophthalmic compositions may further comprise one or more of surfactants, adjuvants, buffers, antioxidants, tonicity adjusters, preservatives (e.g., EDTA, BAK (benzalkonium chloride), sodium chlorite, sodium perborate, polyquaterium-1), thickeners or viscosity modifiers (e.g., carboxymethyl cellulose, hydroxymethyl cellulose, polyvinyl alcohol, polyethylene glycol, glycol 400, propylene glycol hydroxymethyl cellulose, hydroxypropyl-guar, hyaluronic acid, and hydroxypropyl cellulose) and the like. Additives in the formulation may include, but are not limited to, sodium chloride, sodium bicarbonate, sorbic acid, methyl paraben, propyl paraben, chlorhexidine, castor oil, and sodium perborate.

Aqueous ophthalmic compositions (solutions or suspensions) generally do not contain physiologically or ophthalmically harmful constituents. In some embodiments, purified or deionized water is used in the composition. The pH may be adjusted by adding any physiologically and ophthalmically acceptable pH adjusting acids, bases or buffers to within the range of about 5.0 to 8.5. Ophthalmically acceptable examples of acids include acetic, boric, citric, lactic, phosphoric, hydrochloric, and the like, and examples of bases include sodium hydroxide, sodium phosphate, sodium borate, sodium citrate, sodium acetate, sodium lactate, tromethamine, trishydroxymethylamino-methane, and the like. Salts and buffers include citrate/dextrose, sodium bicarbonate, ammonium chloride and mixtures of the aforementioned acids and bases. In some embodiments, the methods involve forming or supplying a depot of the therapeutic agent in contact with the external surface of the eye. A depot refers to a source of therapeutic agent that is not rapidly removed by tears or other eye clearance mechanisms. This allows for continued, sustained high concentrations of therapeutic agent to be present in the fluid on the external surface of the eye by a single application. Without wishing to be bound by any theory, it is believed that absorption and penetration may be dependent on both the dissolved drug concentration and the contact duration of the external tissue with the drug containing fluid. As the drug is removed by clearance of the ocular fluid and/or absorption into the eye tissue, more drug is provided, e.g. dissolved, into the replenished ocular fluid from the depot. Accordingly, the use of a depot may more easily facilitate loading of the ocular tissue for more insoluble therapeutic agents. In some embodiments, the depot can remain for up to eight hours or more. In some embodiments, the ophthalmic depot forms includes, but is not limited to, aqueous polymeric suspensions, ointments, and solid inserts.

In some embodiments, the ophthalmic composition is an ointment or gel. In some embodiment, the ophthalmic composition is an oil-based delivery vehicle. In some embodiments, the composition comprises a petroleum or lanolin base to which is added the active ingredient, usually as 0.1 to 2%, and excipients. Common bases may include, but are not limited to, mineral oil, petrolatum and combinations thereof. In some embodiments, the ointment is applied as a ribbon onto the lower eyelid.

In some embodiment, the ophthalmic composition is an ophthalmic insert. In some embodiments, the ophthalmic insert is biologically inert, soft, bio-erodible, viscoelastic, stable to sterilization after exposure to therapeutic agents, resistant to infections from air borne bacteria, bio-erodible, biocompatible, and/or viscoelastic. In some embodiments, the insert comprises an ophthalmically acceptable matrix, e.g., a polymer matrix. The matrix is typically a polymer and the therapeutic agent is generally dispersed therein or bonded to the polymer matrix. In some embodiments, the therapeutic agent may be slowly released from the matrix through dissolution or hydrolysis of the covalent bond. In some embodiments, the polymer is bioerodible (soluble) and the dissolution rate thereof can control the release rate of the therapeutic agent dispersed therein. In another form, the polymer matrix is a biodegradable polymer that breaks down such as by hydrolysis to thereby release the therapeutic agent bonded thereto or dispersed therein. In further embodiments, the matrix and therapeutic agent can be surrounded with an additional polymeric coating to further control release. In some embodiments, the insert comprises a biodegradable polymer such as polycaprolactone (PCL), an ethylene/vinyl acetate copolymer (EVA), polyalkyl cyanoacrylate, polyurethane, a nylon, or poly (dl-lactide-co-glycolide) (PLGA), or a copolymer of any of these. In some embodiments, the therapeutic agent is dispersed into the matrix material or dispersed amongst the monomer composition used to make the matrix material prior to polymerization. In some embodiments, the amount of therapeutic agent is from about 0.1 to about 50%, or from about 2 to about 20%. In further embodiments, the biodegradable or bioerodible polymer matrix is used so that the spent insert does not have to be removed. As the biodegradable or bioerodible polymer is degraded or dissolved, the therapeutic agent is released.

In further embodiments, the ophthalmic insert comprises a polymer, including, but are not limited to, those described in Wagh, et al., "Polymers used in ocular dosage form and drug delivery systems", *Asian J. Pharm.*, pages 12-17 (January 2008), which is incorporated herein by reference in its entirety. In some embodiments, the insert comprises a polymer selected from polyvinylpyrrolidone (PVP), an acrylate or methacrylate polymer or copolymer (e.g., Eudragit® family of polymers from Rohm or Degussa), hydroxymethyl cellulose, polyacrylic acid, poly(amidoamine) dendrimers, poly(dimethyl siloxane), polyethylene oxide, poly(lactide-co-glycolide), poly(2-hydroxyethylmethacrylate), poly(vinyl alcohol), or poly(propylene fumarate). In some embodiments, the insert comprises Gelfoam® R. In some embodiments, the insert is a polyacrylic acid of 450 kDa-cysteine conjugate.

In some embodiments, the ophthalmic composition is an ophthalmic film. Polymers suitable for such films include, but are not limited to, those described in Wagh, et al. (ibid), In some embodiments, the film is a soft-contact lens, such as ones made from copolymers of N,N-diethylacrylamide and methacrylic acid crosslinked with ethyleneglycol dimethacrylate.

In some embodiments, the ophthalmic compositon comprises microspheres or nanoparticles. In some embodiment, the microspheres comprise gelatin. In some embodiments, the micro spheres are injected to the posterior segment of the eye, in the chroroidal space, in the sclera, intravitreally or sub-retinally. In some embodiments, the microspheres or nanoparticles comprises a polymer including, but not limited to, those described in Wagh, et al. (ibid), which is incorporated herein by reference in its entirety. In some embodiments, the polymer is chitosan, a polycarboxylic acid such as polyacrylic acid, albumin particles, hyaluronic acid esters, polyitaconic acid, poly(butyl)cyanoacrylate, polycaprolactone, poly(isobutyl)caprolactone, poly(lactic acid-co-glycolic acid), or poly(lactic acid). In some embodiments, the microspheres or nanoparticles comprise solid lipid particles.

In some embodiments, the ophthalmic composition comprises an ion-exchange resin. In some embodiments, the ion-exchange resin is an inorganic zeolite or synthetic organic resin. In some embodiments, the ion-exchange resin includes, but is not limited to, those described in Wagh, et al. (ibid), which is incorporated herein by reference in its entirety. In some embodiments, the ion-exchange resin is a partially neutralized polyacrylic acid.

In some embodiments, the ophthalmic composition is an aqueous polymeric suspension. In some embodiments, the therapeutic agent or a polymeric suspending agent is suspended in an aqueous medium. In some embodiments, the aqueous polymeric suspensions may be formulated so that they retain the same or substantially the same viscosity in the eye that they had prior to administration to the eye. In some embodiments, they may be formulated so that there is increased gelation upon contact with tear fluid.

Kits

The present disclosure also includes pharmaceutical kits useful, for example, in the treatment or prevention of JAK-associated diseases or disorders, such as cancer, which include one or more containers containing a pharmaceutical composition comprising a therapeutically effective amount of Compound 1 free base or Compound 1 phosphoric acid salt. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The disclosure will be described in greater detail by way of specific examples. The following examples are offered for illustrative purposes, and are not intended to limit the disclosure in any manner. Those of skill in the art will readily recognize a variety of non-critical parameters which can be changed or modified to yield essentially the same results. The compounds of the Examples have been found to be JAK inhibitors according to at least one assay described herein.

EXAMPLES

Intermediate 1. 3,5-Dimethyl-4,4'-bipyrazole (Compound 2x)

Scheme 1.

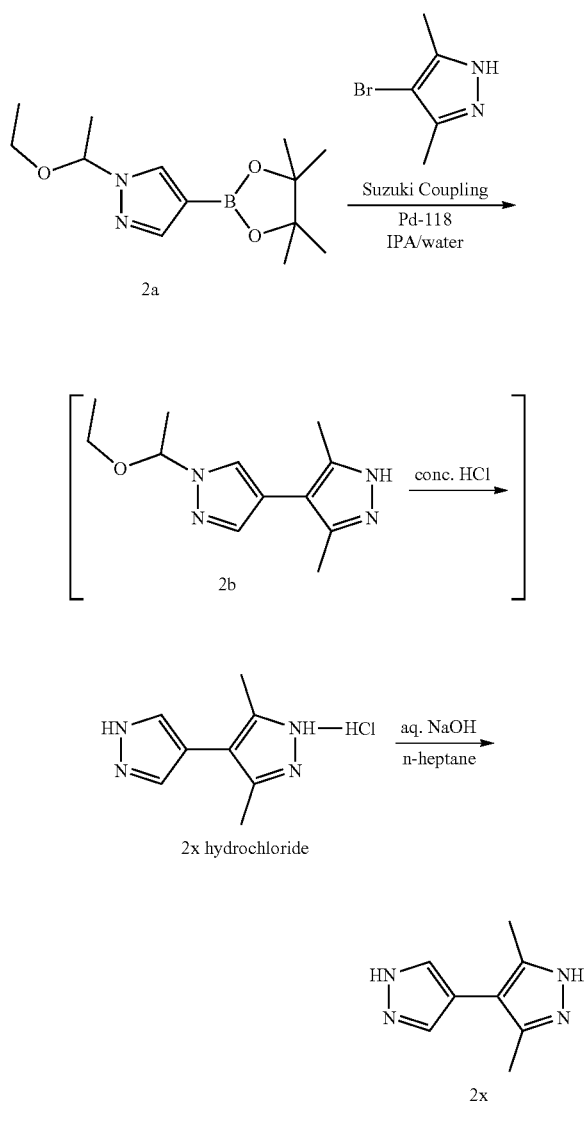

Step 1. 1'-(1-ethoxy-ethyl)-3,5-dimethyl-1H,1'H-[4,4']bipyrazolyl (Compound 2b)

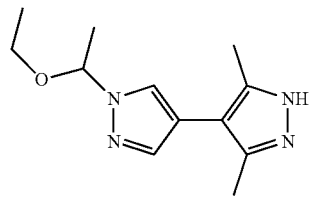 [SMILES: CCOC(C)n1cc(-c2c(C)n[nH]c2C)cn1]

To a 100 L glass reactor purged with nitrogen was sequentially added 1-propanol (5.0 L), potable water (6.0 L), $K_2HPO_4$ (1032 g), 4-bromo-3,5-dimethylpyrazole (1084 g), and 1-(1-ethoxyethyl)-4-(4,4,5,5-tetramethyl-1,3,2-dioxaborolan-2-yl)-1H-pyrazole (Compound 2a, 1502 g). Nitrogen gas was bubbled through the reaction mixture for 18 minutes, Pd-118 (55.07 g) was then charged to the reactor, and nitrogen gas was bubbled through the reaction mixture for an additional 18 minutes. The reaction mixture was heated to about 90° C. and stirred for about 4 hours at about 90° C. The reaction mixture was then cooled to about 17° C. and the phases were separated. The organic phase was treated with activated charcoal (1500 g), heated to about 70° C., stirred at about 70° C. for about 4 hours, and cooled to about 21° C. The mixture was filtered through Celite (1500 g) and the filter cake was washed with 2-propanol (15.0 L). The combined filtrate and wash were concentrated under vacuum at about 58° C. to afford the crude desired product, 1'-(1-ethoxy-ethyl)-3,5-dimethyl-1H,1'H-[4,4']bipyrazolyl (2593 g), which was used in the subsequent treatment.

The crude 1'-(1-ethoxy-ethyl)-3,5-dimethyl-1H,1'H-[4,4'] bipyrazolyl (2590 g) and ethyl acetate (EtOAc, 15.0 L) were charged to a reactor. Separately, an aqueous $NaHSO_3$ solution was prepared by thoroughly mixing $NaHSO_3$ (1500 g) and potable water (8.0 L). The aqueous $NaHSO_3$ solution was added to the reaction mixture, heated to 65° C.-70° C., and stirred at 65° C.-70° C. for about 2.5 hours. The phases were separated and the organic phase was kept in the reactor. Separately, an aqueous $NaHSO_3$ solution was prepared by thoroughly mixing $NaHSO_3$ (1500 g) and potable water (8.0 L). The aqueous $NaHSO_3$ solution was added to the reaction mixture, heated to 65° C.-70° C., and stirred at 65° C.-70° C. for about 3.5 hours. The phases were separated. A chromatography column was loaded sequentially with sea sand (3000 g), ethyl acetate (EtOAc, 15.0 L), and silica gel ($SiO_2$, 4500 g). The silica gel and solvent were mixed and the solvent was eluted to the surface of the silica gel. Sea sand (3000 g) was loaded onto the top of the column. The reaction mixture was loaded onto the column and eluted with ethyl acetate (18.0 L). The desired fractions were combined and the combined solution was concentrated under vacuum at about 55° C. to afford the column purified product (1760 g), which was then charged to the reactor with methylene chloride (16.0 L). Si-thiol (160 g) was charged to the reactor and the reaction mixture was heated to 35° C.-40° C. and stirred at 35° C.-40° C. for about 2 hours. The mixture was filtered and the filter cake was washed with methylene chloride (3.5 L). The combined filtrate and wash solution was concentrated under vacuum to afford the purified desired product, 1'-(1-ethoxy-ethyl)-3,5-dimethyl-1H, 1'H-[4,4']bipyrazolyl (1600 g), which contained residual solvent and was used directly in the subsequent reaction. $^1H$ NMR (400 MHz, DMSO-$d_6$) δ 12.17 (s, 1H), 7.89 (s, 1H), 7.56 (s, 1H), 5.53 (q, J=6.0 Hz, 1H), 3.41 (dq, J=9.6, 7.0 Hz, 1H), 3.19 (dq, J=9.6, 7.0 Hz, 1H), 2.20 (s, 6H), 2.10, 1.60 (d, J=6.0 Hz, 3H), 1.01 (t, J=7.0 Hz, 3H) ppm; $^{13}$C NMR (101 MHz, DMSO-d$_6$) δ 145.7, 137.75, 135.9, 125.48, 114.94, 108.69, 86.84, 63.57, 21.84, 15.43, 13.86 ppm.

Step 2. 3,5-dimethyl-1H, 1'H-[4,4']bipyrazolyl hydrochloride (Compound 2x HCl)

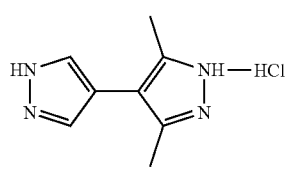

A 100 L glass reactor was purged with nitrogen and charged with 1'-(1-ethoxy-ethyl)-3,5-dimethyl-1H,1'H-[4,4']bipyrazolyl (5723 g, based on theoretical yield), 2-propanol (IPA, 13.0 L), and concentrated hydrochloric acid (HCl, 4.08 L) at room temperature. The resulting reaction mixture was heated to about 60° C.-65° C. and stirred at 60° C.-65° C. for about 2 hours. The reaction mixture was cooled to room temperature and stirred at room temperature for about 1 hour. The solids were collected by filtration and the filter cake was washed with 2-propanol (6.5 L). The product was air-dried to afford the desired product, 3,5-dimethyl-1H,1'H-[4,4']bipyrazolyl hydrochloride (3088 g, 63.6% for two steps), as white solids. $^1$H NMR (400 MHz, DMSO-d$_6$) δ 7.94 (s, 2H), 2.38 (s, 6H) ppm; $^{13}$C NMR (101 MHz, DMSO-d$_6$) δ 141.95, 132.75, 111.78, 109.70, 10.97 ppm.

Step 3. 3,5-dimethyl-1H,1'H-[4,4']bipyrazolyl (Compound 2x)

A 100 L glass reactor was purged with nitrogen and charged with 3,5-dimethyl-1H,1'H-[4,4']bipyrazolyl hydrochloride (3010 g) and potable water (24.1 L), and the reaction mixture was cooled to 0° C.-5° C. Separately, an aqueous NaOH solution was prepared by thoroughly mixing NaOH (1212 g) and potable water (6.0 L). The aqueous NaOH solution was added to the reaction mixture while maintaining the temperature at about 15° C. The reaction mixture was warmed to about 18° C., and stirred at about 18° C. for about 14 hours. The solids were collected by filtration and the filter cake was washed sequentially with potable water (30.1 L) and n-heptane (13.5 L). The product was air-dried for about 16 hours and then further dried under vacuum at about 50° C.-60° C. to afford 3,5-dimethyl-1H, 1'H-[4,4']bipyrazolyl (2006 g, 81.6%) as an off-white powder. $^1$H NMR (400 MHz, DMSO-d$_6$) δ 7.65 (s, 2H), 2.19 (s, 6H) ppm; $^{13}$C NMR (101 MHz, DMSO-d$_6$) δ 140.76, 131.92, 113.44, 109.16, 12.37 ppm.

Intermediate 2. (S)-4-(3-(cyanomethylene)azetidin-1-yl)-2,5-difluoro-N-(1,1,1-trifluoropropan-2-yl)benzamide (Compound 1x)

Scheme 2

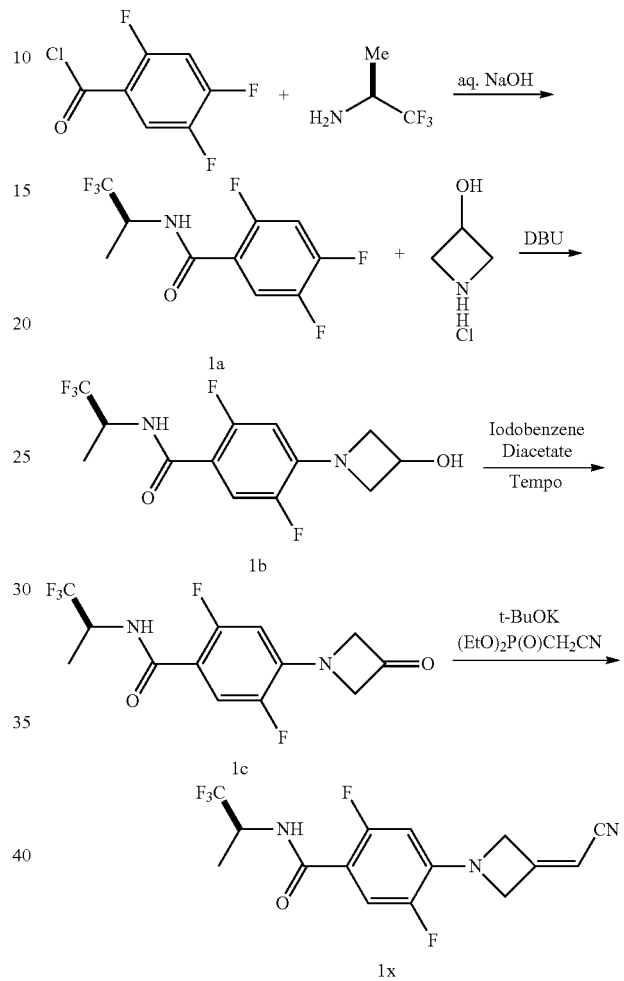

Step 1. (S)-2,4,5-trifluoro-N-(1,1,1-trifluoropropan-2-yl)benzamide (Compound 1a)

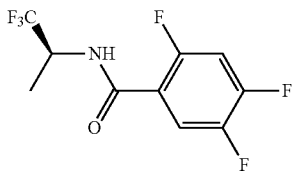 [SMILES: C[C@H](NC(=O)c1cc(F)c(F)cc1F)C(F)(F)F]

A mixture of (2S)-1,1,1-trifluoropropan-2-amine (520.96 g, 4.61 mol) in toluene (9.7 L) was cooled to 0° C.-5° C. before a solution of 1.0 M sodium hydroxide aqueous solution (6.92 L, 6.92 mol, 1.5 equiv) was added at 0° C.-8° C. 2,4,5-Trifluorobenzoyl chloride (995.62 g, 5.07 mol, 1.1 equiv) was then added dropwise to the mixture at 0° C.-15° C. over 20 min. The cooling bath was removed and the reaction mixture was warmed to room temperature and stirred at room temperature for an additional 1 h. The two phases of the reaction mixture were then separated. The organic phase was washed with 0.5 M aqueous sodium hydroxide solution (4.6 L) and concentrated under reduced pressure to afford the crude product as a white solid. The solid was then slurried in n-heptane (2.3 L) at 50° C. for 1 h, then cooled to room temperature. The solids were collected by filtration, washed with n-heptane (1 L), and dried under vacuum for 2 days to give (S)-2,4,5-trifluoro-N-(1,1,1-trifluoropropan-2-yl)benzamide (1203.7 g, 93.2%) as a white powder. $^1$HNMR (300 MHz, DMSO-$d_6$) δ 9.00 (d, J=8.09 Hz, 1H), 7.69 (m, 2H), 4.75 (m, 1H), 1.92 (d, J=7.00 Hz, 3H) ppm.

Step 2. (S)-2,5-difluoro-4-(3-hydroxyazetidin-1-yl)-N-(1,1,1-trifluoropropan-2-yl)benzamide (Compound 1b)

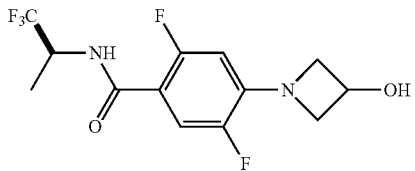 [SMILES: C[C@H](NC(=O)c1cc(F)c(N2CC(O)C2)cc1F)C(F)(F)F]

To a mixture of (S)-2,4,5-trifluoro-N-(1,1,1-trifluoropropan-2-yl)benzamide (Compound 1a, 1807.5 g, 6.67 mol) and azetidin-3-ol hydrochloride (827.9 g, 7.56 mol, 1.13 equiv) in acetonitrile (3.6 L) was added 1,8-diazabicyclo[5.4.0]undec-7-ene (DBU, 2335.2 g, 15.33 mol, 2.3 equiv) in portions. The exothermal reaction raised the internal temperature from 12° C. to 58° C. when the first 1000 g of DBU was charged over 25 minutes. The remaining DBU was added at 58° C.-68° C. over 20 minutes, and the resulting reaction mixture was stirred at 58° C.-68° C. for 1 h. The reaction mixture was then cooled to room temperature and treated with 1.0 M aqueous hydrochloric acid solution (4.34 L). The mixture was stirred at room temperature for 15 minutes and water (6 L) was added. The resulting mixture was stirred at room temperature for 1 h. The solids were collected by filtration, washed with water (2 L), and dried under vacuum for 4 days to afford (S)-2,5-difluoro-4-(3-hydroxyazetidin-1-yl)-N-(1,1,1-trifluoropropan-2-yl)benzamide (2009.8 g, 93.0%) as a white powder. $^1$H-NMR (300 MHz, DMSO-$d_6$) δ 8.38 (d, J=8.71 Hz, 1H), 7.26 (dd, J=12.91 Hz, 1H), 6.38 (dd, J=12.29 Hz, 1H), 5.70 (d, J=6.38, 1H), 4.75 (m, 1H), 4.56 (m, 1H), 4.22 (m, 2H), 3.71 (m, 2H), 1.28 (d, J=7.16, 3H) ppm.

Step 3. (S)-2,5-difluoro-4-(3-oxoazetidin-1-yl)-N-(1,1,1-trifluoropropan-2-yl)benzamide (Compound 1c)

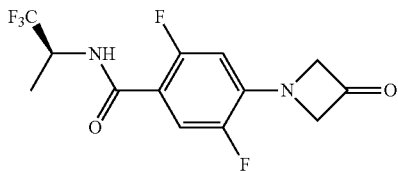

A solution of 2,5-difluoro-4-(3-hydroxyazetidin-1-yl)-N-[1S)-2,2,2-trifluoro-1-methylethyl]benzamide (Compound ib, 1672.6 g, 5.16 mol) and iodobenzene diacetate (1923.5 g, 5.98 mol, 1.16 equiv) in methylene chloride (8.5 L) was added to 2,2,6,6-tetramethyl-1-piperidinyloxy free radical (TEMPO, 20.9 g, 0.13 mol, 0.025 equiv) at 10° C.-12° C. The resulting reaction mixture was stirred at 10° C.-12° C., with the internal temperature reaching 36° C.-38° C. over 30-60 minutes. A cooling bath of IPA and dry ice was used to control the reaction temperature. Once the internal mixture temperature was reduced to below 25° C., the reaction mixture was then heated to 35° C.-38° C. and stirred at 35° C.-38° C. for an additional 2-3 hours. The reaction mixture was then cooled to room temperature and quenched with an aqueous solution (8.0 L) of sodium thiosulfate (82.9 g, 0.52 mol) and potassium phosphate (950.0 g, 4.5 mol). Two phases were separated and the organic phase was washed with water (2×4 L). The organic solution was then concentrated under reduced pressure to afford the crude desired product as a solid. The solid was slurried in n-heptane (10 L) at room temperature for 30 minutes. The solids were collected by filtration, washed with n-heptane (2×2 L), and dried under vacuum overnight to give (S)-2,5-difluoro-4-(3-oxoazetidin-1-yl)-N-(1,1,1-trifluoropropan-2-yl)benzamide (1552.1 g, 93.4%) as a tan powder. $^1$H-NMR (300 MHz, DMSO-$d_6$) δ 8.50 (d, J=8.72 Hz, 1H), 7.35 (dd, J=12.6 Hz, 1H), 6.62 (dd, J=12.1 Hz, 1H), 4.81 (s, 4H), 4.56 (m, 1H), 1.30 (d, J=7.0 Hz, 3H) ppm.

Step 4. (S)-4-(3-(cyanomethylene)azetidin-1-yl)-2,5-difluoro-N-(1,1,1-trifluoropropan-2-yl)benzamide (Compound 1x)

Diethyl cyanomethylphosphonate (422.6 g, 2.39 mol, 0.98 equiv) was added to a solution of 1.0 M potassium tert-butoxide in THF (1996.6 g, 2.27 mol, 0.94 equiv) and under nitrogen, over 10 min at 5° C.-25° C. The resulting mixture was then warmed to room temperature and stirred for 1 h to generate a clear (Solution A). Under nitrogen, [2,5-difluoro-4-(3-oxoazetidin-1-yl)-N-[(1S)-2,2,2-trifluoro-1-methylethyl]benzamide (Compound 1c, 784.2 g, 2.43 mol) was added to a mixture of ethanol (EtOH, 0.75 L) and tetrahydrofuran (THF, 2.9 L) to form a solution (Solution B). The resulting Solution B was then cooled to −5° C. in a dry ice-IPA bath, and Solution A was added to Solution B over 30 minutes at −5° C.-5° C. The resulting mixture was stirred at 0° C.-5° C. for 60 minutes. The reaction mixture was then quenched by addition of water (9.4 L) over 10 minutes. The resulting mixture was stirred at room temperature for 60 minutes. The solids were then collected by filtration and washed with water (2 L) and n-heptane (2.4 L) to give a brown powder. The brown solids were slurried in methyl tent-butyl ether (MTBE, 4 L), overnight at room temperature. The solids were collected by filtration, washed with MTBE (1 L), and dried under vacuum for 3 days to give (S)-4-(3-(cyanomethylene)azetidin-1-yl)-2,5-difluoro-N-(1,1,1-trifluoropropan-2-yl)benzamide (671.1 g, 94%) as an off-white powder. $^1$H-NMR (300 MHz, DMSO-$d_6$) δ 8.50 (d, J=9.95 Hz, 1H), 7.31 (dd, J=12.4 Hz, 1H), 6.58 (dd, J=12.0 Hz, 1H), 5.88 (m, 1H), 4.86-4.75 (m, 5H), 1.31 (d, J=7.0 Hz, 3H) ppm.

Intermediate 3. tert-Butyl 3-(cyanomethylene)azetidine-1-carboxylate (Compound 1y)

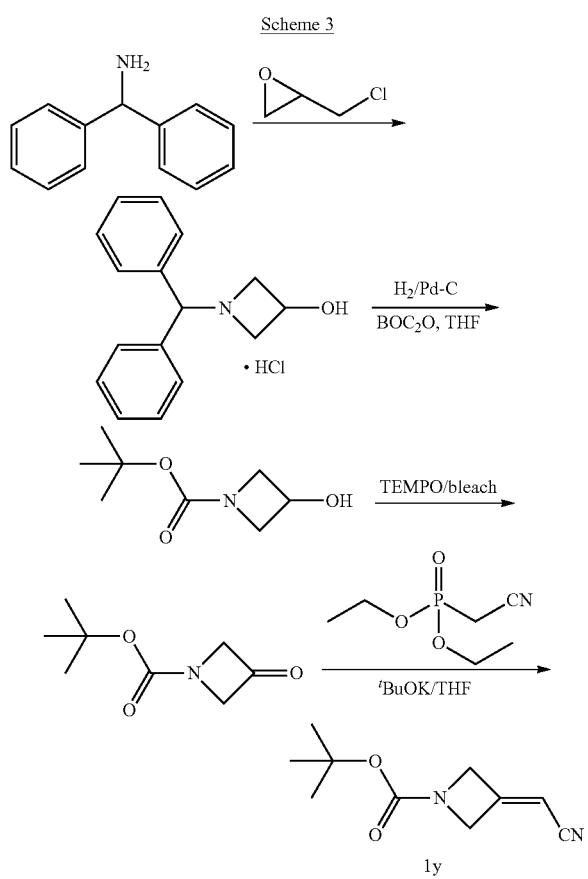

Step 1. 1-Benzhydrylazetidin-3-ol hydrochloride

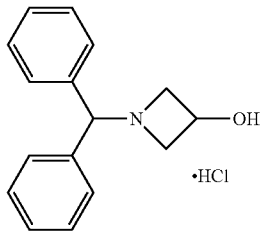 [SMILES: OC1CN(C(c2ccccc2)c2ccccc2)C1 ; Cl]

A solution of diphenylmethanamine (2737 g, 15.0 mol, 1.04 equiv) in methanol (MeOH, 6 L) was treated with 2-(chloromethyl)oxirane (1330 g, 14.5 mol) at ambient temperature. The resulting reaction mixture was stirred at room temperature for 3 days then warmed to reflux for an additional 3 days. The reaction mixture was next cooled to room temperature and then to 0° C.-5° C. in an ice bath. The solids were collected by filtration and washed with acetone (4 L) to give the first crop of the crude desired product (1516 g). The filtrate was concentrated under reduced pressure and the resulting semisolid was diluted with acetone (1 L). This solid was then collected by filtration to give the second crop of the crude desired product (221 g). The crude product, 1-benzhydrylazetidin-3-ol hydrochloride (1737 g, 43.4% yield), was used in the subsequent reaction without further purification. $^1$HNMR (300 MHz, DMSO-$d_6$) δ 12.28 (br. d, 1H), 7.7 (m, 5H), 7.49 (m, 5H), 6.38 (d, 1H), 4.72 (br. s, 1H), 4.46 (m, 1H), 4.12 (m, 2H), 3.85 (m, 2H) ppm; $C_{16}H_{18}ClNO$ (MW 275.77; $C_{16}H_{17}NO$ for free base, MW, 239.31), LCMS (EI) m/e 240 ($M^+$+H).

Step 2. tert-Butyl 3-hydroxyazetidine-1-carboxylate

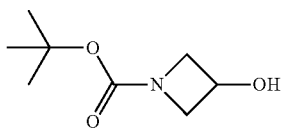

A suspension of 1-benzhydrylazetidin-3-ol hydrochloride (625 g, 2.27 mol) in a 10% solution of aqueous sodium carbonate ($Na_2CO_3$, 5 L) and dichloromethane ($CH_2Cl_2$, 5 L) was stirred at room temperature until all solids were dissolved. The two layers were separated, and the aqueous layer was extracted with dichloromethane ($CH_2Cl_2$, 2 L). The combined organics extracts were dried over sodium sulfate ($Na_2SO_4$) and concentrated under reduced pressure. The resulting crude 1-benzhydrylazetidin-3-ol free base was then dissolved in THF (6 L) and the solution was placed into a large Parr bomb. Di-tent-butyl dicarbonate ($BOC_2O$, 545 g, 2.5 mol, 1.1 equiv) and 20% palladium (Pd) on carbon (125 g, 50% wet) were added to the Parr bomb. The vessel was charged to 30 psi with hydrogen gas ($H_2$) and stirred under steady hydrogen atmosphere (the vessel was recharged three times to maintain the pressure at 30 psi) at room temperature for 18 h. The reaction mixture was filtered through a Celite pad and the Celite pad was washed with THF (4 L). The filtrates were concentrated under reduced pressure to remove the solvent and the residue was loaded onto a Biotage 150 column with a minimum amount of dichloromethane ($CH_2Cl_2$). The column was eluted with 20%-50% ethyl acetate in n-heptane and the fractions containing the pure desired product, tent-butyl 3-hydroxyazetidine-1-carboxylate, were collected and combined. The solvents were removed under reduced pressure to afford tent-butyl 3-hydroxyazetidine-1-carboxylate (357 g, 90.8% yield) as a colorless oil, which solidified upon standing at ambient temperature in vacuum. $^1$HNMR (300 MHz, $CDCl_3$), δ 4.56 (m 1H), 4.13 (m, 2H), 3.81 (m, 2H), 1.43 (s, 9H) ppm.

Step 3. tert-Butyl 3-oxoazetidine-1-carboxylate

A solution of tent-butyl 3-hydroxyazetidine-1-carboxylate (50 g, 289 mmol) in ethyl acetate (400 mL) was cooled to 0° C. The resulting solution was then treated with solid TEMPO (0.5 g, 3.2 mmol, 0.011 equiv) and a solution of potassium bromide (KBr, 3.9 g, 33.2 mmol, 0.115 equiv) in water (60 mL) at 0° C.-5° C. While keeping the reaction temperature between 0° C.-5° C., a solution of saturated aqueous sodium bicarbonate (NaHCO$_3$, 450 mL) and an aqueous sodium hypochlorite solution (NaClO, 10%-13% available chlorine, 450 mL) were added. When additional amount of sodium hypochlorite solution was added, the color of the reaction mixture gradually faded. When the starting material was consumed, the color of the reaction mixture no longer changed. The reaction mixture was then diluted with ethyl acetate (EtOAc, 500 mL) and two layers were separated. The organic layer was washed with water (500 mL) and the saturated aqueous sodium chloride solution (500 mL) and dried over sodium sulfate (Na$_2$SO$_4$). The solvent was then removed under reduced pressure to give the crude product, tent-butyl 3-oxoazetidine-1-carboxylate (48 g, 49.47 g theoretical, 97% yield), which was used directly in the next step without further purification. $^1$HNMR (CDCl$_3$, 300 MHz) δ 4.65 (s, 4H), 1.42 (s, 9H) ppm.

Step 4. tert-Butyl 3-(cyanomethylene)azetidine-1-carboxylate

Diethyl cyanomethyl phosphate (745 g, 4.20 mol, 1.20 equiv) and anhydrous tetrahydrofuran (THF, 9 L) were added to a four-neck flask at room temperature. The solution was cooled with an ice-methanol bath to −14° C. and a 1.0 M solution of potassium tert-butoxide (t-BuOK) in anhydrous tetrahydrofuran (THF, 3.85 L, 3.85 mol, 1.1 equiv) was added over 20 min, keeping the reaction temperature below −5° C. The resulting reaction mixture was stirred for 3 hours at −10° C. and a solution of 1-tert-butoxycarbonyl-3-azetidinone (600 g, 3.50 mol) in anhydrous tetrahydrofuran (THF, 2 L) was added over 2 h, keeping the internal temperature below −5° C. The reaction mixture was stirred at −5° C. to −10° C. over 1 h and then slowly warmed to room temperature and stirred at room temperature for overnight. The reaction mixture was then diluted with water (4.5 L) and saturated aqueous sodium chloride solution (NaCl, 4.5 L) and extracted with ethyl acetate (EtOAc, 2×9 L). The combined organic layers were washed with brine (6 L) and dried over anhydrous sodium sulfate (Na$_2$SO$_4$). The solvent was removed under reduced pressure and the residue was diluted with dichloromethane (CH$_2$Cl$_2$, 4 L) before being absorbed onto silica gel (SiO$_2$, 1.5 kg). The crude product, which was absorbed on silica gel, was purified by flash column chromatography (SiO$_2$, 3.5 kg, 0%-25% EtOAc and n-hexanes gradient elution) to afford tent-butyl 3-(cyanomethylene)azetidine-1-carboxylate (414.7 g, 61% yield) as white solids. $^1$H NMR (300 MHz, CDCl$_3$) δ 5.40 (m, 1H), 4.70 (m, 2H), 4.61 (m, 2H), 1.46 (s, 9H) ppm; C$_{10}$H$_{14}$N$_2$O$_2$ (MW, 194.23), LCMS (EI) m/e 217 (m$^+$+Na).

Intermediate 4. Alternative Synthesis of (S)-2,4,5-trifluoro-N-(1,1,1-trifluoropropan-2-yl)benzamide (Compound 1a)

Scheme 4.

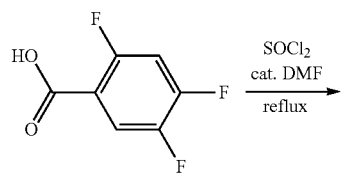

Step 1. 2,4,5-trifluorobenzoyl chloride

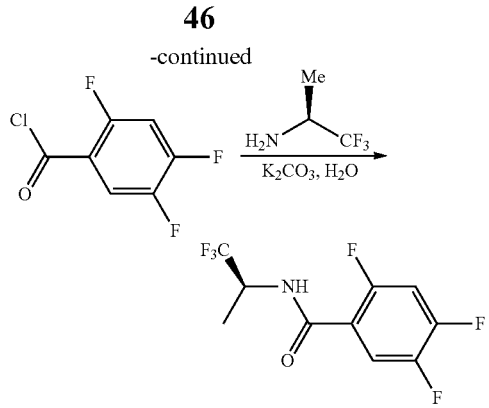

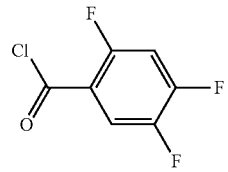 [SMILES: O=C(Cl)c1cc(F)c(F)cc1F]

In a 100 L reactor was charged SOCl$_2$ (34.9 kg), DMF (0.34 L), and 2,4,5-trifluorobenzoic acid (32.3 kg). The batch was heated to 80° C. and stirred at 80° C.-90° C. for 9 hours. The batch was cooled to 50° C.-60° C., and distilled under vacuum at 60° C. until distillation stopped. 14 kg of toluene was charged to the reactor and the batch was continually distilled at 60° C. to afford the crude product, 2,4,5-trifluorobenzoyl chloride (46.28 kg, 88% by HPLC), which was used directly in the next reaction.

Step 2. (S)-2,4,5-trifluoro-N-(1,1,1-trifluoropropan-2-yl)benzamide (Compound 1a)

An aqueous solution (158 L) containing (S)-1,1,1-trifluoropropan-2-amine hydrochloride salt (35 kg) was charged to a 1000 L reactor, and toluene (198 kg) was charged to the reactor followed by portion-wise addition of K$_2$CO$_3$ (82 kg). 2,4,5-trifluorobenzoyl chloride (36.1 kg) was dissolved in toluene (40 kg), and the toluene solution was charged to the reactor with the toluene solution of amine intermediate. The resulting mixture was stirred at 20° C. for 2 hours. The batch was filtered and the filter cake was washed with toluene (117 kg). The filtrate and wash were charged to a 1000 L reactor, and 1N aqueous NaOH solution (125 kg) was charged to the reactor. The mixture was stirred for 2 hours and the phases were allowed to split. The aqueous phase was discarded, and the organic phase was washed twice with water (135 kg) and stored in a clean container (solution 1). A separate portion (portion 2) was treated at the same way to afford solution 2. Solution 1 and solution 2 were charged to a 1000 L reactor, and Na$_2$SO$_4$ (104 kg) was charged to the reactor. The mixture was stirred for 2 hours, filtered, and the filter cake was washed with toluene (90 kg). The filtrate and wash were charged to a 500 L reactor, and the batch was distilled under vacuum at 50° C. Toluene (14 kg) and heptane (166 kg) were charged to the 500 L reactor and the batch was stirred at 80° C. until a solution was obtained. The solution was cooled to 25° C. and stirred for 2 hours. The product was isolated by vacuum filtration, and the filter cake was washed with n-heptane (40 kg). The filter cake was dried under vacuum at ≤50° C. to afford the crude product, (S)-2,4,5-trifluoro-N-(1,1,1-trifluoropropan-2-yl)benzamide (87.0 kg; 79.0 wt % by LOD; net weight: 68.7 kg; 68%; 69.4% by HPLC; 97.1 ee % by chiral HPLC), which was further purified from a mixture of IPA and n-heptane according to the following procedures.

To a 500 L reactor was charged IPA (30.5 kg), heptane (213 kg) and crude (S)-2,4,5-trifluoro-N-(1,1,1-trifluoropropan-2-yl)benzamide (70 kg). The mixture was heated to 85° C. and stirred to form a clear solution. The batch was cooled to 20° C., and stirred for 12 hours. The batch was filtered, and the filter cake was washed with n-heptane (48 kg), and dried under vacuum at 50° C. to afford the purified product, (S)-2,4,5-trifluoro-N-(1,1,1-trifluoropropan-2-yl)benzamide (37.5 kg, 54%; HPLC purity: 98.8%; 99.7 ee % by chiral HPLC). $^1$HNMR (300 MHz, CDCl$_3$) δ 7.96 (m, 1H), 7.01 (m, 1H), 6.71 (m, 1H), 4.93 (m, 1H), 1.44 (d, J=8.00 Hz, 3H) ppm.

Example 1

Synthesis of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (Compound 1 phosphoric acid salt)

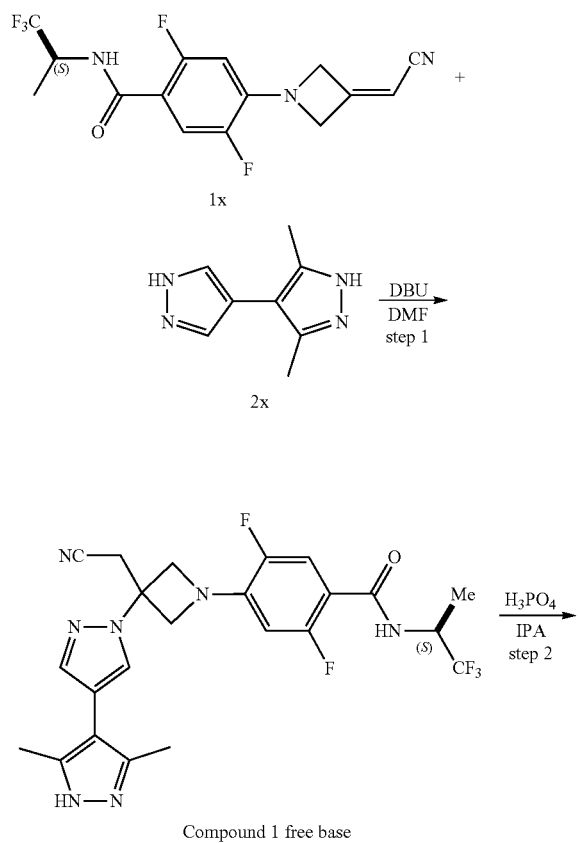

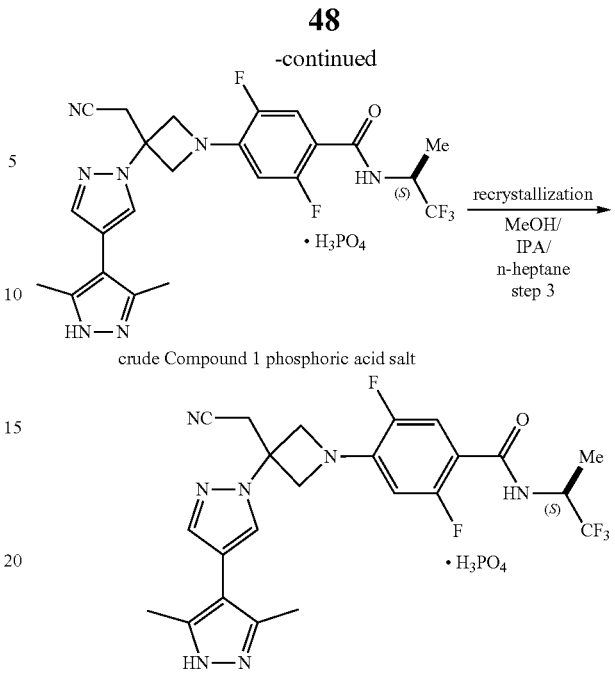

Step 1. 4-[3-(cyanomethyl)-3-(3',5'-dimethyl-1H, 1'H-4,4'-bipyrazol-1-yl)azetidin-1-yl]-2,5-difluoro-N-[(1S)-2,2,2-trifluoro-1-methylethyl]benzamide (Compound 1 free base)

3,5-dimethyl-1H,1'H-[4,4']bipyrazolyl hydrochloride (Compound 2x HCl, 2002 g, 12.34 mol, 1.1 equiv), DMF (3.9 L), and DBU (0.201 L, 204.6 g, 1.34 mol, 0.12 equiv) were charged to a 50 L reactor and the reaction mixture was heated to 50° C.-60° C. and stirred for about 30 minutes. Separately, a solution was prepared by thoroughly mixing (S)-4-(3-(cyanomethylene)azetidin-1-yl)-2,5-difluoro-N-(1,1,1-trifluoropropan-2-yl)benzamide (Compound 1x, 3872 g, 11.21 mol) and DMF (11.6 L). The solution of Compound 1x in DMF was then added to the reaction mixture while maintaining the temperature at about 61° C. The resulting reaction mixture was stirred at about 60° C. for about 3.5 hours. The reaction mixture was then cooled to room temperature and water (77.4 L) was added to the reactor. The cooled reaction mixture was added to the water while maintaining the temperature at about 21° C. The resulting mixture was stirred at room temperature for about 1.5 hours. The solids were collected by filtration and the filter cake was washed with potable water (38.7 L). The wet cake was air-dried to afford 40[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (Compound 1 free base, 5849 g).

A chromatography column was loaded sequentially ethyl acetate (9.9 L), CH$_2$Cl$_2$ (22.4 L) and silica gel (8000 g), mixed thoroughly, and eluted to the surface of the silica gel. Crude Compound 1 free base (1006 g), silica gel (4000 g), and CH$_2$Cl$_2$ (8.0 L) were charged to a first rotary evaporator and rotated at about 22° C. for about 45 minutes without solvent collection. Crude Compound 1 free base (1008 g) and silica gel (4002 g) and CH$_2$Cl$_2$ (8.0 L) were charged to a second rotary evaporator and rotated at about 23° C. for about 45 minutes without solvent collection. Both mixtures were then concentrated at about 34° C. under reduced pressure, and the residues were loaded onto the column. Sea sand (5010 g) was loaded onto the column. The column was eluted sequentially with the collected eluent (16 L), 30% (v/v) EtOAc-CH$_2$Cl$_2$ (prepared separately from 31.2 L of EtOAc and 72.8 L of CH$_2$Cl$_2$), 5% (v/v) MeOH-CH$_2$Cl$_2$ (prepared separately from 2.5 L of MeOH and 47.5 L of CH$_2$Cl$_2$), and 8% (v/v) MeOH-CH$_2$Cl$_2$ (prepared separately from 4.8 L of MeOH and 55.2 L of CH$_2$Cl$_2$). The combined fractions were concentrated under reduced pressure at about 45° C. to afford pure Compound 1 free base (1824 g). Four batches of the column purification were performed to afford 5181 g of pure 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (Compound 1 free base; 91% yield). $^1$H NMR (400 MHz, DMSO-d$_6$) δ 12.22 (s, 1H), 8.50 (d, J=8.7 Hz, 1H), 8.13 (s, 1H), 7.72 (s, 1H), 7.36 (dd, J=12.5, 6.3 Hz, 1H), 6.62 (dd, J=11.9, 7.3 Hz, 1H), 4.78 (m, 1H), 4.64 (d, J=8.9 Hz, 2H), 4.40 (d, J=9.1 Hz, 2H), 3.66 (s, 2H), 2.23 (s, 6H), 1.31 (d, J=7.0 Hz, 3H) ppm; $^{13}$C NMR (101 MHz, DMSO-d$_6$) δ 162.8, 156.7 (d, J=246.6 Hz), 146.9 (d, J=236.9 Hz), 145.2, 141.6 (t, J=12.3 Hz), 138.3, 135.5, 125.8 (q, J=281.9 Hz), 125.6, 117.2, 116.4 (d, J=26.4 Hz), 115.2, 111.3 (dd, J=15.7, 5.8 Hz), 107.7, 102.0 (d, J=29.1 Hz), 62.4, 57.7, 45.8 (q, J=30.8 Hz), 27.0, 13.3, 13.3, 10.4 ppm; $^{19}$F NMR (282 MHz, DMSO-d$_6$) δ −76.17 (d, J=7.4 Hz), −116.89 (s), −139.71 (s) ppm.

Step 2. 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (crude Compound 1 phosphoric acid salt)

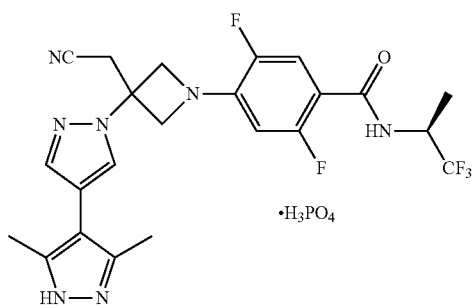

To a clear solution of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide (Compound 1 free base, 405.0 g, 798.1 mmol) in methanol (MeOH, 520.0 mL) and 2-propanol (IPA, 2550.0 mL) at 50° C. was added a solution of phosphoric acid (85 wt % aqueous, 119.65 g, 1037.8 mmol, 1.3 equiv) in isopropyl alcohol (IPA, 120.0 mL) over 18 minutes. The resulting slurry was stirred at 50° C. for 1 h. n-Heptane (4050.0 mL) was then added over 40 min while maintaining the internal temperature between 46° C.-53° C. After the addition of n-heptane, the slurry was cooled to room temperature and stirred for 19 h. The solids were collected by filtration, washed with a mixture of 2-propanol/and n-heptane (3 to 10 by volume, 2×700 mL) followed by n-heptane (3×550 mL), and dried under vacuum at room temperature to afford crude 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (crude Compound 1 phosphoric acid salt, 434.6 g, 89.9% yield).

Step 3. 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (Compound 1 phosphoric acid salt, purified)

4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (crude Compound 1 phosphoric acid salt, 958.3 g, 1583 mmol) and methanol (MeOH, 9583.0 mL) were charged to a 22 L flask at room temperature. The resulting slurry was heated to 50° C. to give a clear light orange solution. The solution was polish filtered, transferred to a 22 L flask and heated to remove the methanol over 70 min. 2-Propanol (IPA, 7700 mL) was then added to the flask over 30 min while maintaining the internal temperate between 50° C.-65° C. n-Heptane (14400 mL) was then added portion-wise while maintaining a distillation of the solvent mixture (MeOH, IPA, and n-heptane) over 2.5 h. A total of 10818 g (15000 mL) of the solvent mixture was distilled. The resulting slurry was cooled to room temperature and stirred for 17 h. The solids were collected by filtration, washed with a mixture of 2-propanol (IPA) and n-heptane (1 to 5 by volume, 3000 mL) followed by n-heptane (3×4000 mL), and dried under vacuum at room temperature to afford 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (Compound 1 phosphoric acid salt, 925.7 g, 96.6% yield) as off-white crystalline powder. $^1$H NMR (400 MHz, DMSO-d$_6$) δ 9.35 (br. s, 4H), 8.50 (d, J=8.9 Hz, 1H), 8.11 (s, 1H), 7.70 (s, 1H), 7.34 (dd, J=12.5, 6.4 Hz, 1H), 6.61 (dd, J=12.0, 7.4 Hz, 1H), 4.86-4.69 (m, 1H), 4.61 (d, J=8.9 Hz, 2H), 4.38 (d, J=8.9 Hz, 2H), 3.64 (s, 2H), 2.21 (s, 6H), 1.30 (d, J=7.1 Hz, 3H) ppm; $^{13}$C NMR (100 MHz, DMSO-d$_6$) δ 162.8, 156.7 (d, J$_{CF}$=246.5 Hz), 146.9 (d, J$_{CF}$=236.1 Hz), 141.6 (dd, J$_{CF}$=13.0, 11.7 Hz), 140.3, 138.3, 125.8 (q, J$_{CF}$=281.8 Hz), 125.6, 117.2, 116.4 (dd, J$_{CF}$=22.3, 4.6 Hz), 115.1, 111.3 (dd, J$_{CF}$=15.7, 5.8 Hz), 107.7, 102.0 (dd, J$_{CF}$=29.5, 4.5 Hz), 62.3, 57.7, 57.7, 45.8 (q, J$_{CF}$=30.5 Hz), 27.0, 13.3 (d, J$_{CF}$=1.7 Hz), 11.7 ppm; C$_{23}$H$_{22}$F$_5$N$_7$O (MW 507.46), LCMS (EI) m/e 508.1 (M$^+$+H).

Figure 2:
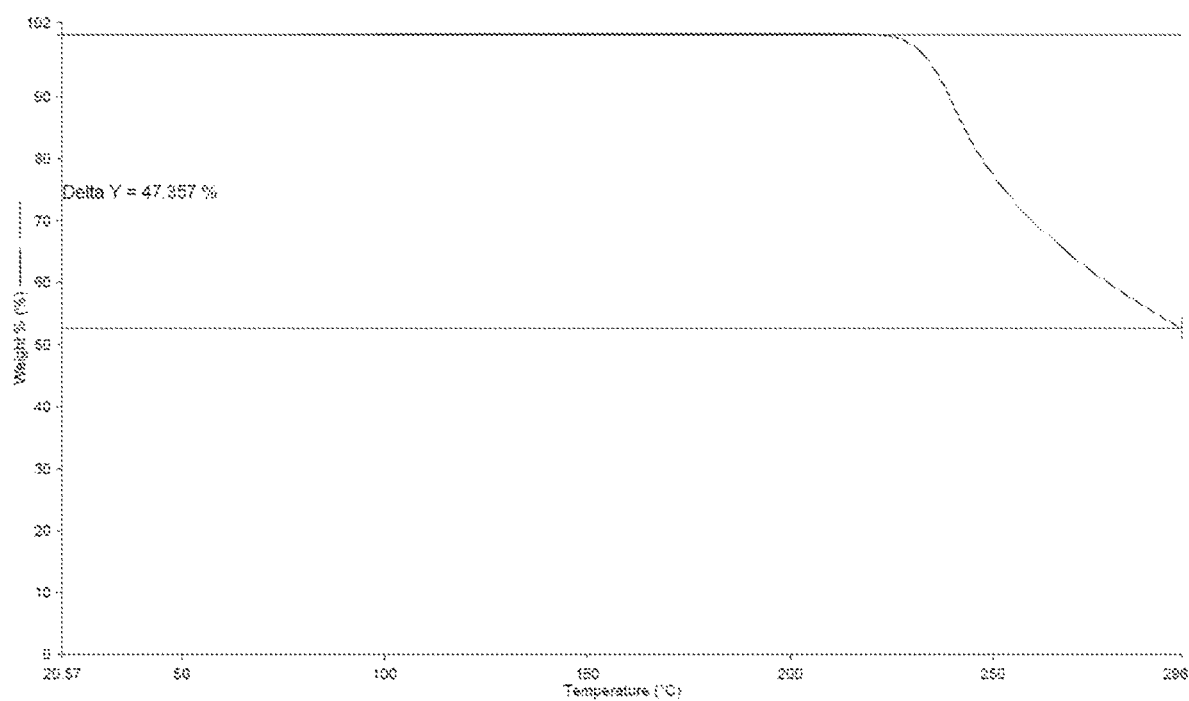
FIG. 2 shows a representative thermogravimetric analysis (TGA) trace for Compound 1 phosphoric acid, prepared according to the process described in Example 1.
Figure 3:
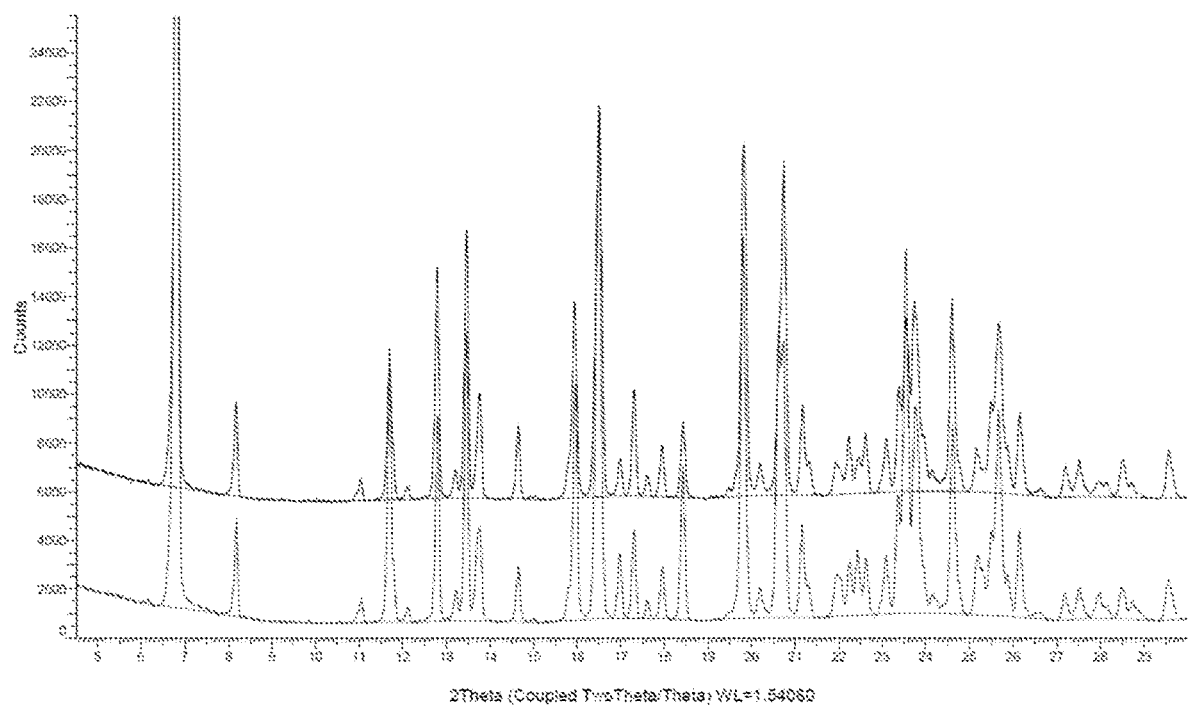
FIG. 3 shows a representative X-ray powder diffraction (XRPD) trace for Compound 1 phosphoric acid, prepared according to the process described in Example 1, overlaid

The phosphoric acid salt ratio was measured by $^1$H NMR at 1.01 phosphoric acid to Compound 1 free base. The same crystalline form of Compound 1 phosphoric acid salt drug substance has been consistently prepared following the preparation and purification procedures described above. This form has been confirmed by differential scanning calorimetry (DSC) as shown in FIG. 1, thermogravimetric analysis (TGA) as shown in FIG. 2, and X-ray powder diffraction (XRPD) as shown in FIG. 3.

Example 2

Alternative Synthesis of 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide phosphoric acid salt (Compound 1 phosphoric acid salt)

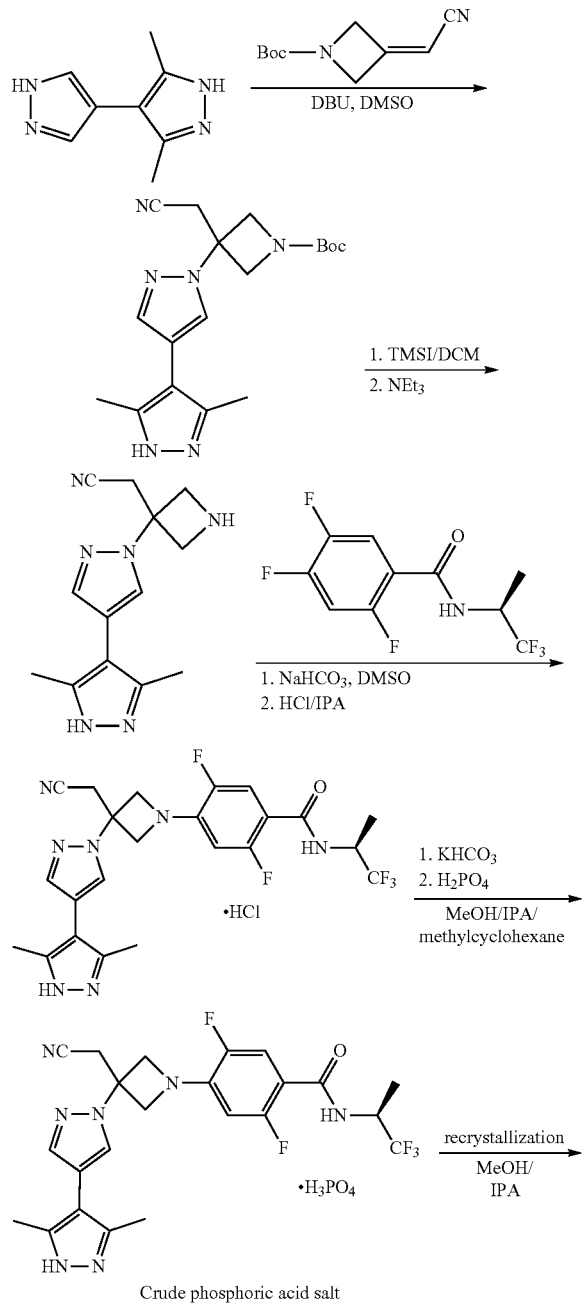

Crude phosphoric acid salt

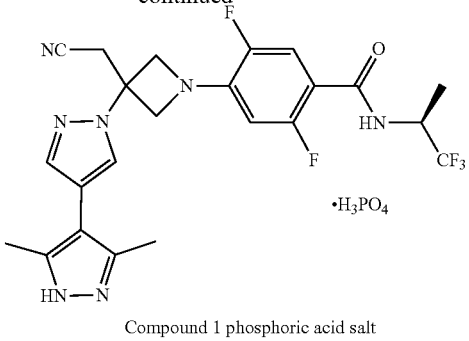

Compound 1 phosphoric acid salt

Step 1. tent-Butyl 3-(cyanomethyl)-3-(3',5'-dimethyl-1H,1'H-[4,4'-bipyrazol]-1-yl)azetidine-1-carboxylate

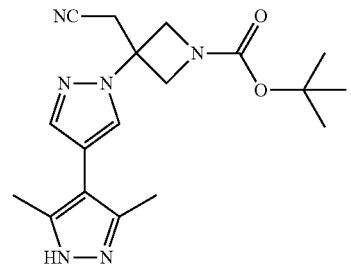 [SMILES: Cc1n[nH]c(C)c1-c1cnn(C2(CC#N)CN(C(=O)OC(C)(C)C)C2)c1]

To a 250 L glass lined dried reactor was charged anhydrous dimethyl sulfoxide (DMSO; 57.0 L), which was heated to 32° C. Once the solvent was at temperature, tert-butyl 3-(cyanomethylene)azetidine-1-carboxylate (Compound 1y, 22.8 kg, 117.4 mol, 1.0 equiv) was charged to the reaction vessel, followed by 3,5-dimethyl-4,4'-bipyrazole (Compound 2x, 20.0 kg, 123.3 mol, 1.05 equiv). The reaction mixture was cooled to 24° C., DBU (4.4 L, 29.56 mol, 0.25 equiv) was charged to the reaction vessel, and the resulting solution was stirred for at least 2 hours. The reaction mixture was then diluted with methylene chloride (116 L) and charged to an aqueous solution of 10% citric acid and 10% NaCl (97 L). The lower organic layer was separated from the biphasic mixture and the aqueous layer was extracted with methylene chloride (58 L). The combined organic layers were then washed two times with an aqueous solution of 10% citric acid and 10% NaCl (97 L). As part of the second wash, additional methylene chloride (DCM) was added to the organic layer (58 L). After washing, isopropyl acetate (465 L) was charged to the reaction mixture while performing a constant volume distillation. White solids formed during the distillation. The resulting suspension was cooled to 20° C., stirred for at least 4 hours, filtered, and dried to afford the desired product, tent-butyl 3-(cyanomethyl)-3-(3',5'-dimethyl-1H,1'H-[4,4'-bipyrazol]-1-yl)azetidine-1-carboxylate (30.4 kg, 79%), as a white solid. $^1$H NMR (400 MHz, DMSO-$d_6$) δ 12.19 (s, 1H), 8.06 (s, 1H), 7.70 (s, 1H), 4.41 (d, J=9.4 Hz, 2H), 4.18 (d, J=9.3 Hz, 2H), 3.55 (s, 2H), 2.23 (d, J=19.5 Hz, 6H), 1.41 (s, 9H) ppm; $C_{18}H_{24}N_6O_2$, (MW 356.42), LCMS (EI) m/e 357.4 (M$^+$+H).

Step 2. 2-(3-(3',5'-Dimethyl-1H,1'H-[4,4'-bipyrazol]-1-yl)azetidin-3-yl)acetonitrile

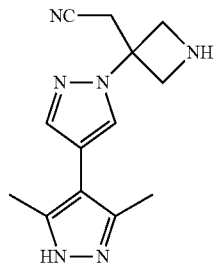 [SMILES: Cc1n[nH]c(C)c1-c1cnn(C2(CC#N)CNC2)c1]

To a 450 L glass lined reactor was charged methylene chloride (300 L) and tert-butyl 3-(cyanomethyl)-3-(3',5'-dimethyl-1H,1'H-[4,4'-bipyrazol]-1-yl)azetidine-1-carboxylate (30.0 kg, 84.17 mol, 1.000 equiv). TMSI (14.4 L, 101.45 mol, 1.205 equiv) was added and the resulting solution was stirred for at least 2 hours at 25° C. Methanol (4.3 L, 106.12 mol, 1.261 equiv) was charged to the reactor and the reaction mixture was stirred for an additional 30 minutes. The reaction mixture was then heated to remove methylene chloride (150 L) by distillation. After the distillation was complete, isopropyl acetate (IPAc, 150 L) was charged to the vessel at 25° C. and the reaction mixture was stirred for 1 hour. The resulting suspension was filtered and washed with IPAc to yield a crude mixture of 2-(3-(3',5'-dimethyl-1H,1'H-[4,4'-bipyrazol]-1-yl)azetidin-3-yl)acetonitrile and 2-(3-(3',5'-dimethyl-1H,1'H-[4,4'-bipyrazol]-1-yl)azetidin-3-yl)acetonitrile dihydroiodic acid salt as yellow solids (68 kg).

The crude solids were then transferred to a 450 L glass-lined reactor charged with methylene chloride (360 L). Triethylamine (14 L, 100.80 mol, 1.198 equiv) was charged to the reactor over 30 min and the resulting mixture was stirred at 25° C. for 12 h. The resulting suspension was filtered, washed once with methylene chloride and three times with IPAc, filtered, and dried to afford the desired product, 2-(3-(3',5'-dimethyl-1H,1'H-[4,4'-bipyrazol]-1-yl)azetidin-3-yl)acetonitrile (16.8 kg, 78%), as a white solid. $^1$H NMR (600 MHz, DMSO-$d_6$) δ 10.16 (q, J=7.0 Hz, 1H), 9.90 (s, 1H), 8.45 (s, 1H), 7.92 (s, 1H), 4.65-4.55 (m, 2H), 4.36-4.25 (m, 2H), 3.88 (s, 2H), 2.41 (s, 6H) ppm; $C_{13}H_{16}N_6$, (MW 256.31), LCMS (EI) m/e 257.2 (M$^+$+H).

Step 3. (S)-4-(3-(Cyanomethyl)-3-(3',5'-dimethyl-1H,1'H-[4,4'-bipyrazol]-1-yl)azetidin-1-yl)-2,5-difluoro-N-(1,1,1-trifluoropropan-2-yl)benzamide hydrochloric acid salt

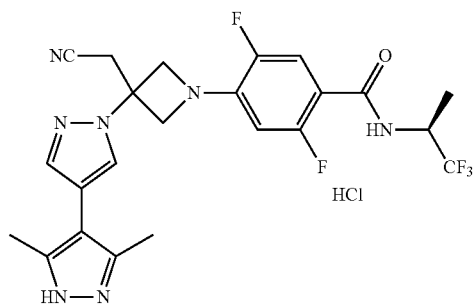 [SMILES: Cc1n[nH]c(C)c1-c1cnn(C2(CC#N)CN(c3cc(F)c(C(=O)N[C@@H](C)C(F)(F)F)cc3F)C2)c1 ; Cl]

To a 250 L glass lined reactor was charged 2-(3-(3',5'-dimethyl-1H,1'H-[4,4'-bipyrazol]-1-yl)azetidin-3-yl)acetonitrile (12 kg, 46.8 mol, 1.00 equiv), (S)-2,4,5-trifluoro-N-(1,1,1-trifluoropropan-2-yl)benzamide (14.6 kg, 53.8 mol, 1.15 equiv), NaHCO$_3$ (4.1 kg, 49.1 mol, 1.05 equiv), LiCl (4.0 kg, 93.6 mol, 2.00 equiv) and DMSO (96 L, 8 V). The resulting reaction mixture was heated to 85° C. for at least 7 hours and the resulting solution was then cooled to room temperature. The reaction mixture was diluted with isopropyl acetate (147 L, 12 V) and then water (120 L, 10 V). The aqueous layer was separated and the remaining organic layer was washed with 1 wt % aqueous citric acid solution (88 L, 7.3 V) and water (88 L, 7.3 V) before being concentrated to approximately 133 L (11 V). Isopropyl Acetate (147 L, 12.25 V) was then added to the mixture while performing a constant volume distillation. Next, a solution of HCl in IPA (2.5 wt %, 96 L, 8 V) was charged to the reactor and the resulting solution was stirred at room temperature. After 1 hour, methylcyclohexane (220 L, 18.1 V) was charged to the slurry and the resulting suspension was stirred at room temperature for an additional 4 hours. The resulting suspension was filtered and the wet cake was washed with a mixture of methylcyclohexane and isopropyl acetate (3:1, 60 L, 5V), followed by methylcyclohexane (60L, 5V). Finally the wet cake was dried at 50° C.-60° C. under vacuum to afford the crude desired product, (S)-4-(3-(cyanomethyl)-3-(3',5'-dimethyl-1H,1'H-[4,4'-bipyrazol]-1-yl)azetidin-1-yl)-2,5-difluoro-N-(1,1,1-trifluoropropan-2-yl)benzamide hydrochloride (22.4 kg, 88%).

Step 4. (S)-4-(3-(Cyanomethyl)-3-(3',5'-dimethyl-1H,1'H-[4,4'-bipyrazol]-1-yl)azetidin-1-yl)-2,5-difluoro-N-(1,1,1-trifluoropropan-2-yl)benzamide phosphoric acid salt

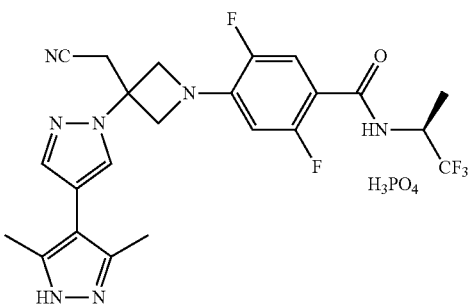

To a 450 L glass lined reactor was charged isopropyl acetate (286 L, 10V) and (S)-4-(3-(cyanomethyl)-3-(3',5'-dimethyl-1H,1'H-[4,4'-bipyrazol]-1-yl)azetidin-1-yl)-2,5-difluoro-N-(1,1,1-trifluoropropan-2-yl)benzamide hydrochloric acid salt (28.6 kg), followed by KHCO$_3$ (86 L, 10 wt % in water, 3V). The suspension was stirred until a clear solution was obtained. Next, the aqueous layer was removed and the organics were washed with water (86 L (3V)) and then filtered over charcoal to a second glass lined reactor. The organics were concentrated to remove 240 L (8.4V) of solvent at 50° C. under reduced pressure of 200 mbar-400 mbar. To the resulting residue was charged isopropanol (163 L, 5.7 V) at 50° C. and subsequently cooled to room temperature. Next, 14.9 kg (52 wt %) of 48 wt % H$_3$PO$_4$ in IPA/water was charged to the reactor over at least 2 hours and the resulting solution was stirred at room temperature for at least 1 hour. Methylcyclohexane (172 L, 6V) was charged at room temperature and the mixture was stirred for at least 1 hour. The suspension was filtered and the cake was washed with 1:1 IPA/methylcyclohexane (86 L, 3 V), followed by methylcyclohexane (86 L, 3 V). The wet cake was then dried at 50° C. under vacuum to afford crude (S)-4-(3-(cyanomethyl)-3-(3',5'-dimethyl-1H,1'H-[4,4'-bipyrazol]-1-yl)azetidin-1-yl)-2,5-difluoro-N-(1,1,1-trifluoropropan-2-yl)benzamide phosphoric acid salt (28.0 kg (88%).

To a 450 L glass lined reactor was charged the crude phosphoric acid salt (28.0 kg) and methanol (336 L (12 V)), and the resulting mixture was heated to 50° C. to afford a clear solution. The solution was transferred into a separate reactor via a polish filter. MeOH (28 L, 1 V) was used to rinse the first reactor and then transferred into the second reactor via polish filter. The filtrate was then concentrated to 7V by distilling 196 L (7 V) of solvent at 45° C. under reduced pressure of 300 mbar-400 mbar. Next, seeds of pure (S)-4-(3-(cyanomethyl)-3-(3',5'-dimethyl-1H,1'H-[4,4'-bipyrazol]-1-yl)azetidin-1-yl)-2,5-difluoro-N-(1,1,1-trifluoropropan-2-yl)benzamide phosphoric acid salt (28.0 g, 0.1 wt %) were charged to the reactor and the mixture was stirred at 45° C. for at least 15 min. Isoprapanol (196 L, 7 V) was charged and 196 L (7 V) of solvents was distilled at around 45° C. under reduced pressure of 100 mbar-200 mbar. Isopropanol (196 L, 7 V) was charged to the reactor and 196 L (7 V) of solvents was removed by distillation. IPC was performed to confirm that methanol was not more than 5% in the mixture. Next, the mixture was cooled to room temperature and the resulting suspension was filtered. The cake was washed twice with isopropanol (56 L, 2V) and then dried at 50° C. under reduced pressure to afford (S)-4-(3-(cyanomethyl)-3-(3',5'-dimethyl-1H,1'H-[4,4'-bipyrazol]-1-yl)azetidin-1-yl)-2,5-difluoro-N-(1,1,1-trifluoropropan-2-yl)benzamide phosphoric acid salt (24.1 kg (86.1%) as a white solid. $^1$H NMR (500 MHz, DMSO-$d_6$) δ 8.53-8.43 (m, 1H), 8.12 (d, J=0.7 Hz, 1H), 7.72 (s, 1H), 7.36 (dd, J=12.5, 6.3 Hz, 1H), 6.63 (dd, J=11.9, 7.2 Hz, 1H), 4.85-4.72 (m, J=7.5 Hz, 1H), 4.64 (d, J=9.0 Hz, 2H), 4.45-4.37 (m, 2H), 3.66 (s, 2H), 2.24 (s, 6H), 1.33 (d, J=7.1 Hz, 3H) ppm; $C_{23}H_{25}F_5N_7O_5P$ (MW 605.45; $C_{23}H_{22}F_5N_7O$: MW 507.47), LCMS (EI) m/e 508.2 (M$^+$+H).

Example A.

In Vitro JAK Kinase Assay

Compounds provided herein are tested for inhibitory activity of JAK targets according to the following in vitro assay described in Park et al., *Analytical Biochemistry* 1999, 269, 94-104. The catalytic domains of human JAK1 (a.a. 837-1142), JAK2 (a.a. 828-1132) and JAK3 (a.a. 781-1124) with an N-terminal His tag is expressed using baculovirus in insect cells and purified. The catalytic activity of JAK1, JAK2 or JAK3 is assayed by measuring the phosphorylation of a biotinylated peptide. The phosphorylated peptide is detected by homogenous time resolved fluorescence (HTRF). $IC_{50}$s of compounds is measured for each kinase in the 40 microL reactions that contain the enzyme, ATP and 500 nM peptide in 50 mM Tris (pH 7.8) buffer with 100 mM NaCl, 5 mM DTT, and 0.1 mg/mL (0.01%) BSA. For the 1 mM $IC_{50}$ measurements, ATP concentration in the reactions is 1 mM. Reactions are carried out at room temperature for 1 hour and then stopped with 20 μL 45 mM EDTA, 300 nM SA-APC, 6 nM Eu-Py20 in assay buffer (Perkin Elmer, Boston, Mass.). Binding to the Europium labeled antibody take place for 40 minutes and HTRF signal is measured on a Fusion plate reader (Perkin Elmer, Boston, Mass.). Compound 1 free base had an $IC_{50}$ of ≤300 nM with a JAK2/JAK1 selectivity of >10 at 1 mM ATP.

Example B

Cellular Assays

Cancer cell lines dependent on cytokines and hence JAK/STAT signal transduction, for growth, can be plated at 6000 cells per well (96 well plate format) in RPMI 1640, 10% FBS, and 1 nG/mL of appropriate cytokine. Compounds provided herein are added to the cells in DMSO/media (final concentration 0.2% DMSO) and incubated for 72 hours at 37° C., 5% $CO_2$. The effect of compound on cell viability is assessed using the CellTiter-Glo Luminescent Cell Viability Assay (Promega) followed by TopCount (Perkin Elmer, Boston, MA) quantitation. Potential off-target effects of compounds are measured in parallel using a non-JAK driven cell line with the same assay readout. All experiments are typically performed in duplicate.

The above cell lines can also be used to examine the effects of compounds provided herein on phosphorylation of JAK kinases or potential downstream substrates such as STAT proteins, Akt, Shp2, or Erk. These experiments can be performed following an overnight cytokine starvation, followed by a brief preincubation with compound (2 hours or less) and cytokine stimulation of approximately 1 hour or less. Proteins are then extracted from cells and analyzed by techniques familiar to those skilled in the art including Western blotting or ELISAs using antibodies that can differentiate between phosphorylated and total protein. These experiments can utilize normal or cancer cells to investigate the activity of compounds on tumor cell survival biology or on mediators of inflammatory disease. For example, with regards to the latter, cytokines such as IL-6, IL-12, IL-23, or IFN can be used to stimulate JAK activation resulting in phosphorylation of STAT protein(s) and potentially in transcriptional profiles (assessed by array or qPCR technology) or production and/or secretion of proteins, such as IL-17. The ability of compounds to inhibit these cytokine mediated effects can be measured using techniques common to those skilled in the art.

Compounds provided herein can also be tested in cellular models designed to evaluate their potency and activity against mutant JAKs, for example, the JAK2V617F mutation found in myeloid proliferative disorders. These experiments often utilize cytokine dependent cells of hematological lineage (e.g. BaF/3) into which the wild-type or mutant JAK kinases are ectopically expressed (James, C., et al. *Nature* 434:1144-1148; Staerk, J., et al. JBC 280:41893-41899). Endpoints include the effects of compounds on cell survival, proliferation, and phosphorylated JAK, STAT, Akt, or Erk proteins.

Compounds provided herein can be evaluated for their activity inhibiting T-cell proliferation. Such as assay can be considered a second cytokine (i.e. JAK) driven proliferation assay and also a simplistic assay of immune suppression or inhibition of immune activation. The following is a brief outline of how such experiments can be performed. Peripheral blood mononuclear cells (PBMCs) are prepared from human whole blood samples using Ficoll Hypaque separation method and T-cells (fraction 2000) can be obtained from PBMCs by elutriation. Freshly isolated human T-cells can be maintained in culture medium (RPMI 1640 supplemented with 10% fetal bovine serum, 100 U/ml penicillin, 100 μg/ml streptomycin) at a density of $2\times10^6$ cells/ml at 37° C. for up to 2 days. For IL-2 stimulated cell proliferation analysis, T-cells are first treated with Phytohemagglutinin (PHA) at a final concentration of 10 μg/mL for 72 hours. After washing once with PBS, 6000 cells/well are plated in 96-well plates and treated with compounds provided herein at different concentrations in the culture medium in the presence of 100 U/mL human IL-2 (ProSpec-Tany Techno-Gene; Rehovot, Israel). The plates are incubated at 37° C. for 72 h and the proliferation index is assessed using CellTiter-Glo Luminescent reagents following the manufactory suggested protocol (Promega; Madison, Wis.).

Example C

In Vivo Anti-Tumor Efficacy

Compounds provided herein can be evaluated in human tumor xenograft models in immune compromised mice. For example, a tumorigenic variant of the INA-6 plasmacytoma cell line can be used to inoculate SCID mice subcutaneously (Burger, R., et al. *Hematol J.* 2:42-53, 2001). Tumor bearing animals can then be randomized into drug or vehicle treatment groups and different doses of compounds provided herein can be administered by any number of the usual routes including oral, i.p., or continuous infusion using implantable pumps. Tumor growth is followed over time using calipers. Further, tumor samples can be harvested at any time after the initiation of treatment for analysis as described above (Example B) to evaluate compound effects on JAK activity and downstream signaling pathways. In addition, selectivity of the compound can be assessed using xenograft tumor models that are driven by other know kinases (e.g. Bcr-Abl) such as the K562 tumor model.

Example D

Murine Skin Contact Delayed Hypersensitivity Response Test

Compounds provided herein can also be tested for their efficacies (of inhibiting JAK targets) in the T-cell driven murine delayed hypersensitivity test model. The murine skin contact delayed-type hypersensitivity (DTH) response is considered to be a valid model of clinical contact dermatitis, and other T-lymphocyte mediated immune disorders of the skin, such as psoriasis (*Immunol Today.* 1998 January; 19(1):37-44). Murine DTH shares multiple characteristics with psoriasis, including the immune infiltrate, the accompanying increase in inflammatory cytokines, and keratinocyte hyperproliferation.

Furthermore, many classes of agents that are efficacious in treating psoriasis in the clinic are also effective inhibitors of the DTH response in mice (Agents Actions. 1993 January; 38(1-2): 116-21).

On Day 0 and 1, Balb/c mice are sensitized with a topical application, to their shaved abdomen with the antigen 2,4, dinitro-fluorobenzene (DNFB). On day 5, ears are measured for thickness using an engineer's micrometer. This measurement is recorded and used as a baseline. Both of the animals' ears are then challenged by a topical application of DNFB in a total of 20 μL (10 μL on the internal pinna and 10 μL on the external pinna) at a concentration of 0.2%. Twenty-four to seventy-two hours after the challenge, ears are measured again. Treatment with compounds provided herein is given throughout the sensitization and challenge phases (day −1 to day 7) or prior to and throughout the challenge phase (usually afternoon of day 4 to day 7). Treatment of the test compound (in different concentration) is administered either systemically or topically (topical application of the treatment to the ears). Efficacies of the test compound are indicated by a reduction in ear swelling comparing to the situation without the treatment. Test compound causing a reduction of 20% or more is considered efficacious. In some experiments, the mice are challenged but not sensitized (negative control).

The inhibitive effect (inhibiting activation of the JAK-STAT pathways) of compounds provided herein can be confirmed by immunohistochemical analysis. Activation of the JAK-STAT pathway(s) results in the formation and translocation of functional transcription factors. Further, the influx of immune cells and the increased proliferation of keratinocytes should also provide unique expression profile changes in the ear that can be investigated and quantified. Formalin fixed and paraffin embedded ear sections (harvested after the challenge phase in the DTH model) are subjected to immunohistochemical analysis using an antibody that specifically interacts with phosphorylated STAT3 (clone 58E12, Cell Signaling Technologies). The mouse ears are treated with compounds provided herein, vehicle, or dexamethasone (a clinically efficacious treatment for psoriasis), or without any treatment, in the DTH model for comparisons. Test compounds and the dexamethasone can produce similar transcriptional changes both qualitatively and quantitatively, and both the test compounds and dexamethasone can reduce the number of infiltrating cells. Both systemically and topical administration of the test compounds can produce inhibitive effects, i.e., reduction in the number of infiltrating cells and inhibition of the transcriptional changes.

Example E

In Vivo Anti-Inflammatory Activity

Compounds provided herein can be evaluated in rodent or non-rodent models designed to replicate a single or complex inflammation response. For instance, rodent models of arthritis can be used to evaluate the therapeutic potential of compounds dosed preventatively or therapeutically. These models include but are not limited to mouse or rat collagen-induced arthritis, rat adjuvant-induced arthritis, and collagen antibody-induced arthritis. Autoimmune diseases including, but not limited to, multiple sclerosis, type I-diabetes mellitus, uveoretinitis, thyroditis, myasthenia gravis, immunoglobulin nephropathies, myocarditis, airway sensitization (asthma), lupus, or colitis may also be used to evaluate the therapeutic potential of compounds provided herein. These models are well established in the research community and are familiar to those skilled in the art (Current Protocols in Immunology, Vol 3., Coligan, J. E. et al, Wiley Press.; *Methods in Molecular Biology*: Vol. 225, Inflammation Protocols., Winyard, P. G. and Willoughby, D. A., Humana Press, 2003.).

Example F

Animal Models for the Treatment of Dry Eye, Uveitis, and Conjunctivitis

Agents may be evaluated in one or more preclinical models of dry eye known to those skilled in the art including, but not limited to, the rabbit concanavalin A (ConA) lacrimal gland model, the scopolamine mouse model (subcutaneous or transdermal), the Botulinumn mouse lacrimal gland model, or any of a number of spontaneous rodent autoimmune models that result in ocular gland dysfunction (e.g. NOD-SCID, MRL/lpr, or NZB/NZW) (Barabino et al., Experimental Eye Research 2004, 79, 613-621 and Schrader et al., Developmental Opthalmology, Karger 2008, 41, 298-312, each of which is incorporated herein by reference in its entirety). Endpoints in these models may include histopathology of the ocular glands and eye (cornea, etc.) and possibly the classic Schirmer test or modified versions thereof (Barabino et al.) which measure tear production. Activity may be assessed by dosing via multiple routes of administration (e.g. systemic or topical) which may begin prior to or after measurable disease exists.

Agents may be evaluated in one or more preclinical models of uveitis known to those skilled in the art. These include, but are not limited to, models of experimental autoimmune uveitis (EAU) and endotoxin induced uveitis (EIU). EAU experiments may be performed in the rabbit, rat, or mouse and may involve passive or activate immunization. For instance, any of a number or retinal antigens may be used to sensitize animals to a relevant immunogen after which animals may be challenged ocuarly with the same antigen. The EIU model is more acute and involves local or systemic administration of lipopolysaccaride at sublethal doses. Endpoints for both the EIU and EAU models may include fundoscopic exam, histopathology amongst others. These models are reviewed by Smith et al. (Immunology and Cell Biology 1998, 76, 497-512, which is incorporated herein by reference in its entirety). Activity is assessed by dosing via multiple routes of administration (e.g. systemic or topical) which may begin prior to or after measurable disease exists. Some models listed above may also develop scleritis/episcleritis, chorioditis, cyclitis, or iritis and are therefore useful in investigating the potential activity of compounds for the therapeutic treatment of these diseases.

Agents may also be evaluated in one or more preclinical models of conjunctivitis known those skilled in the art. These include, but are not limited to, rodent models utilizing guinea-pig, rat, or mouse. The guinea-pig models include those utilizing active or passive immunization and/or immune challenge protocols with antigens such as ovalbumin or ragweed (reviewed in Groneberg, D. A., et al., Allergy 2003, 58, 1101-1113, which is incorporated herein by reference in its entirety). Rat and mouse models are similar in general design to those in the guinea-pig (also reviewed by Groneberg). Activity may be assessed by dosing via multiple routes of administration (e.g. systemic or topical) which may begin prior to or after measurable disease exists. Endpoints for such studies may include, for example, histological, immunological, biochemical, or molecular analysis of ocular tissues such as the conjunctiva.

Example G

In Vivo Protection of Bone

Compounds provided herein can be evaluated in various preclinical models of osteopenia, osteoporosis, or bone resorption known to those skilled in the art. For example, ovariectomized rodents may be used to evaluate the ability of compounds to affect signs and markers of bone remodeling and/or density (W. S. S. Jee and W. Yao, J Musculoskel. Nueron. Interact., 2001, 1(3), 193-207, which is incorporated herein by reference in its entirety). Alternatively, bone density and architecture may be evaluated in control or compound treated rodents in models of therapy (e.g. glucocorticoid) induced osteopenia (Yao, et al. Arthritis and Rheumatism, 2008, 58(6), 3485-3497; and id. 58(11), 1674-1686, both of which are incorporated herein by reference in its entirety). In addition, the effects of compounds provided herein on bone resorption and density may be evaluable in the rodent models of arthritis discussed above (Example E). Endpoints for all these models may vary but often include histological and radiological assessments as well as immunohisotology and appropriate biochemical markers of bone remodeling.

Example H

S100A9 Transgenic Mouse Model

It was previously shown that S100A9 transgenic mice display bone marrow accumulation of MDSC accompanied by development of progressive multilineage cytopenias and cytological dysplasia similar to MDS. Further, early forced maturation of MDSC by either all-trans-retinoic acid treatment or active immunoreceptor tyrosine-based activation motif-bearing (ITAM-bearing) adapter protein (DAP12) interruption of CD33 signaling rescued the hematologic phenotype and mitigated the disease. This system can be useful to test the effects on JAK1 inhibition on MDS-like disease in a preclinical model. *J. Clin. Invest.*, 123(11):4595-4611 (2013), Accordingly, a JAK1 selective inhibitor is dosed by oral gavage. The compound's ability to reduce the cytopenias and cytological dysplasia observed in the S100A9 transgenic mice is monitored.

Various modifications of the disclosure, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:
1. A process of preparing

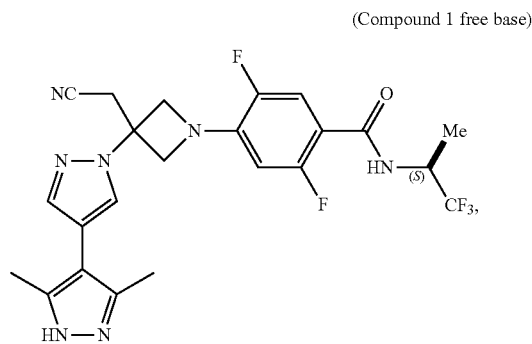

(Compound 1 free base)

or a salt thereof, comprising reacting

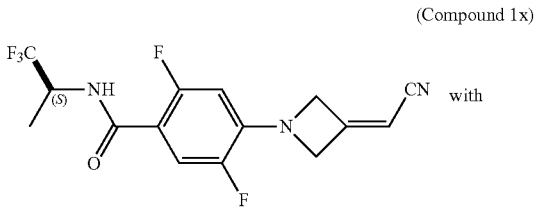

(Compound 1x)

with (Compound 2x)

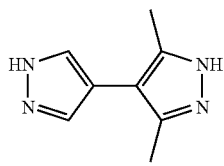

to form Compound 1 free base, or a salt thereof.

2. The process of claim 1, wherein the reacting of Compound 1x with Compound 2x is carried out in the presence of 1,8-diazabicyclo[5.4.0]undec-7-ene (DBU) and an organic solvent component.

3. The process of claim 2, wherein the organic solvent component comprises dimethylformamide (DMF).

4. The process of claim 1, wherein the reacting of Compound 1x with Compound 2x is carried out at a temperature from about 50° C. to about 60° C.

5. The process of claim 4, wherein the temperature is about 60° C.

6. The process of claim 1, wherein the salt of Compound 1 is a phosphoric acid salt of Compound 1 which is prepared by a process comprising reacting Compound 1 free base with phosphoric acid to form (Compound 1 phosphoric acid salt)

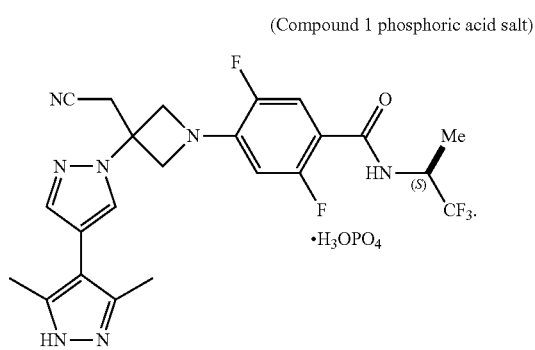

7. The process of claim 6, wherein the reacting of Compound 1 free base with phosphoric acid is carried out in the presence of a solvent component.

8. The process of claim 7, wherein the solvent component comprises methanol, isopropanol, or a mixture thereof.

9. The process of claim 6, wherein the reacting of Compound 1 free base with phosphoric acid is carried out at a temperature from about 40° C. to about 70° C.

10. The process of claim 9, wherein the temperature is from about 45° C. to about 55° C.

11. The process of claim 10, wherein the temperature is about 50° C.

12. The process of claim 6, wherein the phosphoric acid is an aqueous solution of about 85 wt % phosphoric acid.

13. The process of claim 6, wherein the reacting of Compound 1 free base with phosphoric acid further comprises adding a second solvent component to the reaction mixture.

14. The process of claim 13, wherein the second solvent component comprises n-heptane.

15. The process of claim 1, further comprising preparing Compound 2x by a process comprising reacting (Compound 2x HCl)

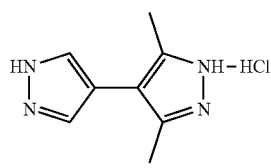

with a base.

16. The process of claim 15, wherein the base is NaOH.

17. The process of claim 15, wherein the reacting of Compound 2x HCl with a base is carried out at a temperature from about 15° C. to about 18° C.

18. The process of claim 15, further comprising preparing Compound 2x HCl by a process comprising reacting (Compound 2b)

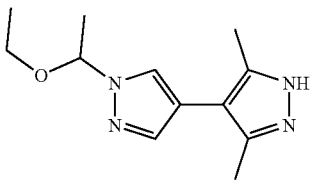

with hydrochloric acid.

19. The process of claim 18, wherein the reacting of Compound 2b with hydrochloric acid is carried out in the presence of an organic solvent component.

20. The process of claim 19, wherein the organic solvent component comprises 2-propanol.

21. The process of claim 18, wherein the reacting of Compound 2b with hydrochloric acid is carried out at a temperature from about 60° C. to about 65° C.

22. The process of claim 18, further comprising preparing Compound 2b by a process comprising reacting (Compound 2a)

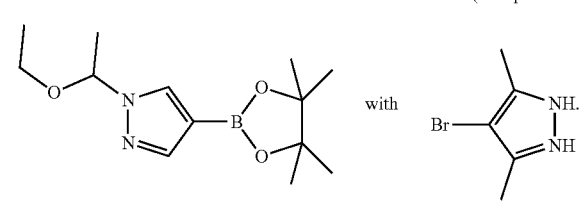

23. The process of claim 22, wherein the reacting of Compound 2a with 4-bromo-3,5-dimethylpyrazole is carried out in the presence of $K_2HPO_4$, solvent component, and a alladium complex.

24. The process of claim 23, wherein the solvent component comprises 1-propanol, water, or a mixture thereof.

25. The process of claim 23, wherein the palladium complex is [1,1'-bis(di-tert-butylphosphino)ferrocene]dichloropalladium(II) (Pd-118).

26. The process of claim 22, wherein the reacting of Compound 2a with 4-bromo-3,5-dimethylpyrazole is carried out at a temperature from about 80° C. to about 100° C.

27. The process of claim 26, wherein the temperature is about 90° C.

28. The process of claim 1, further comprising preparing

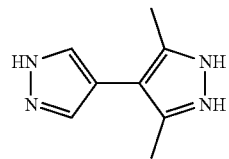 (Compound 2x)

by a process comprising:
reacting

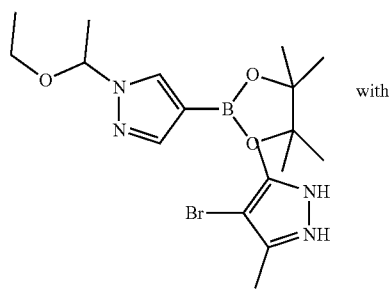 (Compound 2a)

with to form

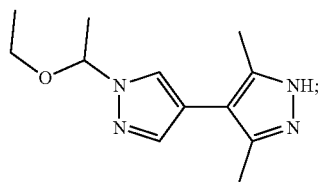 (Compound 2b)

reacting Compound 2b with hydrochloric acid to form

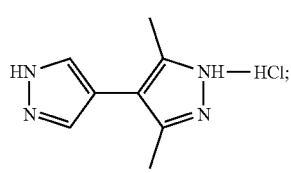 (Compound 2x HCl)

and
reacting Compound 2x HCl with a base to form Compound 2x.

29. The process of claim 1, further comprising preparing

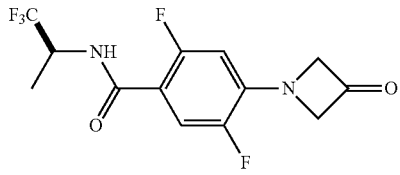 (Compound 1x)

wherein Compound 1x is prepared by a process comprising reacting (Compound 1c)

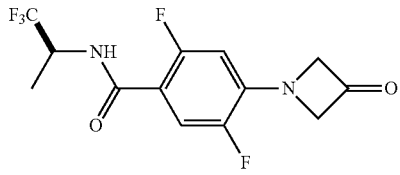

with diethyl cyanomethylphosphonate in the presence of a base.

30. The process of claim 29, wherein the reacting of Compound 1c with diethyl cyanomethylphosphonate in the presence of a base is carried out in an organic solvent component.

31. The process of claim 30, wherein the organic solvent component comprises tetrahydrofuran, ethanol, or a mixture thereof.

32. The process of claim 29, further comprising preparing Compound 1c wherein Compound 1c is prepared by a process comprising reacting

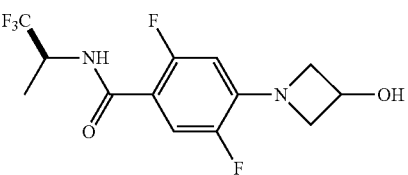 (Compound 1b)

with iodobenzene diacetate and 2,2,6,6-tetramethyl-1-piperidinyloxy free radical (TEMPO).

33. The process of claim 32, further comprising preparing Compound 1b wherein Compound 1b is prepared by a process comprising reacting

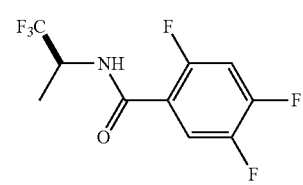 (Compound 1a) 

with in the presence of DBU.

34. The process of claim 33, further comprising preparing Compound 1a wherein Compound 1a is prepared by a process comprising reacting

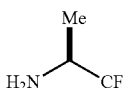 with 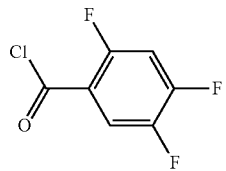

in the presence of a base.

35. The process of claim 28, further comprising preparing

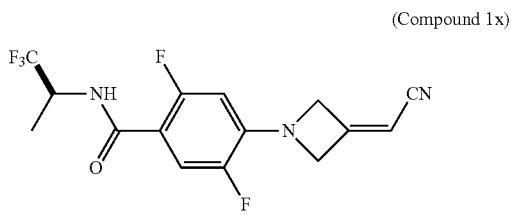 [SMILES: C[C@H](NC(=O)c1cc(F)c(N2CC(=CC#N)C2)cc1F)C(F)(F)F]
(Compound 1x)

by a process comprising:
reacting

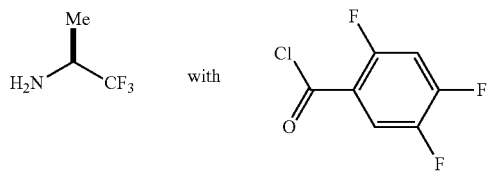 [SMILES: C[C@H](N)C(F)(F)F ; O=C(Cl)c1cc(F)c(F)cc1F]
with in the presence of a base to form

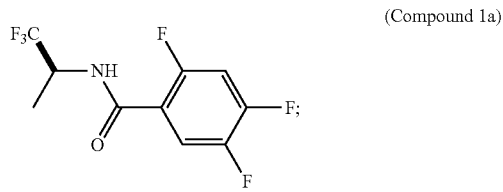 [SMILES: C[C@H](NC(=O)c1cc(F)c(F)cc1F)C(F)(F)F]
(Compound 1a)

reacting Compound 1a with

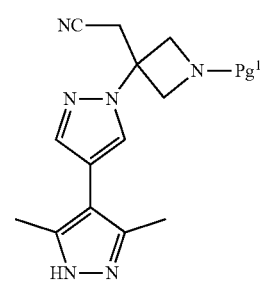

in the presence of DBU to form

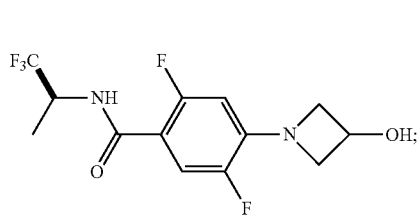
(Compound 1b)

reacting Compound 1b with iodobenzene diacetate and TEMPO to form

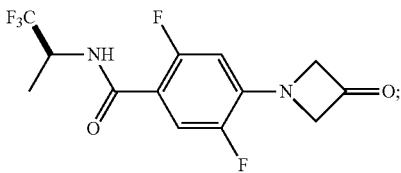
(Compound 1c)

and
reacting Compound 1c with diethyl cyanomethylphosphonate in the presence of a base to form Compound 1x.

36. A process of preparing a compound of Formula A:

A comprising reacting 3,5-dimethyl-1H,1'H-4,4'-bipyrazole with a compound of Formula B:

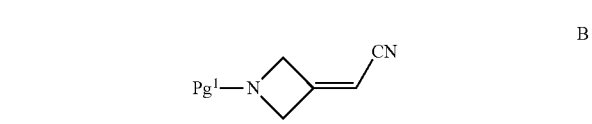
B wherein $Pg^1$ is an amine protecting group.

37. The process of claim 36, wherein $Pg^1$ is tert-butoxycarbonyl.

38. The process of claim 36, wherein the reacting is performed in the presence of 1,8-diazabicyclo[5.4.0]undec-7-ene.

39. The process of claim 38, wherein less than 1 equivalent of the 1,8-diazabicyclo[5.4.0]undec-7-ene is used based on 1 equivalent of the compound of Formula B.

40. The process of claim 38, wherein about 0.2 to about 0.3 equivalents of the 1,8-diazabicyclo[5.4.0]undec-7-ene is used based on 1 equivalent of the compound of Formula B.

41. The process of claim 36, wherein about 1.0 to about 1.1 equivalents of the 3,5-dimethyl-1H,1'H-4,4'-bipyrazole is used based on 1 equivalent of the compound of Formula B.

42. The process of claim 36, wherein the reacting is performed at about room temperature.

43. The process of claim 36, wherein the reaction of 3,5-dimethyl-1H,1'H-4,4'-bipyrazole with the compound of Formula B is performed in the presence of a solvent component.

44. The process of claim 43, wherein the solvent component comprises dimethyl sulfoxide.

45. The process of claim 43, wherein the solvent component comprises dimethyl sulfoxide and methylene chloride.

46. The process of claim 36, further comprising deprotecting the compound of Formula A to form a compound of Formula C:

C

[Structure of Formula C: azetidine bearing NC-CH2 group and NH, linked to pyrazole-pyrazole (dimethyl) system]

or a salt thereof.

47. The process of claim 46, wherein the deprotecting comprises reacting the compound of Formula A in the presence of a trialkylsilyl halide.

48. The process of claim 47, wherein the trialkyl silyl halide is trimethylsilyl iodide.

49. The process of claim 47, wherein the deprotecting is performed in the presence of a solvent component.

50. The process of claim 49, wherein the solvent component comprises methylene chloride.

51. The process of claim 49, wherein the solvent component comprises methylene chloride and methanol.

52. The process of claim 47, wherein the deprotecting is performed at about room temperature.

53. The process of claim 47, further comprising reacting the compound of Formula C, or a salt thereof, with an amine base, to form the free base form of the compound of Formula C.

54. The process of claim 53, wherein the amine base is triethylamine.

55. The process of claim 53, wherein reaction of the compound of Formula C, or a salt thereof, with an amine base is performed in the presence of a solvent component.

56. The process of claim 55, wherein the solvent component comprises methylene chloride.

57. The process of claim 53, further comprising reacting free base form of the compound of Formula C with Compound 1a:

1a

[Structure of Compound 1a: trifluorinated benzamide with CF3-bearing chiral amine]

in the presence of a base and an alkali metal halide to form Compound 1:

or a salt thereof.

58. The process of claim 57, wherein the base is a bicarbonate base.

59. The process of claim 57, wherein the base is sodium bicarbonate.

60. The process of claim 57, wherein the alkali metal halide is lithium chloride.

61. The process of claim 57, wherein the reacting is performed at a temperature of from about 80° C. to about 90° C.

62. The process of claim 57, wherein the reaction of the free base form of the compound of Formula C with Compound 1a is performed in the presence of a solvent component.

63. The process of claim 62, wherein the solvent component comprises dimethyl sulfoxide.

64. The process of claim 62, wherein the solvent component comprises dimethyl sulfoxide and isopropyl acetate.

65. The process of claim 57, further comprising reacting Compound 1 with a strong acid to form a salt form of Compound 1.

66. The process of claim 57, further comprising reacting Compound 1 with hydrochloric acid to form Compound 1 hydrochloric acid salt:

[Structure of Compound 1 HCl salt]

HCl

67. The process of claim 66, further comprising reacting the Compound 1 hydrochloric acid salt with a bicarbonate base to form the free base form of Compound 1.

68. The process of claim 67, wherein the bicarbonate base is potassium bicarbonate.

69. The process of claim 67, further comprising reacting the free base form of Compound 1 with phosphoric acid to form Compound 1 phosphoric acid salt:

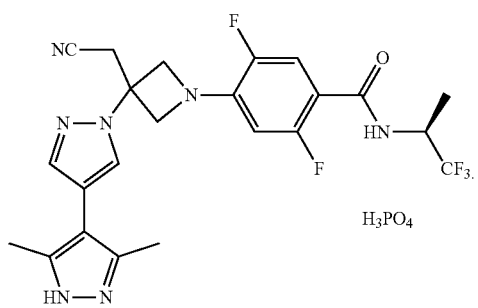

H₃PO₄

70. The process of claim 69, wherein the reacting is performed at about room temperature.

71. The process of claim 69, wherein the reaction of the free base form of Compound 1 with phosphoric acid is performed in the presence of a solvent component.

72. The process of claim 71, wherein the solvent component comprises water.

73. The process of claim 71, wherein the solvent component comprises water and isopropyl alcohol.

74. The process of claim 69, further comprising isolating the Compound 1 phosphoric acid salt.

75. The process of claim 74, wherein the Compound 1 phosphoric acid salt is isolated by recrystallization.

76. The process of claim 74, wherein the Compound 1 phosphoric acid salt is isolated by recrystallization from a mixture of methanol, isopropanol, and methylcyclohexane.

77. A process of preparing Compound 1 phosphoric acid salt:

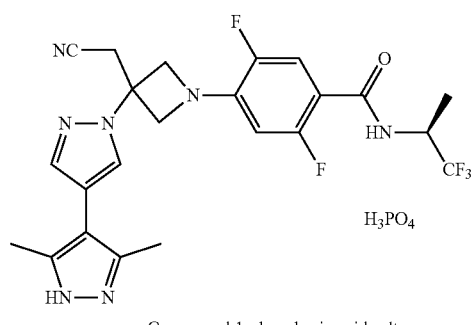

H₃PO₄

Compound 1 phosphoric acid salt comprising:
reacting 3,5-dimethyl-1H,1'H-4,4'-bipyrazole with tent-butyl 3-(cyanomethylene)azetidine-1-carboxylate in the presence of 1,8-diazabicyclo[5.4.0]undec-7-ene to form the compound of Formula A-1:

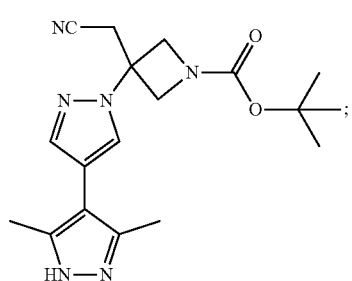

A-1 deprotecting the compound of Formula A-1 to form the compound of Formula C-1:

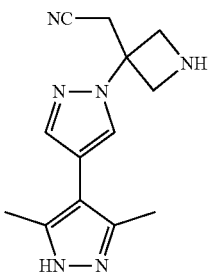

C-1 or a salt thereof;
reacting the compound of Formula C-1 with triethylamine to form the free base form of the compound of Formula C-1;
reacting the free base form of the compound of Formula C-1 with Compound 1a:

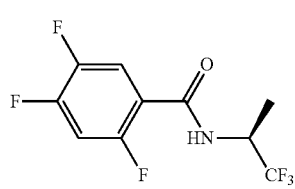

1a in the presence of sodium bicarbonate and lithium chloride to form Compound 1:

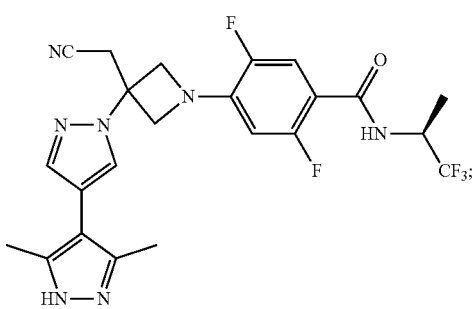 [SMILES: Cc1n[nH]c(C)c1-c1cnn(C2(CC#N)CN(c3cc(F)c(C(=O)N[C@@H](C)C(F)(F)F)cc3F)C2)c1]

reacting Compound 1 with hydrochloric acid to form Compound 1 hydrochloric acid salt:

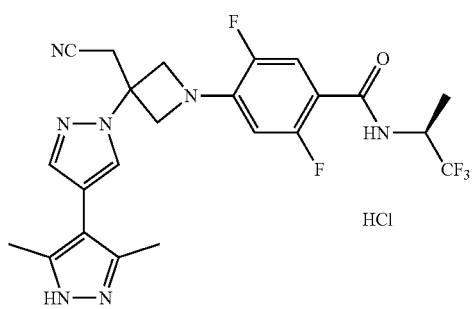 [SMILES: Cc1n[nH]c(C)c1-c1cnn(C2(CC#N)CN(c3cc(F)c(C(=O)N[C@@H](C)C(F)(F)F)cc3F)C2)c1 ; Cl]

HCl reacting Compound 1 hydrochloric acid salt with potassium bicarbonate to form the free base form of Compound 1; and reacting the free base form of Compound 1 with phosphoric acid to form the Compound 1 phosphoric acid salt.

78. The process of claim 77, further comprising isolating the Compound 1 phosphoric acid salt.

79. The process of claim 78, wherein the Compound 1 phosphoric acid salt is isolated by recrystallization.

80. The process of claim 78, wherein the Compound 1 phosphoric acid salt is isolated by recrystallization from a mixture of methanol, isopropanol, and methylcyclohexane.

* * * * *

UNITED STATES PATENT AND TRADEMARK OFFICE
CERTIFICATE OF CORRECTION

PATENT NO. : 11,685,731 B2
APPLICATION NO. : 17/337065
DATED : June 27, 2023
INVENTOR(S) : Jiacheng Zhou et al.

Page 1 of 2

It is certified that error appears in the above-identified patent and that said Letters Patent is hereby corrected as shown below:

In the Claims

Column 62, Line 46-51 (approx.), Claim 22 – delete " 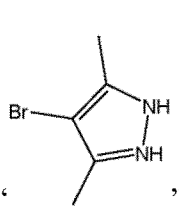 " and insert -- 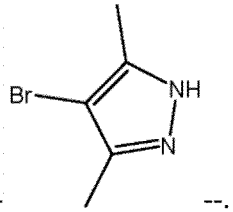 --.

Column 62, Line 55, Claim 23 – before "solvent" insert -- a --.

Column 62, Line 56, Claim 23 – delete "alladium" and insert -- palladium --.

Column 63, Line 4-10 (approx.), Claim 28 – delete " 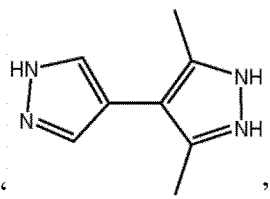 " and insert -- 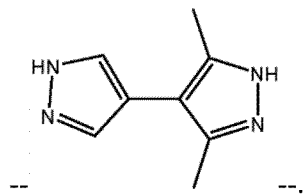 --.

Column 63, Line 15-26 (approx.), Claim 28 – delete

Signed and Sealed this
Twenty-first Day of May, 2024

Katherine Kelly Vidal
*Director of the United States Patent and Trademark Office*

CERTIFICATE OF CORRECTION (continued)
U.S. Pat. No. 11,685,731 B2

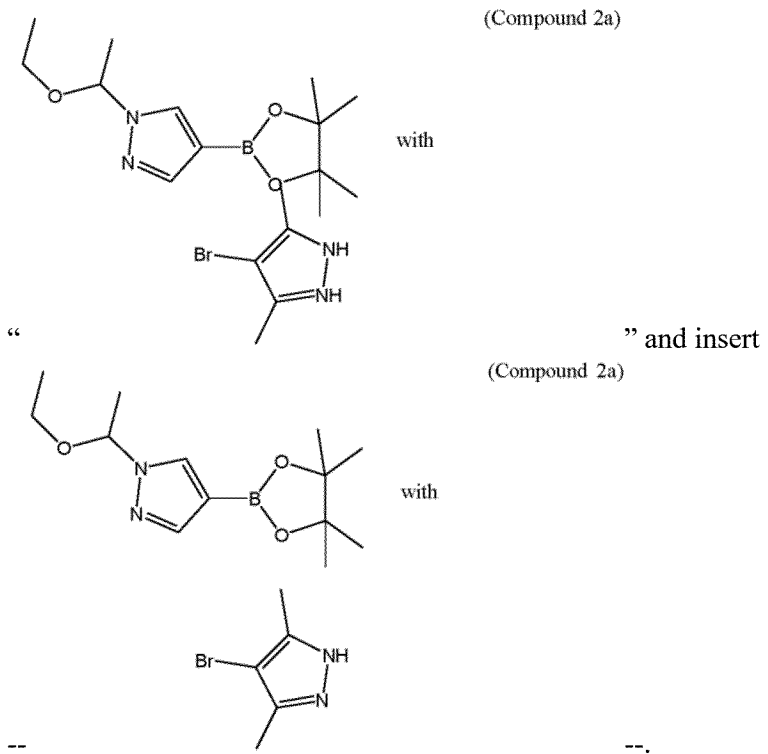

Column 69, Line 49, Claim 77 – delete "tent-" and insert -- tert- --.